US011597772B2

(12) United States Patent
Oestergaard

(10) Patent No.: US 11,597,772 B2
(45) Date of Patent: Mar. 7, 2023

(54) OBINUTUZUMAB TREATMENT OF A DLBCL PATIENT SUBGROUP

(71) Applicants: Hoffmann-La Roche Inc., Little Falls, NJ (US); NanoString Technologies, Inc., Seattle, WA (US)

(72) Inventor: Mikkel Zahle Oestergaard, Zollikon (CH)

( * ) Notice: Subject to any disclaimer, the term of this patent is extended or adjusted under 35 U.S.C. 154(b) by 171 days.

(21) Appl. No.: 16/784,021

(22) Filed: Feb. 6, 2020

(65) Prior Publication Data

US 2020/0317800 A1  Oct. 8, 2020

Related U.S. Application Data

(63) Continuation of application No. PCT/EP2018/071462, filed on Aug. 8, 2018.

(60) Provisional application No. 62/542,489, filed on Aug. 8, 2017.

(51) Int. Cl.
 C07K 16/28 (2006.01)
 A61K 45/06 (2006.01)
 A61K 39/00 (2006.01)

(52) U.S. Cl.
 CPC .......... *C07K 16/2887* (2013.01); *A61K 45/06* (2013.01); *A61K 2039/54* (2013.01); *A61K 2039/545* (2013.01); *C07K 2317/24* (2013.01); *C07K 2317/52* (2013.01); *C07K 2317/732* (2013.01)

(58) Field of Classification Search
 CPC ............ C07K 16/2887; C07K 2317/24; A61K 45/06; A61K 2039/54; A61K 2039/545
 See application file for complete search history.

(56) References Cited

U.S. PATENT DOCUMENTS

2016/0283653 A1* 9/2016 Staudt .................... G16B 25/10
2017/0000900 A1* 1/2017 Romanelli ......... A61K 47/6867

FOREIGN PATENT DOCUMENTS

WO WO-2016/049214 A1 3/2016
WO WO-2017/097723 A2 6/2017
WO WO-2019/030260 A1 2/2019

OTHER PUBLICATIONS

Gabellier et al., Obinutuzumab for relapsed or refractory indolent non-Hodgkin's lymphomas, Therapeutic Advances in Hematology, 7(2):85-93, Publication Date: Dec. 27, 2015 (Year: 2015).*
GAZYVA Prescribing Information, Reference ID: 4937323 (Year: 2022).*
NCT01287741 retrieved from: https://clinicaltrials.gov/ct2/show/NCT01287741, version of May 5, 2015 (Year: 2015).*
DLBCL, retrieved from on Mar. 3, 2022: https://lymphoma.org/aboutlymphoma/nhl/dlbcl/ (Year: 2022).*
Miller et al., Chemotherapy Alone Compared With Chemotherapy Plus Radiotherapy for Localized Intermediate- and High-Grade Non-Hodgkin's Lymphoma, The New England Journal of Medicine, 339 (1): 21-26, Publication Date: Jul. 2, 1998 (Year: 1998).*
The Science Behind Radiation Therapy, American Cancer Society, Publication Date: Oct. 27, 2014 (Year: 2014).*
Cartron et al., "Obinutuzumab: what is there to learn from clinical trials?" Blood. 130(5):581-9 (2017) (10 pages).
Chiu et al., "CC-122 exhibits potent anti-lymphoma activity in combination with obinutuzumab through cell autonomous and antibody dependent cell mediated cytotoxicity," Blood. 126(23) (2015) (7 pages).
Dubois et al., "Next-generation sequencing in diffuse large b-cell lymphoma highlights molecular divergence and therapeutic opportunities: a LYSA study," Clin Cancer Res. 22(12):2919-28 (2016) (11 pages).
Lenz et al.,"Molecular subtypes of diffuse large B-cell lymphoma arise by distinct genetic pathways," Proc Natl Acad Sci U S A. 105(36):13520-5 (2008).
Lim et al., "Precision Medicine for Diffuse Large B-cell Lymphoma," Clin Cancer Res. 22(12):2829-2831 (2016) (4 pages).
Matasar et al., "Polatuzumab vedotin plus bendamustine and rituximab or obinutuzumab in relapsed/refractory follicular lymphoma or diffuse large b-cell lymphoma: updated results of a phase 1B/2 study," Haematologica. 102(s2):173 (2017).
Michot et al., "CC-122 in combination wiht obinutuzumab (GA101): phase IB study in relapsed or refractory patients with diffuse large B-cell lymphoma, follicular lymphoma, or marginal zone lymphoma," Haematologica. 120(s2):172-3 (2017).
Scott et al., "Determining cell-of-origin subtypes of diffuse large B-cell lymphoma using gene expression in formalin-fixed paraffin-embedded tissue," Blood. 123(8):1214-7 (2014).
Scott et al., "Prognostic significance of diffuse large b-cell lymphoma cell of origin determined by digital gene expression in formalin-fixed paraffin-embedded tissue biopsies," J Clin Oncol. 33(26):2848-56 (2015).

(Continued)

*Primary Examiner* — Misook Yu
*Assistant Examiner* — Cheng Lu
(74) *Attorney, Agent, or Firm* — Clark & Elbing LLP; Karen L. Elbing

(57) ABSTRACT

The present invention relates to obinutuzumab (or its functional equivalents) for use in the treatment of a particular biomarker-defined DLBCL patient and a novel DLBCL patient subgroup, respectively. The present invention further relates to a method for treating DLBCL with obinutuzumab (or its functional equivalents) in a patient in need thereof, wherein said patient is a particular biomarker-defined DLBCL patient or belongs to a novel biomarker-defined DLBCL patient subgroup. The present invention further relates to the use of obinutuzumab (or its functional equivalents) for the preparation of a pharmaceutical composition for the treatment of DLBCL in the particular biomarker-defined DLBCL patient/novel DLBCL patient subgroup. The present invention further relates to a method for identifying a particular DLBCL patient/novel DLBCL patient subgroup and a method for diagnosing a novel form of DLBCL and a particular DLBCL patient/novel DLBCL patient subgroup, respectively.

26 Claims, 17 Drawing Sheets
(16 of 17 Drawing Sheet(s) Filed in Color)
Specification includes a Sequence Listing.

(56) References Cited

OTHER PUBLICATIONS

Tomita, "Genetic and Epigenetic Modulation of CD20 Expression in B-Cell Malignancies: Molecular Mechanisms and Significance to Rituximab Resistance," J Clin Exp Hematop. 56(2):89-99 (2016).
Vitolo et al., "Obinutuzumab or rituximab plus CHOP in patients with previously untreated diffuse large B-cell lymphoma: final results from an open-label, randomized phase 3 study (GOYA)," Blood. 128(22) (2016) (8 pages).
Wright et al., "A gene expression-based method to diagnose clinically distinct subgroups of diffuse large B cell lymphoma," Proc Natl Acad Sci U S A. 100(17):9991-6 (2003).
Zelenetz et al., "Results of a phase Ib study of venetoclax plus R- or G-CHOP in patients with B-Cell non-hodgkin lymphoma," Blood. 128 (2016) (8 pages).
Zhai et al., "Pharmacokinetics of obinutuzumab in Chinese patients with B-cell lymphomas," Br J Clin Pharmacol. 83(7):1446-56 (2017).
International Preliminary Report on Patentability for International Patent Application No. PCT/EP2018/071462, dated Oct. 10, 2019 (16 pages).
International Search Report for International Patent Application No. PCT/EP2018/071462, dated Nov. 15, 2018 (21 pages).
Sehn et al., "Prognostic Impact of BCL2 and MYC Expression and Translocation in Untreated DLBCL: Results from the Phase III Goya Study," Hematological Oncology. 35(S2):131-133. Abstract No. 122 (Jun. 2017).
Notice of Reasons for Rejection for Japanese Patent Application No. 2020-505912, dated Sep. 6, 2022 (12 pages).

\* cited by examiner

KM (PFS) in GOYA for
CD58 mutations
(any mutation type)

FIG. 9 (con't)
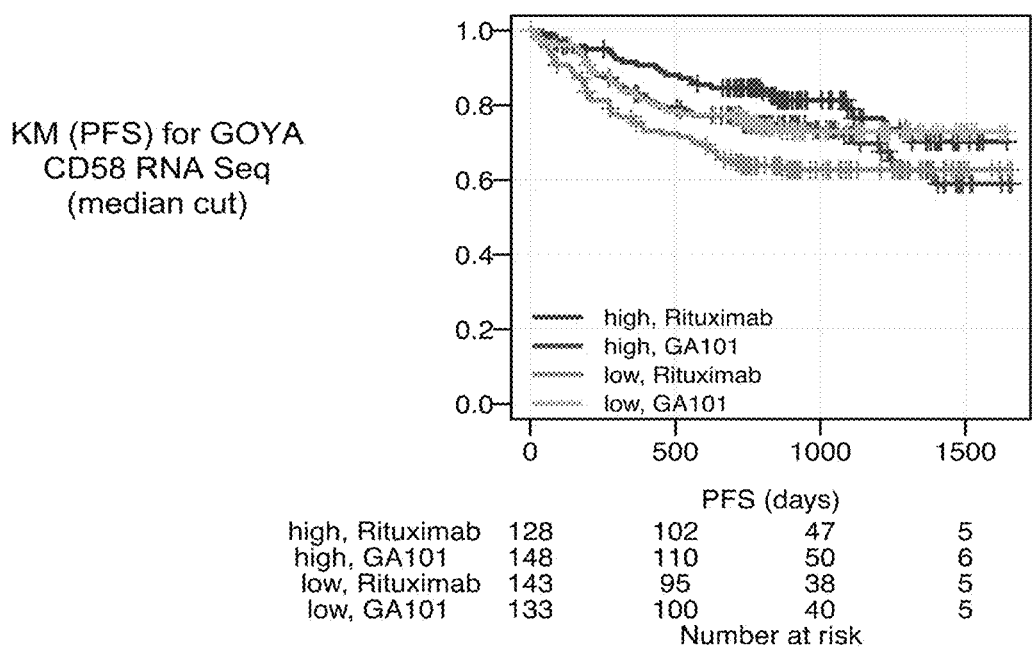
KM (PFS) for GOYA CD58 RNA Seq (median cut)
Forest plot evaluating treatment effect (G vs. R) in quartiles of CD58 gene expression
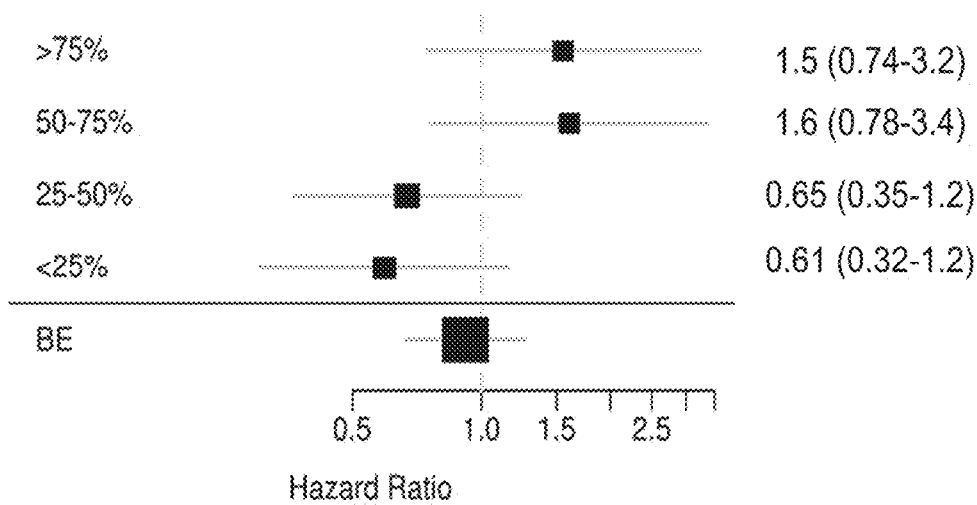

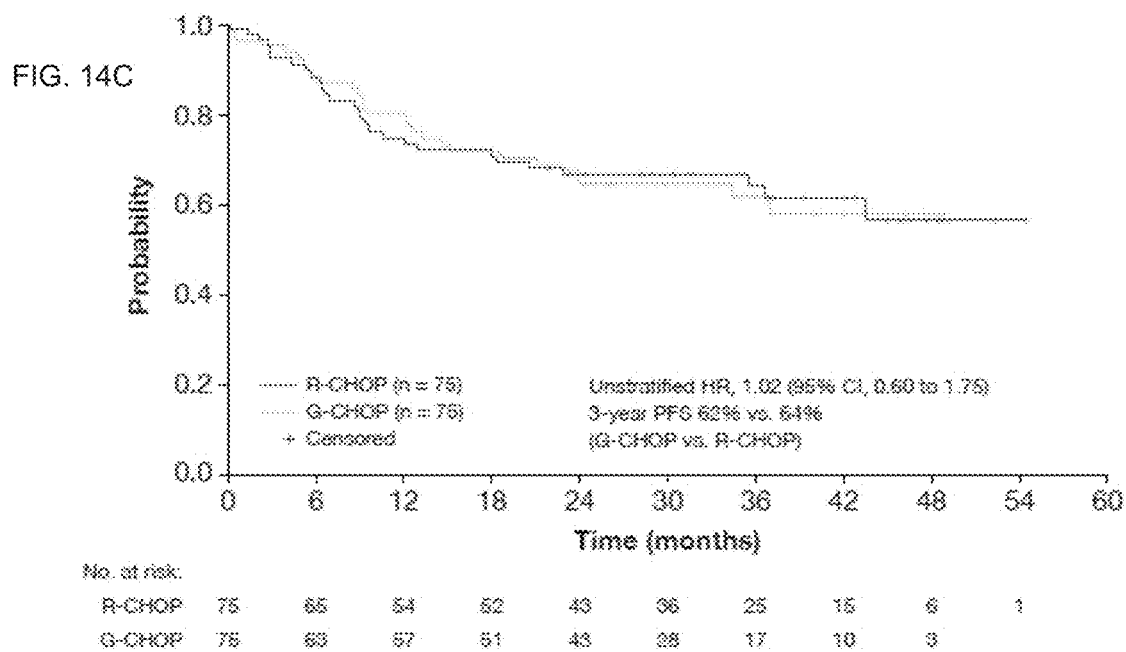

OBINUTUZUMAB TREATMENT OF A DLBCL PATIENT SUBGROUP

The instant application contains a Sequence Listing which has been submitted electronically in ASCII format and is hereby incorporated by reference in its entirety. Said ASCII copy, created on Feb. 4, 2020, is named 51177-029001_Sequence_Listing_2.4.2020_ST25 and is 31,725 bytes in size.

The present invention relates to obinutuzumab (or its functional equivalents) for use in the treatment of a particular biomarker-defined DLBCL patient and a novel DLBCL patient subgroup, respectively. The present invention further relates to a method for treating DLBCL with obinutuzumab (or its functional equivalents) in a patient in need thereof, wherein said patient is a particular biomarker-defined DLBCL patient or belongs to a novel biomarker-defined DLBCL patient subgroup. The present invention further relates to the use of obinutuzumab (or its functional equivalents) for the preparation of a pharmaceutical composition for the treatment of DLBCL in the particular biomarker-defined DLBCL patient/novel DLBCL patient subgroup. The present invention further relates to a method for identifying a particular DLBCL patient/novel DLBCL patient subgroup and a method for diagnosing a novel form of DLBCL and a particular DLBCL patient/novel DLBCL patient subgroup, respectively.

Diffuse large B-cell lymphoma (DLBCL) is the most common type of aggressive non-Hodgkin lymphoma (NHL). Immunochemotherapy with the anti-CD20 monoclonal antibody (mAb) rituximab (R), plus cyclophosphamide, doxorubicin, vincristine, and prednisone (CHOP), is the standard-of-care treatment for previously untreated patients who present with advanced-stage disease (Coiffier, N. Engl. J. Med. 346, 2002, 235-242; Tilly, Ann. Oncol. 26, 2015, v116-v125 (suppl 5); NCCN Clincal Practice Guidelines in Oncology: Non-Hodgkin's Lymphomas, Version 3. 2016). Studies have shown a complete and unconfirmed complete response (CR/CRu) rate of 76% (GELA trial) (Coiffier loc. cit.), and a 2-year failure-free survival rate of 77% (Habermann, J. Clin. Oncol. 24, 2006, 3121-3127). Although first-line (1L) treatment for DLBCL is curative for many patients (Maurer, J. Clin. Oncol. 32, 2014, 1066-1073), there is still a need to improve outcome for the 20-40% of patients who fail to achieve a remission or who relapse, and outcomes with salvage therapy remain poor (Sehn, Blood 125, 2015, 22-32).

Obinutuzumab (Gazyva™/Gazyvaro™ GA101; G) is a glycoengineered, type II anti-CD20 mAb with greater direct cell death induction, and antibody-dependent cellular cytotoxicity and phagocytosis than R (Herter, Mol. Cancer Ther. 12, 2013, 2031-2042; Mossner, Blood 115, 2010, 4393-4402; EP-B1 2380910; WO 2005/044859; see also Illidge, Expert Opin. Biol. Ther. 12(5), 2012, 543-5). In phase 3 studies of previously untreated patients with chronic lymphocytic leukemia (CLL) and coexisting conditions (CLL11), or follicular lymphoma (FL; GALLIUM), G proved more effective than R (Goede, N. Engl. J. Med. 370, 2014, 1101-1110; Marcus, N. Engl. J. Med. (Accepted May 2017: in press). In smaller studies, G monotherapy and G-CHOP have demonstrated promise in aggressive forms of non-Hodgkin lymphoma (NHL), including DLBCL (Morschhauser, J. Clin. Oncol. 31, 2013, 2912-2919; Zelenetz, Blood 122, 2013, 1820). Also Owen (Expert Opin. Biol. Ther. 12(3), 2012, 343-51) discusses the use of Obinutuzumab for the treatment of lymphoproliferative disorders. A multicenter, open-label, randomized, clinical phase 3 study (GOYA; see below for further details) compared the efficacy and safety of G-CHOP with R-CHOP in previously untreated patients with DLBCL. However, in GOYA, G-CHOP did not improve the clinical outcome (e.g. progression free survival (PFS)) relative to R-CHOP in previously untreated DLBCL (1 L DLBCL) with respect to the entive 1L DLBCL patient group that was initially intended to be treated in the context of GOYA.

Scott (Blood 123(8), 2014, 1214-7; JCO 33(26), 2015, 2848 57; Am. Soc. Clin. Oncol. Educ. Book 2015, 35:e458-66) and others (Nowakowski, Am. Soc. Clin. Oncol. Educ. Book 2015, 35:e449-57) performed gene expression-based determination of cell-of-origin (COO) subtypes of DLBCL by using the NanoString Lymph2Cx assay (Scott 2014 and 2015 loc. cit.). In particular, Scott (2014 and 2015 loc. cit.) assigned the COO subtypes of DLBCL, germinal-center B-cell-like DLBCL (GCB DLBCL), activated B-cell-like DLBCL (ABC DLBCL) and unclassified DLBCL, on the basis of a 20-gene gene expression assay and Linear Predictor Scores (LPSs) of ~<1900, ~1900-~2450 and ~>2450, respectively, (cf. Scott 2014 loc. cit., FIG. 1). Scott (2014 and 2015 loc. cit.) also assessed the treatment effect of R-CHOP on these COO subtypes of DLBCL.

Punnoose (Blood 126, 2015, 3971) describes the prevalence and prognostic value of BCL2 and MYC protein expression within ABC and GCB COO subtypes in patients with previously untreated DLBCL from MAIN, a phase III trial that evaluated bevacizumab plus R-CHOP (NCT 00486759).

Challa-Malladi (Cancer Cell 20, 2011, 728-40) discloses that combined genetic inactivation of β2-Microglobulin and CD58 reveals frequent escape from immune recognition in DLBCL.

Despite previous success in the treatment of DLBCL (for example due to the advances with R, in particular R-CHOP), however, there is still a high unmet medical need for some DLBCL patients (cf. NCCN clinical practice guidelines in oncology; non-Hodgkin's lymphoma, v 2.2015) for an improved treatment (cf. Sehn, loc. cit.).

Therefore, the technical problem underlying the present invention is to provide an improved treatment of DLBCL in certain patients.

The solution to said technical problem is provided herein below and characterized in the appended claims.

It was surprisingly found in the context of the invention that, of all DLBCL patients, some patients respond to a treatment with obinutuzumab (in particular in combination with a chemotherapy, more particular in combination with a CHOP chemotherapy) by an improved clinical outcome, in particular as compared to a treatment with rituximab (in particular in combination with a chemotherapy, more particular in combination with a CHOP chemotherapy). It was also surprisingly found in the context of the invention that subgroups of DLBCL patients can be identified/determined which respond to a treatment with obinutuzumab (in particular in combination with a chemotherapy, more particular in combination with a CHOP chemotherapy) by an improved clinical outcome, in particular as compared to a treatment with rituximab (in particular in combination with a chemotherapy, more particular in combination with a CHOP chemotherapy). It was also surprisingly found in the context of the invention that there are DLBCL patients which respond to a treatment with obinutuzumab (in particular in combination with a chemotherapy, more particular in combination with a CHOP chemotherapy) by an improved clinical outcome, in particular as compared to a treatment with rituximab (in particular in combination with a chemotherapy, more particular in combination with a CHOP chemotherapy). It is the main gist of the invention that such particular DLBCL patients and subgroups of DLBCL patients, respectively, can indeed be defined; also referred to herein as "patient defined herein". It is a further gist of the invention that such a patient can be defined by biomarkers (also referred to herein as "predictive biomarkers" and "predictive biomarker-defined patient", respectively).

In particular, based on exploratory analyses of GOYA, it was demonstrated in the context of the invention, and is illustrated by the appended examples, that obinutuzumab is superior over rituximab (each in combination with a CHOP chemotherapy) in (a) subset(s) of GCB DLBCL patients (e.g. in a new molecular follicular lymphoma (FL)-like GCB DLBCL patients subgroup) and/or in DLBCL patients with mutations in CD58 and/or with low expression of CD58. This was the first time that an obinutuzumab benefit over R has been identified for certain patients, in particular for a patient defined herein.

For example, in the context of the present invention, the following biomarker-defined DLBCL patients that benefit from treatment with G (e.g. G-CHOP) over the treatment with R (e.g. R-CHOP) have been identified/determined:
  BCL2 translocated patients (see, for example, FIG. 4);
  BCL2 protein expression positive patients (see, for example, FIG. 5);
  BCL2 translocated patients that are BCL2 protein expression positive (see, for example, FIG. 6);
  (a) subset(s) of GCB DLBCL patients. These can, for example, be identified as:
    subgroup (COO) classification of GCB patients by cutoffs of the Linear Predictor Score (LPS) into subgroup "strong-GCB" patients (patients with LPS<cutoff; e.g. as compared to the general GCB DLBCL cutoff of LPS~1900) (see, for example, FIGS. 7, 10 and 12);
    GCB patients with high BCL2 gene expression;
    GCB patients that are BCL2 protein expression positive;
    GCB patients with BCL2 translocation;
    GCB patients with BCL2 translocation that are BCL2 protein expression positive (see, for example, FIG. 8);
  CD58 mutated patients and/or patients with low expression of CD58 (see, for example, FIG. 9).

More particular, based on exploratory analyses of GOYA, it was demonstrated in the context of the invention, and is illustrated by the appended examples, that an assessment of the LPS as a continuous variable identified a subgroup of GCB patients that benefitted from G (in particular G-CHOP) over R (in particular R-CHOP). Even more particular, it was observed that weighted expression of a gene expression (GE) array profile (measured by LPS) was linked with benefit in outcome from G treatment (e.g. G-CHOP) over R treatment (e.g. R-CHOP) among GCB patients in GOYA.

On this basis, new LPS cutoffs defining a strong-GCB DLBCL subgroup of patients with benefit from G treatment over R treatment could be determined. These new cutoffs are substantially below the LPS cutoff usually allocated to GCB DLBCL (~<1900)). For example, a new LPS cutoff of ≤749 was determined in multivariate simulation analyses (cf. FIG. 10). In accordance with this example, 'strong-GCB' patients, defined as patients with an LPS of ≤749, represented 25% (233/933) of evaluable DLBCL patients and 43% (233/540) of evaluable GCB patients in GOYA. As another example, a new LPS cutoff of ≤725 was determined in multivariate simulation analyses (cf. FIGS. 10, 12). In accordance with this example, 'strong-GCB' patients are defined more stringently as patients with an LPS of ≤725. These patients represent 25% (229/933) of evaluable DLBCL patients and 43% (229/540) of evaluable GCB patients in GOYA. An LPS cutoff around 725 was shown to reflect extraordinary robustness and high generalizability of results to independent cohorts ("patient defined herein"), i.e. strong-GCB DLBCL patients. This was shown by bootstrap simulations. Strong-GCB patients treated with G (G-CHOP) achieved significantly better clinical outcomes, for example in terms of progression-free survival (PFS), event-free survival (EFS), and overall survival (OS), than those treated with R (R-CHOP) (cf. Table 4). High-level safety was similar with either treatment regimen. In gene-set enrichment analyses on FoundationOne® Heme (FOH) data, strong-GCB patients were further characterized as significantly enriched for FL somatic mutation hallmarks, as compared to other GCB patients, referred to as "weak-GCB" patients (e.g. false-discovery rates, FDR, 3.54e-9). In particular, BCL2 translocations and mutations/mutation rates in several m7-FLIPI genes (BCL2, BCL6, CD70, CDKN2A, CREBBP, EP300, IGH, MEF2B, MYC, MYD88, PCLO, TNFAIP3, TNFRSF14) were highly enriched in strong-GCB patients, and/or in DLBCL patients with BCL2 translocations and/or with high BCL2 expression, as compared to other DLBCL patients (at an FDR<5%; FIGS. 11A and 11B. There was no evidence for transformed indolent NHL in the strong-GCB subset on central pathology review.

In sum, new clinically and molecularly distinct subtypes of DLBCL, in particular of GCB DLBCL, have been identified, inter alia a subtype referred to as 'strong-GCB'. The identified subtypes represent de novo DLBCLs. These exhibit molecular features of FL, such as FL-typical mutations (cf. Morin, Nature 476 (7360), 2011, 298-303), they clinically differ, however, from FL. Treatment with G (e.g. G-CHOP) confers a substantial clinical benefit over treatment with R (e.g. R-CHOP) in these new subsets of (GCB) DLBCL patients ("patient defined herein"), in particular of 1L (GCB) DLBCL.

Accordingly, the invention provides for means and methods for identifying/determining/diagnosing (a) subset(s) of (GCB) DLBCL patients that advantageously respond to obinutuzumab ("patient defined herein"), in particular more advantageously to obinutuzumab than to R. The identification/determination/diagnosis can be performed by several ways, e.g. by determining whether there is a BCL2 translocation and/or a BCL2 protein overexpression, whether there is (are) (a) genetic mutation(s) in CD58 and/or there is lowered CD58 expression, or by gene expression profiling/determining weighted gene expression (e.g. by employing the NanoString COO assay) and using novel cutoffs for the LPS (as described herein elsewhere).

More particular, the invention relates to a method for identifying a DLBCL patient (patent with/suffering from DLBCL) which responds to a treatment with obinutuzumab (in particular in combination with a chemotherapy, more particular in combination with a CHOP chemotherapy) by reaching an improved clinical outcome as compared to a treatment with rituximab (in particular in combination with a chemotherapy, more particular in combination with a CHOP chemotherapy). Said method comprising (the step of) determining (e.g. by using a (tumor) sample of a patient) whether a patient is a patient defined herein.

The invention further relates to a method for diagnosing in a patient a form of DLBCL which can be treated with obinutuzumab (in particular in combination with a chemotherapy, more particular in combination with a CHOP chemotherapy) so that an improved clinical outcome as compared to a treatment with rituximab (in particular in combination with a chemotherapy, more particular in combination with a CHOP chemotherapy) is reached. Said method comprising (the step of) determining (e.g. by using a (tumor) sample of a patient) whether a patient is a patient defined herein. Said method (further) comprising (the step of) diagnosing said form of DLBCL if the patient is a patient defined herein.

The present invention also relates to the medical intervention/treatment of the patient defined herein by obinutuzumab, or by a functional equivalent thereof. In principle, the term "obinutuzumab" as used herein also embraces its functional equivalents (see below for further explanations/definitions).

In one aspect, the present invention relates to obinutuzumab for use in the treatment of DLBCL in a patient defined herein.

In the context of this use, it is, for example, envisaged that (i) it has been determined (e.g. by using a (tumor) sample of a patient) whether a patient to be treated is a patient defined herein, (ii) a patient to be treated has been identified according to the method for identifying of the invention, or (iii) a form of DLBCL has been diagnosed in a patient to be treated according to the method for diagnosing of the invention.

In another aspect, the present invention relates to obinutuzumab for use in the treatment of DLBCL in a patient defined herein, wherein it is, for example, envisaged that said treatment comprises the step of (i) determining (e.g. by using a (tumor) sample of a patient) whether a (DLBCL) patient to be treated is a patient as defined herein, (ii) identifying a DLBCL patient according to the method for identifying of the invention, or (iii) diagnosing in the patient a form of DLBCL according to the method for diagnosing of the invention.

In the context of the (step of) determining/identifying/diagnosing, a sample of a (DLBCL) patient, for example a tumor sample of a (DLBCL) patient, may be employed. The determination may be in a sample of a (DLBCL) patient, for example in a tumor sample of a (DLBCL) patient. A non-limiting example of a particular sample to be employed in accordance with the invention is a sample of a tumor tissue/tumor biopsy, more particular a formalin-fixed, paraffin-embedded tumor tissue/tumor biopsy. Such a sample can, for example, be prepared as described in Scott (2014 and 2015 loc. cit.). Other suitable samples are described herein elsewhere.

In another aspect, the present invention relates to a method for treating DLBCL in a patient in need thereof, wherein said patient is a patient defined herein. The method may comprise the steps of obtaining a sample of a patient for whom DLBCL therapy is contemplated and/or testing the/a sample of a patient to determine whether said patient is a patient defined herein. It is envisaged that the method for treating of the invention comprises the step of administering a pharmaceutically effective amount of obinutuzumab to the patient to be treated. In the context of these steps, in particular the step of testing, a (tumor) sample of a (DLBCL) patient may be employed. The testing may be in a (tumor) sample of a (DLBCL) patient. What is said herein above and elsewhere with respect to a "sample" to be employed also applies here, mutatis mutandis.

In the context of these steps, in particular in the context of the step of testing (or instead of that step) also a method for identifying or diagnosing according to the invention may be employed.

In another aspect, the present invention relates to the use of obinutuzumab for the preparation of a pharmaceutical composition for the treatment of DLBCL in a patient defined herein. Said treatment may comprise the step of determining/identifying/diagnosing in accordance with the invention whether a (DLBCL) patient to be treated is a patient as defined herein. In the context of the step of determining/identifying/diagnosing, a sample of a (DLBCL) patient, for example a tumor sample of a (DLBCL) patient, may be employed. The determination may be in a sample of a (DLBCL) patient, for example in a tumor sample of a (DLBCL) patient. What is said herein elsewhere with respect to a "sample" to be employed applies here, mutatis mutandis. Likewise, what has been said above with respect to the use and treatment applies here, mutatis mutandis.

The patient to be treated in accordance with the invention ("patient defined herein") is a patient, in particular a patient with/suffering from DLBCL, that responses to a treatment with obinutuzumab (in particular in combination with a chemotherapy, more particular in combination with a CHOP chemotherapy) by reaching an improved clinical outcome as compared to a treatment with rituximab (in particular in combination with a chemotherapy, more particular in combination with a CHOP chemotherapy).

In one aspect/embodiment of the invention (aspect/embodiment A), the patient defined herein (which is to be treated with obinutuzumab) is a predictive biomarker-defined patient.

A biomarker is "predictive" in accordance with the invention if it can be used to identify a patient defined herein (optionally in combination with one or more other (predictive) biomarkers), i.e. a patient that responses to the treatment with obinutuzumab (in particular in combination with a chemotherapy, more particular in combination with a CHOP chemotherapy) more advantageously than to the treatment with rituximab (in particular in combination with a chemotherapy, more particular in combination with a CHOP chemotherapy). More particular, a biomarker is predictive if the treatment effect (i.e. G treatment as compared to R treatment) differs between the biomarker-defined (subgroups of) patients. It is preferred in this context, that the predictive biomarker(s) is (are) the biomarker(s) as defined herein elsewhere. Particular examples of predictive biomarkers to be assessed in the context of the invention are CD58 (e.g. (a) genetic mutation(s) therein and/or low expression thereof), BCL2 (e.g. translocations and/or high expression thereof) and one or more (preferably all) of the genes TNFRSF13B, LIMD1, IRF4, CREB3L2, PIM2, CYB5R2, RAB7L1, and CCDC50; and MME, SERPINA9, ASB13, MAML3, ITPKB, MYBL1, and S1PR2 (e.g. the weighted expression thereof resulting in an LPS substantially below ~1900). In this context, reference is also made to what is disclosed herein below, in particular in the context of the aspects/embodiments B to G, infra.

In one aspect/embodiment of the invention (aspect/embodiment B), the patient defined herein (which is to be treated with obinutuzumab) is a patient with/suffering from molecular follicular lymphoma (FL)-like germinal-center B-cell (GCB) DLBCL.

"Molecular" in this context means that, on molecular level, the patients resemble FL patients (cf. Morin loc. cit.). It is, however, envisaged that, on clinical level/clinically, the patients do not resemble FL patients.

In accordance with the invention, the molecular FL-like GCB DLBCL according to this aspect/embodiment is preferably characterized as strong-GCB DLBCL in accordance with the invention and/or as DLBCL in patients with BCL2 translocations and/or high BCL2 expression (see aspects/embodiments D and E, infra).

A patient suffering from molecular FL-like GCB DLBCL in accordance with the invention may also be characterized as a patient with one or (preferably) more mutation(s) in one or (preferably) more of the genes selected from the group consisting of BCL2, BCL6, CD70, CDKN2A, CREBBP, EP300, IGH, MEF2B, MYC, MYD88, PCLO, TNFAIP3 and TNFRSF14. Although less preferred, a patient suffering from molecular FL-like GCB DLBCL in accordance with the invention may also be characterized as a patient with one or (preferably) more mutation(s) in one or (preferably) more of the genes selected from the group consisting of BCL2, CREBBP, EP300, EZH2, MEF2B, PCLO, and TNFRSF14, with one or (preferably) more mutation(s) in one or (preferably) more of the genes selected from the group consisting of CREBBP, EP300, EZH2, MEF2B and TNFRSF14, or with one or (preferably) more mutation(s) in one or (preferably) more of the genes selected from the group consisting of EZH2, MEF2B and TNFRSF14.

One particular, however non-limiting, example of an applicable mutation in this respect is a BCL2mutation, in particular a BCL2 translocation (see below for details).

The mutation(s) can, for example, be identified by relying on the appended examples. The Foundation Medicine next-generation sequencing assay, FoundationOne® Heme, can, for example, be used in this respect (according to the manual of the distributor).

In one aspect/embodiment of the invention (aspect/embodiment C), the patient defined herein (which is to be treated with obinutuzumab) is a patient with one or more genetic mutation(s) in CD58 and/or with low expression of CD58.

CD58 (see also Challa-Malladi loc. cit.) is known to be involved in immune recognition of tumor cells and is expressed on tumor cells. CD58 binds to CD2 on effector CTLs and NK cells (thereby providing activating signals of immune effector cells). Presence of genetic aberrations in CD58 is associated with lost or aberrant CD58 surface expression (e.g. detectable by immunohistochemistry, IHC). 67% of DLBCL cases show aberrant CD58 protein expression; with same proportion in GCB and ABC COO subgroups. Nucleotide sequences encoding CD58 and amino acid sequences of CD58, in particular *Homo sapiens* (human) CD58, are well known in the art. Nucleotide sequences encoding CD58, in particular *Homo sapiens* (human) CD58, are, for example, available via NCBI accession NOs: XM_017002869.2 (variant X1); NR_026665.1 (variant 3); NM_001779.2 (variant 1); NM_001144822.1 (variant 2). Amino acid sequences of CD58, in particular *Homo sapiens* (human) CD58, are, for example, available via NCBI accession NOs: XP_016858358.1 (isoform X1); NP_001138294.1 (isoform 2); NP_001770.1 (isoform 1). An example of a nucleotide sequence encoding *Homo sapiens* (human) CD58 is depicted in SEQ ID NO:11. An example of an amino acid sequence of *Homo sapiens* (human) CD58 is depicted in SEQ ID NO:12.

In principle, "expression" in the context of the invention is envisaged to mean both, gene expression, i.e. appearance of (primary) mRNA (transcription level), and protein expression, i.e. appearance of protein (translation level).

The appearance of (primary) mRNA can, for example, be measured/detected by in situ hybridization (ISH) techniques, for example by fluorescence ISH (FISH). Respective means and methods are known in the art and are, for example, described in Zhang (Chin. J. Cancer. Res. 23(2), 2011, 160-4.

Gene expression/appearance of (primary) mRNA, in particular CD58 gene expression/appearance of (primary) CD58 mRNA, can also be evaluated by using TruSeq® RNA sequencing (according to the manual of the distributor (Illumina®, Inc.)).

The appearance of protein can, for example, be measured/detected by IHC. Respective means and methods are known in the art and are, for example, described in Punnoose (loc cit.).

Protein expression/appearance of protein, in particular CD58 Protein expression, can also be measured/detected as described in Challa-Malladi loc. cit.

In general, means and methods for assessing CD58 expression and CD58 mutations are known in the art (see, for example, Challa-Malladi loc. cit.). Moreover, the skilled person can readily assess whether a given CD58 expression is "low" in accordance with the invention or whether there are (is) (a) CD58 mutation(s) in accordance with the invention. Furthermore, the skilled person can readily choose a suitable control in comparison to which a given CD58 expression is considered "lower" in accordance with the invention or in comparison to which it is considered that there are (is) (a) CD58 mutation(s) in accordance with the invention. In this context, the skilled person can, for example, also rely on Challa-Malladi (loc. cit.).

In the context of the invention, "low expression of CD58" means that CD58 is expressed at a substantially lower level, in particular as compared to a suitable control. In general, a "low expression of CD58" in accordance with the invention means that the CD58 expression is as low (e.g. ±10% or less, ±7.5% or less, ±5% or less, ±3% or less, ±2% or less, ±1% or less, or even ±0%) as the CD58 expression in a responder in accordance with the invention (i.e. a patient which responds to a treatment with obinutuzumab (in particular in combination with a chemotherapy, more particular in combination with a CHOP chemotherapy) by reaching an improved clinical outcome as compared to a treatment with rituximab (in particular in combination with a chemotherapy, more particular in combination with a CHOP chemotherapy); "patient defined herein") and/or lower than the expression of CD58 in a non-responder in accordance with the invention (i.e. a patient which responds to a treatment with obinutuzumab (in particular in combination with a chemotherapy, more particular in combination with a CHOP chemotherapy) by not reaching an improved clinical outcome as compared to the treatment with rituximab (in particular in combination with a chemotherapy, more particular in combination with a CHOP chemotherapy); non-"patient defined herein"). The skilled is readily able to assess when CD58 expression is "low" in this respect and to apply a suitable control. For example a control in this respect may be a common DLBCL population, more particular DLBCL patients which are not classified as pertaining to the subgroup of patients classified in accordance with the invention (non-"patient defined herein"). "Low expression of CD58" may be a CD58 expression lower than the median CD58 expression among a control group, e.g. among such above-mentioned control groups. For example, a "low expression of CD58" and a "lower level" of CD58 expression, respectively, in accordance with the invention may be a CD58 expression which is lower than the median CD58 expression among the observed GOYA patients.

As a unit of CD58 (gene) expression, the unit log2 (nRPKM), which is the normalized Reads Per Kilobase Million, may be used. Median CD58 expression using this unit among the GOYA patients is around 5.3. Accordingly, a "low expression of CD58" and a "lower level" of CD58 expression, respectively, in accordance with the invention may be a CD58 expression which is lower than the CD58 expression in a control (group of) patient(s) (see above) corresponding to the unit log2(nRPKM) 5.3 (median CD58 expression in the control (group of) patient(s)). In other words, the CD58 expression in a patient to be treated in accordance with the invention may be substantially lower than the CD58 expression in a control (group of) patient(s) corresponding to the unit log2(nRPKM) of 5.3. That is, the CD58 expression in a patient to be treated in accordance with the invention may be a CD58 expression that corresponds to a unit log2(nRPKM) ≤5.2, ≤5.1, ≤5.0, ≤4.5, ≤4.0, ≤3.5, ≤3.0, ≤2.5 or ≤2.0.

As mentioned above, CD58 is expressed on tumor cells and on the surface of B-cells. Accordingly, in one particular aspect, "low expression of CD58" and a "lower level" of CD58 expression, respectively, in accordance with the invention means that CD58 is expressed on tumor cells and/or B-cells at a level which is substantially lower than the CD58 expression on common DLBCL tumor cells and/or common DLBCL B-cells. "common DLBCL" in this context, for example, means that the tumor cells and B-cells, respectively, are derived from a non-responder in accordance with the invention, preferably from DLBCL tumor cells and DLBCL B-cells, respectively, derived from a DLBCL patient which is not classified as a patient defined herein.

For example, a "low expression of CD58" and a (substantially) "lower level" of CD58 expression, respectively, in accordance with the invention means that CD58 is expressed at a level which is at least 10% lower, at least 20% lower, at least 30% lower, at least 40% lower, at least 50% lower, at least 75% lower, or at least 100% lower, in particular as compared to the CD58 expression in a suitable control (e.g. common DLBCL patient/population; non-"patient defined herein"). This applies to both, gene expression and protein expression.

Mutations, in particular CD58 mutations can, for example, be identified by using the FoundationOne® Herne (FOH) panel (see, for example, He, Blood 127(24), 2017, 3004-14; see also the appended examples).

Examples of genetic mutations in CD58 which may be present (and detected) in a patient defined herein are short-variant mutations and/or copy-number variants.

The skilled person is readily able to choose an appropriate sample to be used when assessing/detecting CD58 expression or (a) CD58 mutation(s) in accordance with the invention (either as the test sample or as the control sample).

A particular example of a sample to be employed in the context of the invention (either as the test sample or as the control sample) for assessing/detecting whether there is a low CD58 expression is a sample (e.g. biopsy) of a (CD58-expressing) tumor and/or a sample (e.g. biopsy) which contains (CD58-expressing) B-cells.

A particular example of a sample to be employed in the context of the invention (either as the test sample or as the control sample) for assessing/detecting whether there are (is) (a) CD58 mutation(s) is a DNA sample.

In one aspect/embodiment of the invention (aspect/embodiment D), the patient defined herein (which is to be treated with obinutuzumab) is a patient with/suffering from strong-GCB DLBCL.

In accordance with the invention, a patient with/suffering from strong-GCB DLBCL can be identified by determining the (weighted) expression of (a set of genes comprising) one or more (preferably all) of the genes TNFRSF13B, LIMD1, IRF4, CREB3L2, PIM2, CYB5R2, RAB7L1, and CCDC50 (genes overexpressed in ABC DLBCL); and MME, SERPINA9, ASB13, MAML3, ITPKB, MYBL1, and S1PR2 (genes overexpressed in GCB DLBCL).

More particular, a patient with/suffering from strong-GCB DLBCL may be defined as a patient having a tumor with a certain (weighted) expression of (a set of genes comprising) one or more, preferably all, of the genes TNFRSF13B, LIMD1, IRF4, CREB3L2, PIM2, CYB5R2, RAB7L1, and CCDC50; and MME, SERPINA9, ASB13, MAML3, ITPKB, MYBL1, and S1PR2; and, optionally, one or more, preferably all, of the genes R3HDM1, WDR55, ISY1, UBXN4, and TRIM56 (housekeeping genes).

It is particularly envisaged in the context of this aspect/embodiment of the invention that the weighted gene expression is assessed.

In particular, when the Linear Predictor Score (LPS) resulting from the weighted expression of a set of genes disclosed herein is below a certain cutoff, i.e. substantially below the LPS cutoff usually allocated to GCB DLBCL (~<1900), the GCB DLBCL is regarded as "strong-GCB DLBCL". Likewise, when the weighted expression of a set of genes disclosed herein corresponds to the weighted expression of a set of genes disclosed herein from which an LPS below a certain cutoff results, i.e. an LPS substantially below the LPS cutoff usually allocated to GCB DLBCL (~<1900), the GCB DLBCL is regarded as "strong-GCB DLBCL". In accordance with the invention, examples of particular cutoffs, i.e. resulting LPS, that can be applied, i.e. that define "strong-GCB DLBCL", are cutoffs (about) ≤1200, (about) ≤1141, (about) ≤1100, (about) ≤756, (about) ≤750, (about) ≤749, (about) ≤745, (about) ≤725 or (about) ≤699. Preferred cutoffs are (about) ≤750, (about) ≤749 and (about) ≤725. Particularly preferred cutoffs are (about) ≤750 and (about) ≤725.

The set of genes to be employed in accordance with the invention, i.e. in accordance with the determination/identification/diagnosing of strong-GCB DLBCL, may further comprises one or more housekeeping genes, for example one or more (preferably all) of the housekeeping genes R3HDM1, WDR55, ISY1, UBXN4, and TRIM56.

The expression of the one or more of the other genes to be employed may be normalized to the expression of one or more housekeeping gene(s), e.g. housekeeping gene(s) as defined herein. The skilled person is readily able to normalize the expression of the one or more of these other genes (and of one or more other gene(s) that may be comprised in the set of genes to be employed in accordance with the invention) on the basis of one or more housekeeping genes, for example on the basis of the one or more housekeeping genes mentioned above. For example, at least 1, 2, 3, 4 or 5 (of these) housekeeping genes may be employed in this respect. For respective guidance, the skilled person can rely on, for example, Scott (2014 and 2015 loc. cit.).

In principle, also a set of genes comprising only a subset of the above-mentioned sets of genes may be employed in accordance with the invention. For example, such a subset may comprise at least 1, 2, 3, 4, 5, 6, 7, 8, 9, 10, 11, 12, 13, 14, 15, 16, 17, 18 or 19 of the above-mentioned entire set of genes. However, the more of these genes are assessed, the more it is preferred.

Examples of such subsets of genes that may be employed in accordance with the invention are subsets of genes that comprise at least 1, 2, 3, 4, 5, 6 or 7 of the genes TNFRSF13B, LIMD1, IRF4, CREB3L2, PIM2, CYB5R2, RAB7L1, and CCDC50), at least 1, 2, 3, 4, 5 or 6 of the genes MME, SERPINA9, ASB13, MAML3, ITPKB, MYBL1, and S1PR2, or at least 1, 2, 3, 4, 5, 6, 7, 8, 9, 10, 11, 12, 13, or 14 of the genes of these two subsets of genes. In principle, the higher numbers of genes are preferred.

It is also envisaged in the context of the invention that not only the particular sets of genes or subsets of genes as mentioned herein can be assessed in accordance with the invention; but also (sub)sets of genes which comprise one or more further genes (e.g. 2 or more, 3 or more, 4 or more, 5 or more, 6 or more, 7 or more, 8 or more, 9 or more, 10 or more, 20 or more, 30 or more, 40 or more, 50 or more, 60 or more, 70 or more, 80 or more, 90 or more, 100 or more, 150 or more, 170 or more, or 180 or more further genes). This/these further gene(s) may, for example, be one or more of the (about 180) genes known to separate/distinguish GCB and ABC (and unclassified) DLBCL on the basis of their (wheighted) expression (see, in particular, Lenz (N. Engl. J. Med. 359 (2), 2008, 2313-23) and also Geiss (Nature Biotechnology 26 (3), 2008, 317-25)).

For example, a set of genes to be assessed in accordance with the invention, may comprise (at least 1, 2, 3, 4, 5, 6, 7, 8, 9, 10, 11, 12, 13, 14, 15, 16, 17, 18 or 19 of) the genes of any of the particular sets of genes or subsets of genes mentioned above and one or more further genes (e.g. 2 or more, 3 or more, 4 or more, 5 or more, 6 or more, 7 or more, 8 or more, 9 or more, 10 or more, 20 or more, 30 or more, 40 or more, 50 or more, 60 or more, 70 or more, 80 or more, 90 or more, 100 or more, 150 or more, 170 or more, or 180 or more further genes), for example, of the (about 180) genes known to separate/distinguish GCB and ABC (and unclassified) DLBCL on the basis of their (wheighted) expression (cf. Lenz and Geiss, loc. cit.).

For example, one (or more) other gene(s) may be added to one of the above-described sets or subsets of genes, e.g. to one of the panels of 20, 15, 8 or 7 genes mentioned above, or one (or more) of the genes of one of the above-described sets or subsets of genes, e.g. of the panels of 20, 15, 8 or 7 genes mentioned above, may be replaced by one (or more) other gene(s).

A non-limiting, but preferred, example of another gene to be employed in accordance with aspect/embodiment D is the BLC2 gene.

An example of the means and methods which can be used to determine the expression, in particular weighted expression, of the above-mentioned genes in accordance with the invention is provided by NanoString (NanoString Technologies, Inc., Seattle, Wash., USA; see also Lenz (loc. cit.) and Geiss (loc. cit.)). A non-limiting particular example by which the (weighted) expression of the above-mentioned genes can be determined is the NanoString Research Use Only LST assay. Another example is the TruSeq® RNA tool (Illumina®, Inc.). Further examples are described in Wright (PNAS 100 (17), 2003, 9991-6). Also described in Wright (loc. cit.) is the general applicability of any suitable panel for (weighted) gene expression analyses.

In accordance with the mentioned examples of means and methods which can be used to determine the (weighted) expression, a patient with/suffering from strong-GCB DLBCL may also be defined as a patient having a tumor with a (wheighted) gene expression resulting in an LPS below the LPS usually allocated to GCB DLBCL (~<1900; see above for examples of respective cutoffs), wherein the LPS is derived from a NanoString LST, e.g. from the NanoString Research Use Only LST (NanoString Technologies, Inc., Seattle, Wash., USA), as the (weighted) gene expression of the genes in the Nanostring panel (or a tumor with a (weighted) gene expression which corresponds to such a (wheighted) gene expression). For example, the particular genes mentioned above may be in the Nanostring panel.

A patient with/suffering from strong-GCB DLBCL may also be defined as a patient having a tumor with a (wheighted) gene expression with/resulting in an LPS below the LPS usually allocated to GCB DLBCL (~<1900; see above for examples of respective cutoffs), wherein the LPS results from a COO classification by (weighted) gene-expression profiling (for example by using a NanoString LST as described herein) (or a tumor with a (weighted) gene expression which corresponds to such a (weighted) gene expression).

In principle, COO classification (e.g. into strong-, unclassified- and weak-GCB DCBCL), can be based on gene-expression profiling, in particular weighted gene-expression profiling, (e.g. using a NanoString LST (like, for example, the NanoString Research Use Only LST) (NanoString Technologies, Inc., Seattle, Wash., USA).

In principle, the meaning of "LPS" is known in the art and is accordingly understood by the skilled person in the context of the invention. In particular, the LPS in accordance with the invention is a continuous variable (weighted average for gene expression; e.g. of the genes mentioned herein, which may be in a Nanostring LST).

In the sum of the patients assessed in GOYA, the LPS has a range from −1138 to 4504. Normally, as mentioned above, the LPS is used to classify patients into COO subgroups GCB DLBCL, ABC DLBCL, and unclassified DLBCL (see above and Scott 2014 and 2015 loc. cit.). Default COO algorithm uses a bayesian approach with GCB/ABC classification based on ≥90% cutoff on likelihood of being GCB or ABC (unclassified works as a buffer).

More particular, the LPS in accordance with the invention is envisaged to be the weighted sum of the expression of the genes to be employed in the gene expression profiling (e.g. the above mentioned genes comprised in the mentioned (sub-)sets of genes). The weighted sum of gene expression can be calculated according to the following formula (Formula I):

$$LPS(X) = \Sigma_j a_j X_j,$$

wherein X stands for each sample, $X_j$ is the gene expression for gene j and $a_j$ is the coefficient for gene j. (see also Wright loc. cit.; in particular, the sections "*Gene Expression Data*" and "*Formulation of the DLBCL Subgroup Predictor*"; incorporated herein by reference)

In general, the person skilled in the art is able to determine the expression of genes, in particular the weighted expression of genes, in accordance with the teaching of the invention. Respective means and methods are known in the art and are, for example, described in Wright (loc. cit.), in particular, in the sections "*Gene Expression Data*" and "*Formulation of the DLBCL Subgroup Predictor*"; incorporated herein by reference. Wright (loc. cit.), for example, also outlines how the weighted gene expression algorithm can be used and how it can be transferred across gene expression platforms, like the NanoString LST and others. Comparable guidance is also provided in Lenz (loc. cit.).

In the context of the strong-GCB DLBCL classification in accordance with the invention and, in particular as described above, the following may further be considered:

Multivariate Cox regression and(/or) elastic net penalized regression (alpha=0.5) may be used to evaluate biomarker treatment effects. Simulations to identify the optimal cutoff, for example on the basis of the NanoString LST and the respective LPS, for treatment effect may be performed using cross validation and(/or) bootstrapping. Multiple testing adjustment may be done by estimating false-discovery rates (FDRs), for example using the Benjamini-Hochberg procedure (e.g. significance<5% FDR). Pathway enrichment analysis may be performed by gene-set enrichment, e.g. by using gene sets defined by MSigDB hallmarks and(/or) a curated FL somatic mutation hallmark gene set.

In particular an LPS cutoff (e.g. as described herein elsewhere) may be determined in (a) simulation analyses (analysis), preferably in (a) multivariate simulation analyses (analysis).

The robustness of an LPS cutoff (e.g. as described herein elsewhere) may be shown by bootstrap simulations.

Moreover, instead of using the specific weighted algorithm of LPS, e.g. from the NanoString LST, the 1st principal component from a principal component analysis of the results, for example, of another expression analysis panel (e.g. the TruSeq® RNA tool (Illumina®, Inc.)) may be applied, evaluating, for example the above-mentioned genes (e.g. one or more of the ~180 genes known to separate GCB and ABC) by gene expression. It was also shown in accordance with the invention that there is a very high correlation between the (NanoString LST-derived) LPS and the 1st principal component.

In one aspect/embodiment of the invention (aspect/embodiment E), the patient defined herein (which is to be treated with obinutuzumab) is a patient with BCL2 translocations and/or high BCL2 expression. Preferably, a BCL2 translocated patient with high BCL2 expression is envisaged in the context of this aspect/embodiment.

BCL2 (see also Zhang loc. cit.; Punnoose loc. cit.; lqbal, Clin Cancer Res 17(24), 2011, 7785-95; lqbal, JCO 24(6), 2006, 961-8; Hu, Blood 121(20), 2013, 4021-31; Johnson, JCO 30(28), 2012, 3452-67; Green, JCO 30(28), 2012, 3460-67) is commonly known to be an anti-apoptotic protein whose overexpression opposes mitochondrial apoptotic pathways. BCL2 is known to be expressed in tumors of DLBCL patients. Nucleotide sequences encoding BCL2 and amino acid sequences of BCL2, in particular *Homo sapiens* (human) BCL2, are well known in the art. Nucleotide sequences encoding BCL2, in particular *Homo sapiens* (human) BCL2, are, for example, available via NCBI accession NOs: XM_017025917.2 (variant X3); XM_011526135.3 (variant X2); XR_935248.3 (variant X1); NM_000657.2 (variant beta); NM_000633.2 (variant alpha). Amino acid sequences of BCL2, in particular *Homo sapiens* (human) BCL2, are, for example, available via NCBI accession NOs: XP_016881406.1 (isoform X2); XP_011524437.1 (isoform X1); NP_000648.2 (isoform beta); NP_000624.2 (isoform alpha). An example of a nucleotide sequence encoding *Homo sapiens* (human) BCL2 is depicted in SEQ ID NO:13. An example of an amino acid sequence of *Homo sapiens* (human) BCL2 is depicted in SEQ ID NO:14.

Was has been generally said herein above with respect to "expression", the measurement/detection of (primary) mRNA and the measurement/detection of protein applies here, mutatis mutandis.

In general, means and methods for measuring/detecting BCL2 expression and BCL2 translocations are known in the art and are, for example, described in Zhang (loc. cit.) and Puunoose (loc. cit.). Moreover, the skilled person can readily assess whether a given BCL2 expression is "high" in accordance with the invention or whether there are (is) (a) BCL2 translocation(s) in accordance with the invention. Furthermore, the skilled person can readily choose a suitable control in comparison to which a given BCL2 expression is considered "higher" in accordance with the invention or incomparison to which it is considered that there are (is) (a) BCL2 translocation(s) in accordance with the invention. In this context, the skilled person can, for example, also rely on Zhang (loc. cit.) and Puunoose (loc. cit.).

BCL2 expression can, for example, be assessed by a Ventana immunohistochemistry (IHC) assay, for example by the Ventana investigational-use IHC assay (BCL2 antibody clone 124) (by attending to the manucal of the supplier). For example, high BCL2 expression can be defined in this context as moderate or strong staining in ≥50% tumor cells (see below for further details).

BCL2 protein expression/appearance of BCL2 protein can also be measured/detected as described in Punnoose (loc. cit.), Iqbal (2011 and 2006 loc. cit), Hu (loc. cit.), Johnson (loc. cit), Green (loc. cit.). Gene expression/appearance of (primary) mRNA, in particular BCL2 gene expression/appearance of (primary) BCL2 mRNA can, for example, be evaluated as described in Zhang (loc. cit.) or by using TruSeq® RNA sequencing ((Illumina®, Inc.) according to the manual of the distributor).

In the context of the invention, "high expression of BCL2" means that BCL2 is expressed at a substantially higher level, in particular as compared to a suitable control. In general, a "high expression of BCL2" in accordance with the invention means that the BCL2 expression is as high (e.g. ±10% or less, ±7.5% or less, ±5% or less, ±3% or less, ±2% or less, ±1% or less or even ±0%) as the BCL2 expression in a responder in accordance with the invention (i.e. a patient which responds to a treatment with obinutuzumab (in particular in combination with a chemotherapy, more particular in combination with a CHOP chemotherapy) by reaching an improved clinical outcome as compared to a treatment with rituximab (in particular in combination with a chemotherapy, more particular in combination with a CHOP chemotherapy); "patient defined herein") and/or higher than the expression of BCL2 in a non-responder in accordance with the invention (i.e. a patient which responds to a treatment with obinutuzumab (in particular in combination with a chemotherapy, more particular in combination with a CHOP chemotherapy) by not reaching an improved clinical outcome as compared to the treatment with rituximab (in particular in combination with a chemotherapy, more particular in combination with a CHOP chemotherapy); non-"patient defined herein"). The skilled is readily able to assess when BCL2 expression is "high" in this respect and to apply a suitable control. For example, a control in this respect may be a common DLBCL population, more particular DLBCL patients which are not classified as pertaining to the subgroup of patients classified in accordance with the invention (non-"patient defined herein"). "High expression of BCL2" may be a BCL2 expression higher than the median BCL2 expression among a control group, e.g. among such above-mentioned control groups. For example, a "high expression of BCL2" and a "higher level" of BCL2 expression, respectively, in accordance with the invention may be a BCL2 expression which is higher than the median BCL2 expression among the patients assessed in GOYA.

An example of a control, on the basis of which it can be considered in the context of the invention whether BCL2 expression is "high", is normal, i.e. non-tumor, tissue, more particular normal, i.e. non-tumor, lymphatic tissue. The tissue may be from a DLBCL patient. For example, it may be from the DLBCL patient to be treated. However, in principle, the tissue may also be of a normal/healthy subject.

A preferred example of a control, on the basis of which it can be considered in the context of the invention whether BCL2 expression is "high", is tumor tissue, more particular lymphatic tumor tissue form a non-responder in accordance with the invention (non-"patient defined herein"). It is preferred that the tissue is from a non-responding DLBCL patient (non-"patient defined herein" which is a DLBCL patient).

BCL2 expression is considered "high" if, for example, ≥30%, ≥40%, ≥50% or ≥60% of the tumor cells express BCL2 (for example show BCL2 staining in an IHC assay), in particular show moderate to strong BCL2 expression (for example show moderate to strong BCL2 staining in an IHC assay).

It is preferred in the context of the invention that BCL2 expression, in particular "high" BCL2 expression, incorporates both, the percentage of tumor cells which express BCL2 and the intensity of BCL2 expression in these cells.

When assessing whether a given BCL2 expression is "high" in accordance with the invention, the skilled person can also rely on Iqbal (2011 and 2006 loc. cit), Hu (loc. cit.), Johnson (loc. cit.) and Green (loc. cit).

More general, a "high expression of BCL2" and a (substantially) "higher level" of BCL2 expression, respectively, in accordance with the invention means that BCL2 is expressed at a level which is at least 10% higher, at least 20% higher, at least 30% higher, at least 40% higher, at least 50% higher, at least 75% higher, or at least 100% higher, in particular as compared to the BCL2 expression in a suitable control (e.g. common DLBCL patient/population; non-"patient defined herein"). This applies to both, gene expression and protein expression.

The meaning of "(a) BCL2 translocation(s)" is well known in the art. Typically, a "BCL2 translocation" is a gene fusion between BCL2 and IgH (involving chromosoms 14 and 18). BCL2 translocation(s) are, for example, described in Zhang (loc. cit.)

BCL2 translocations can, for example, be assessed/detected by using the BCL2 Dual Color Break Apart technology (Vysis, Abbott Molecular), in particular by using Vysis LSI Dual Color Break Apart FISH Probes, (e.g. with a (FISH) cutoff at 5% (typically used) or 50%); by attending to the manual of the supplier. BCL2 translocations can also be assessed/detected with the Foundation Medicine next-generation sequencing assay, FoundationOne® Heme (by attending to the manucal of the supplier; see also He loc. cit.). Means and methods for assessing/detecting BCL2 translocations are known in the art and are, for example, described in Zhang loc. cit.) and He (loc. cit.).

The skilled person is readily able to choose an appropriate sample to be used when assessing/detecting (a) BCL2 translocation (s) or BCL2 expression in accordance with the invention (either as the test sample or as the control sample).

A particular example of a sample to be employed in the context of the invention (either as the test sample or as the control sample) for assessing/detecting whether there is a high BCL2 expression is a sample (e.g. biopsy) of a (BCL2-expressing) tumor.

A particular example of a sample to be employed in the context of the invention (either as the test sample or as the control sample) for assessing/detecting whether there are (is) BCL2 translocation(s) is a DNA sample.

In one aspect/embodiment of the invention (aspect/embodiment F), the patient defined herein (which is to be treated with obinutuzumab) is defined by a combination/an intersection of any 2, any 3, any 4 or any 5 of the patient definitions referred to in aspects/embodiments A, B, C, D and E supra. That is, the patient may be defined by a combination/an intersection of the patient definitions referred to in aspects/embodiments A and B; A and C; A and D; A and E; B and C; B and D, B and E; C and D; C and E; A, B and C; A, C and D; A, D and E; A, B and D; A, B and E; A, C and E; B, C and D; B, C and E; B, D and E; C, D and E; A, B, C and D; A, C, D and E; B, C, D and E; and A, B, D and E. Preferred are combinations/intersections which comprise the definitions according to aspects/embodiments D and E.

In one aspect/embodiment of the invention (aspect/embodiment G), the patient defined herein (which is to be treated with obinutuzumab) is defined by a combination/an intersection of the patient definitions referred to in aspects/embodiments D and E (or A, D and E), supra. That is, the patient defined herein in accordance with this aspect/embodiment is a patient (i) with/suffering from strong-GCB DLBCL; and (ii) with BCL2 translocations and/or high BCL2 expression. This combination/intersection of patient definitions defines a preferred patient defined herein.

In general, as used in the context of the present invention, a non-limiting example of a "control" is preferably a "non-responder" control, for example a sample/cell/tissue obtained from one or more patients that do not suffer from the particular DLBCL as defined herein (non-"patient defined herein") and that are known to be not advantageously responsive to obinutuzumab (in particular in combination with a chemotherapy, more particular in combination with a CHOP chemotherapy) as compared to rituximab (in particular in combination with a chemotherapy, more particular in combination with a CHOP chemotherapy) in accordance with the invention. Another example for a "non-responder" control is a cell line/sample/cell/tissue that shows no improved response to obinutuzumab (in particular in combination with a chemotherapy, more particular in combination with a CHOP chemotherapy) as compared to rituximab (in particular in combination with a chemotherapy, more particular in combination with a CHOP chemotherapy) in an ex-vivo test. Another non-limiting example of a "control" is an "internal standard", for example purified or synthetically produced proteins, peptides, DNA and/or RNA, or a mixture thereof, where the amount of each protein/peptide/DNA/RNA is gauged by using the "non-responder" control described herein.

In principle, the patient to be treated in the context of the invention is envisaged to be a DLBCL patient. In other words, the patient is a patient with/suffering from DLBCL. Accordingly, it is particularly envisaged that also the patient defined with respect to any of the aspects/embodiments A, B, C, D, E, F, G, supra, is a DLBCL patient and a patient with/suffering from DLBCL, respectively. However, it is not necessarily required that a given patient is diagnosed as being a DLBCL patient, for example prior to (or after) the determination/identification/diagnosis of being a patient as defined herein, in particular as defined in one (or more) of the aspects/embodiments A to G, supra. It is, however, preferred that the patient to be treated in accordance with the invention is, in a first step, diagnosed as being a DLBCL patient, or at least as being a Lymphoma patient, and, in a second step, determined/identified/diagnosed as being a patient defined herein, in particular a patient as defined in one (or more) of the aspects/embodiments A to G, supra. In principle, in accordance with the invention, a given patient may, in a first step, also be determined/identified/diagnosed as being a patient defined herein, and, in a second step, diagnosed as being a DLBCL patient, or at least as being a Lymphoma patient. However, the latter option is less preferred and, as mentioned, the (foregoing or subsequent) step of diagnosing whether the patient to be treated is a (DLBC)L patient may also be omitted.

A non-limiting example of a way how the attending physician would choose whether a given patient is to be treated in accordance with the invention is provided in the following:

From a patient, for example with an abnormality raising the clinical suspicion of lymphoma (e.g. enlarged lymph nodes), a (tumor) sample (e.g. (tumor) biopsy) may be taken. The (tumor) sample may be diagnosed as (DLBC)L positive (e.g. by a pathologist). This may be one of the 2 two steps mentioned above. As mentioned, this step may be omitted.

From a (remainder of the) (tumor) sample (e.g. (tumor) tissue/biopsy), or from another (tumor) sample of the same or another patient, or from another tumor of the same or another patient, protein, RNA (e.g. (primary) mRNA) and/or DNA may be extracted. The patient defined herein may then be determined/identified/diagnosed, i.e. the biomarker analysis/analyses in accordance with the invention may then be performed, with the sampled protein, RNA (e.g. (primary) mRNA) and/or DNA. For example, the samples may be analyzed with the weighted gene expression assay (e.g. by using the NanoString LST) to obtain the LPS, tested for (a) genetic mutation(s) in CD58 and/or for low expression of CD58 and/or tested for BCL2 translocations and/or for high BCL2 expression. The results of the analysis/analyses then allow for classifying the patient into the DLBCL subgroups defined in accordance with the invention. In other words, results of the analysis/analyses then allow for classifying whether the patient is a "patient defined herein". This may be the other one of the 2 two steps mentioned above (i.e. the obligatory step).

Non-limiting examples of the biomarker analysis/analyses may be employed in accordance with the invention according to the following:

A tumor sample, for example a diagnostic tumor sample, (e.g. tissue biopsy), for example formalin-fixed and(/or) paraffin-embedded, may be taken from a patient. RNA (or protein or DNA) may be extracted and gene expression may by analysed for strong-GCB classification, CD58 translocation/low expression and/or BCL2 mutation(s)/low expression. DNA may be extracted to evaluate (a) CD58 mutation(s). Tissue sections, in particular tumour tissue sections, may be cut and embedded, e.g. for IHC and/or (F)ISH analyses.

As mentioned, it is envisaged in the context of the invention to use obinutuzumab, or a fuctional equivalent of obinutuzumab, for treating the patient defined herein.

Obinutuzumab itself is well known in the art and is, for example, described in EP-B1 2380910 and WO 2005/044859. See below for further details as to obinutuzumab itself.

Also the meaning of "functional equivalent of obinutuzumab" is clear to the skilled person. In particular, the term "functional equivalent of obinutuzumab" refers to an antibody, in particular to a humanized Type II anti-CD20 antibody, which is more suitable for treating (in particular in combination with a chemotherapy, more particular in combination with a CHOP chemotherapy) the patient defined herein than rituximab (in particular in combination with a chemotherapy, more particular in combination with a CHOP chemotherapy). In other words, this term refers to an antibody, in particular a human Type II anti-CD20 antibody, with features and mode of actions (MOAs) which render the antibody capable of treating a patient defined herein so that it responses by reaching an improved clinical outcome as compared to a treatment with rituximab. More particular, the term "functional equivalent of obinutuzumab" refers to an antibody, in particular an Type II anti-CD20 antibody, which has the same features and biological functions as obinutuzumab itself, in particular the same biological functions as obinutuzumab itself which render the antibody to be more suitable for treating the patient defined herein than rituximab.

Examples of the most relevant features and MOAs of an equivalent of obinutuzumab in accordance with the invention (and of obinutuzumab itself) are defined herein elsewhere. They can readily be determined by the skilled person.

It is, in principle, envisaged in the context of the invention that the term "functional equivalent of obinutuzumab" also covers biosimilars of obinutuzumab. In particular, it is envisaged that the meaning of that term also covers any biosimilar of obinutuzumab which is more suitable for treating the patient defined herein than rituximab. In other words, the "functional equivalent of obinutuzumab" may be a biosimilar of obinutuzumab which is capable of treating a patient defined herein so that it responses by reaching an improved clinical outcome as compared to a treatment with rituximab (in particular in combination with a chemotherapy, more particular in combination with a CHOP chemotherapy).

In general, the meaning of "biosimilar" is well-known in the art. In this context, a "biosimilar" is known to be a biologic medical product which is almost an identical copy of an original biologic medical product and is also known as follow-on biologic or subsequent entry biologic. Biosimilars are officially approved versions of original "innovator" products. In this context, reference is, for example, made to the EMEA guideline on Similar Biological Medicine Products (CHMP/437/04 London, 2005).

In the context of the invention, obinutuzumab, in particular the functional equivalent of obinutuzumab, is envisaged to be an antibody, in particular a humanized Type II anti-CD20 antibody, comprising (a) a heavy chain variable region as depicted in SEQ ID NO:1 and a light chain variable region as depicted in SEQ ID NO:2 (this light chain variable region is also known as KV1 light chain variable region; "KV1" stands for the humanized light chain variable region of the murine B-Ly1 monoclonal antibody; see EP-B1 2380910);

(b) a heavy chain variable region having the specificity determining residues of the heavy chain variable region of (a) and a light chain variable region having the specifity determining residues of the light chain variable region of (a); or (c) a heavy chain variable region that is encoded by a nucleic acid sequence which is at least 80%, at least 85%, at least 90%, at least 95%, at least 98% or at least 99% identical to SEQ ID NO: 3 and a light chain variable region that is encoded by a nucleic acid sequence which is at least 80%, at least 85%, at least 90%, at least 95%, at least 98% or at least 99% identical to SEQ ID NO: 4 (the higher values are preferred).

It is preferred that obinutuzumab, in particular the functional equivalent of obinutuzumab to be employed in the context of the invention is a monoclonal antibody, in particular a monoclonal humanized Type II anti-CD20 antibody.

It is particularly preferred that the antibody to be employed in accordance with the invention is a Type II anti-CD20 antibody, in particular a humanized Type II anti-CD20 monoclonal antibody, or, preferably and, an antibody which comprises a glycoengineered Fc region, in particular a glycoengineered Fc region as defined herein below. It is further preferred that, in accordance with the invention, such an antibody, or any other antibody to be employed in accordance with the invention, shows substantially higher levels of ADCC activity, in particular as compared to a comparable Type I anti-CD20 antibody and/or as compared to a non-glycoengineered antibody (e.g. rituximab).

The meaning of "Type II" anti-CD20 antibody is well known in the art. In general, anti-CD20 monoclonal antibodies fall into two distinct categories based on their mechanism of action in eradicating lymphoma cells. Type I anti-CD20 antibodies primarily utilize complement to kill target cells, while Type II antibodies operate by different mechanisms, primarily apoptosis. Rituximab and 1 F5 are examples of Type I anti-CD20 antibodies, whereas B 1 is an example of a Type II antibody. See, e.g., Cragg (Blood 103(7), 2004, 2738-2743); Teeling (Blood 104(6), 2004, 1793-1800), the entire contents of which are hereby incorporated by reference. Also obinutuzumab itself is a Type II antibody. See, e.g. EP-B1 2380910 and WO 2005/044859, the entire contents of which are hereby incorporated by reference.

The skilled person knows, but is at least readily able to determine, the relevant specificity determining residues of the heavy and light chain variable regions of obinutuzumab. As to respective guidance, the skilled person can, for example, rely on EP-B1 2380910 and WO 2005/044859.

In one aspect, obinutuzumab/the functional equivalent of obinutuzumab as employed in the context of the invention, in particular as defined in (b) and (c), supra, is envisaged to have, inter alia, one or more of the following features:
(i) capability of inducing higher levels of apoptosis when incubated with CD20-positive human cells relative to a control under identical conditions using rituximab;
(ii) capability of causing an increased CD20$^+$ tumor B-cell killing as compared to rituximab;
(iii) capability of causing an increased direct cell death as compared to rituximab (without being bound by theory, this is due to an alternative binding geometry (e.g. elbow hinge-modification));
(iv) capability of causing a decreased complement-dependent cytotoxicity (CDC) as compared to rituximab (without being bound by theory, this is due to an alternative binding geometry (e.g. elbow hinge-modification));
(v) capability of causing an increased antibody-dependent cellular cytotoxicity (ADCC) as compared to rituximab (without being bound by theory, this is due to glycoengineered Fc region);
(vi) capability of causing an increased antibody-dependent cellular phagocytosis (ADCP) as compared to rituximab (without being bound by theory, this is due to glycoengineered Fc region);
(vii) an increased affinity for FcγRIII receptors as compared to rituximab (without being bound by theory, this is due to glycoengineered Fc region);
(viii) capabilitiy to trigger, upon binding to CD20, less internalization of surface CD20 as compared to rituximab.

In another aspect, obinutuzumab/the functional equivalent of obinutuzumab as employed in the context of the invention, in particular as defined in (b) and (c), supra, is envisaged to show, inter alia, one ore more of the following MOAs:
(i) capability of inducing higher levels of apoptosis when incubated with CD20-positive human cells relative to a control under identical conditions using rituximab;
(iii) capability of causing an increased direct cell death as compared to rituximab (without being bound by theory, this is due to an alternative binding geometry (e.g. elbow hinge-modification));
(iv) capability of causing a decreased complement-dependent cytotoxicity (CDC) as compared to rituximab (without being bound by theory, this is due to an alternative binding geometry (e.g. elbow hinge-modification));
(v) capability of causing an increased antibody-dependent cellular cytotoxicity (ADCC) as compared to rituximab (without being bound by theory, this is due to glycoengineered Fc region);
(vi) capability of causing an increased antibody-dependent cellular phagocytosis (ADCP) as compared to rituximab (without being bound by theory, this is due to glycoengineered Fc region);
(vii) an increased affinity for FcγRIII receptors as compared to rituximab (without being bound by theory, this is due to glycoengineered Fc region);
(viii) capability to trigger, upon binding to CD20, less internalization of surface CD20 as compared to rituximab.

Means and methods which can be used to determine the relevant features of an antibody to be employed in accordance with the invention (e.g. biological functions, MOAs) are well-known in the art and can readily be applied by the skilled person.

Means and methods which can be used to determine the level of apoptosis, in particular whether a given antibody is capable of inducing higher levels of apoptosis when incubated with CD20-positive human cells relative to a control under identical conditions using rituximab, are known in the art and are, for example, described in EP-B1 2380910 and WO 2005/044859.

A "higher level of apoptosis" in accordance with the invention means, for example, at least 1.2-fold higher, at least 1.5-fold higher, at least 2-fold higher, at least 3-fold higher, at least 4-fold higher, at least 5-fold higher, or at least 10-fold higher as compared to the level of apoptosis resulting from a comparable application of rituximab.

Means and methods which can be used to determine CD20$^+$ tumor B-cell killing, in particular whether there is an increased CD20$^+$ tumor B-cell killing as compared to rituximab, are known in the art and are, for example, disclosed in EP-B1 2380910 and WO 2005/044859.

In accordance with the invention, CD20$^+$ tumor B-cell killing is "increased", if it is, for example, at least 1.2-fold higher, at least 1.5-fold higher, at least 2-fold higher, at least 3-fold higher, at least 4-fold higher, at least 5-fold higher, or at least 10-fold higher as compared to CD20$^+$ tumor B-cell killing resulting from a comparable application of rituximab.

Means and methods which can be used to determine direct cell death, in particular whether there is an increased direct cell death as compared to rituximab, are known in the art and are, for example, disclosed in EP-B1 2380910 and WO 2005/044859.

In accordance with the invention, direct cell death is "increased", if it is at least 1.2-fold higher, at least 1.5-fold higher, at least 2-fold higher, at least 3-fold higher, at least 4-fold higher, at least 5-fold higher or at least 10-fold higher as compared to direct cell death resulting from a comparable application of rituximab.

Means and methods which can be used to determine CDC, in particular whether there is a decreased CDC as compared to rituximab, are known in the art and are, for example, disclosed in Herter (loc. cit.), Mossner (loc. cit.), EP-B1 238090, WO 2005/044859, WO 2015/067586 and WO 2016/207312.

In accordance with the invention, CDC is "decreased", if it is, for example, at least 1.2-fold lower, at least 1.5-fold lower, at least 2-fold lower, at least 3-fold lower, at least 4-fold lower, at least 5-fold lower, or at least 10-fold lower as compared to the CDC resulting from a comparable application of rituximab.

The term "complement-dependent cytotoxicity (CDC)" refers to lysis of human tumor target cells by the antibody to be employed according to the invention in the presence of complement. CDC is measured preferably by the treatment of a preparation of CD20 expressing cells with an anti-CD20 antibody to be employed according to the invention in the presence of complement. CDC is found if the antibody induces, for example at a concentration of 100 nM, the lysis (cell death) of, for example, 20%, or more of the tumor cells after, for example, 4 hours. The assay is performed preferably with $^{51}$Cr or Eu labeled tumor cells and measurement of released $^{51}$Cr or Eu. Controls include the incubation of the tumor target cells with complement but with rituximab and, optionally, without the antibody.

The skilled person is readily able to adapt this particular example of a CDC assay so as to be able to test whether the CDC activity is decreased upon the application of an antibody to be used in accordance with the invention as compared to the application of rituximab, as the case may be.

Means and methods which can be used to determine ADCC, in particular whether there is an increased ADCC as compared to rituximab, are known in the art and are, for example, disclosed in Herter (loc. cit.), Mossner (loc. cit.), Tobinai (Adv. Ther. 34, 2017, 324-56), EP-B1 2380910, WO 2005/044859, WO 2015/067596 and WO 2016/207312.

In accordance with the invention, ADCC, more generally, is "increased", if it is, for example, at least 1.2-fold higher, at least 1.5-fold higher, at least 2-fold higher, at least 3-fold higher, at least 4-fold higher, at least 5-fold higher, or at least 10-fold higher as compared to the ADCC resulting from a comparable application of rituximab.

One, non-limiting, accepted in vitro ADCC assay is as follows:
1) the assay uses target cells that are known to express the target antigen recognized by the antigen-binding region of the antibody (CD20);
2) the assay uses human peripheral blood mononuclear cells (PBMCs), isolated from blood of a randomly chosen healthy donor, as effector cells;
3) the assay is carried out according to the following protocol:
   i) the PBMCs are isolated using standard density centrifugation procedures and are suspended at $5 \times 10^6$ cells/ml in RPMI cell culture medium;
   ii) the target cells are grown by standard tissue culture methods, harvested from the exponential growth phase with a viability higher than 90%, washed in RPMI cell culture medium, labeled with 100 micro-Curies of $^{51}$Cr, washed twice with cell culture medium, and resuspended in cell culture medium at a density of $10^5$ cells/ml;
   iii) 100 microliters of the final target cell suspension above are transferred to each well of a 96-well microtiter plate;
   iv) the antibody is serially-diluted from 4000 ng/ml to 0.04 ng/ml in cell culture medium and 50 microliters of the resulting antibody solutions are added to the target cells in the 96-well microtiter plate, testing in triplicate various antibody concentrations covering the whole concentration range above;
   v) for the maximum release (MR) controls, 3 additional wells in the plate containing the labeled target cells receive 50 microliters of a 2% (VN) aqueous solution of non-ionic detergent (Nonidet, Sigma, St. Louis), instead of the antibody solution (point iv above);
   vi) for the spontaneous release (SR) controls, 3 additional wells in the plate containing the labeled target cells receive 50 microliters of RPMI cell culture medium instead of the antibody solution (point iv above);
   vii) the 96-well microtiter plate is then centrifuged at 50×g for 1 minute and incubated for 1 hour at 4° C.;
   viii) 50 microliters of the PBMC suspension (point i above) are added to each well to yield an effector:target cell ratio of 25:1 and the plates are placed in an incubator under 5% $CO_2$ atmosphere at 37° C. for 4 hours;
   ix) the cell-free supernatant from each well is harvested and the experimentally released radioactivity (ER) is quantified using a gamma counter;
   x) the percentage of specific lysis is calculated for each antibody concentration according to the formula (ER−MR)/(MR−SR)×100, where ER is the average radioactivity quantified (see point ix above) for that antibody concentration, MR is the average radioactivity quantified (see point ix above) for the MR controls (see point v above), and SR is the average radioactivity quantified (see point ix above) for the SR controls (see point vi above);
4) "increased ADCC" is defined as either an increase in the maximum percentage of specific lysis observed within the antibody concentration range tested above, and/or a reduction in the concentration of antibody required to achieve one half of the maximum percentage of specific lysis observed within the antibody concentration range tested above. The increase in ADCC is relative to the ADCC, measured with the above assay, mediated by the same antibody, produced by the same type of host cells, using the same standard production, purification, formulation and storage methods, which are known to those skilled in the art, but that has not been produced by host cells engineered to overexpress GnTIII.

The skilled person is readily able to adapt this particular example of an ADCC assay so as to be able to test whether the ADCC activity is increased upon the application of an antibody to be used in accordance with the invention as compared to the application of rituximab, as the case may be.

Means and methods which can be used to determine ADCP in particular whether there is an increased ADCP as compared to rituximab, are known in the art and are, for example, disclosed in Herter (loc. cit.) and Mossner (loc. cit.).

In accordance with the invention, ADCP is "increased", if it is, for example, at least 1.2-fold higher, at least 1.5-fold higher, at least 2-fold higher, at least 3-fold higher, at least 4-fold higher, at least 5-fold higher, or at least 10-fold higher as compared to the ADCP resulting from a comparable application of rituximab.

Means and methods which can be used to determine the affinity for FcγRIII receptors, in particular whether there is an increased affinity for FcγRIII receptors as compared to rituximab, are known in the art and are, for example, disclosed in Tobinai (loc. cit.)

In accordance with the invention, the affinity for FcγRIII receptors is "increased", if it is, for example, at least 1.2-fold higher, at least 1.5-fold higher, at least 2-fold higher, at least 3-fold higher, at least 4-fold higher, at least 5-fold higher, or at least 10-fold higher as compared to the the affinity for FcγRIII receptors resulting from a comparable application of rituximab.

Means and methods which can be used to determine the capability to trigger internalization of surface CD20 (upon binding to an anti-CD20 antibody), in particular whether there is the capability to trigger less internalization of surface CD20 (when binding to obinutuzumab) as compared to rituximab, are known in the art and are, for example, disclosed in Lim (Blood 118(9), 2011, 2530-40).

In accordance with the invention, internalization of surface CD20 is "less", if it is, for example, at least 1.2-fold lower, at least 1.5-fold lower, at least 2-fold lower, at least 3-fold lower, at least 4-fold lower, at least 5-fold lower, or at least 10-fold lower as compared to the capability to trigger surface CD20 internalization resulting from a comparable application of rituximab.

As mentioned, it is preferred in the context of the invention that obinutuzumab/the functional equivalent of obinutuzumab to be employed in the context of the invention comprises a glycoengineered Fc region. In this context, reference is also made to EP-B1 2380910 and WO 2005/044859; the entire content of which is incorporated herewith by reference.

It is particularly preferred in the context of the invention that the Fc-region of the antibody to be employed is glycoengineered so that the antibody has one or more of the features and MOAs, respectively, referred to above, more particular in sections (v), (vi) and (vii), supra. The feature/MOA of section (v) is most preferred in this respect (increase in ADCC).

Obinutuzumab/the functional equivalent of obinutuzumab to be employed in the context of the invention may have an increase in the fraction of non-fucosylated oligosaccharides attached to said glycoengineered Fc region.

Obinutuzumab/the functional equivalent of obinutuzumab to be employed in the context of the invention may have an increase in the fraction of bisected, non-fucosylated oligosaccharides attached to said glycoengineered Fc region.

Obinutuzumab/the functional equivalent of obinutuzumab to be employed in the context of the invention may have significantly higher levels of binding to human FcγRIII receptors relative to the non-glycoengineered antibody, and/or relative to rituximab.

As mentioned, it is preferred in the context of the invention that obinutuzumab/the functional equivalent of obinutuzumab to be employed in the context of the invention, in particular as defined in (b) and (c), supra, exhibits significantly higher levels of ADCC activity, in particular relative to the non-glycoengineered antibody, and/or relative to rituximab. Without being bound by theory, the significantly higher levels of ADCC activity result from the glycoengineered Fc region (see above).

The person skilled in the art is readily able to glycoengineer the Fc-region of an antibody, so as to achieve an antibody to be employed in accordance with the invention, e.g., as mentioned above and in a manner to retrieve the relevant feature(s)/MOA(s). Moreover, the skilled person is readily able to deduce what an increase in the fraction of non-fucosylated oligosaccharides and an increase in the fraction of bisected non-fucosylated oligosaccharides in accordance with the present invention is. In this context, the skilled person can, inter alia, rely on the guidance provided by EP-B1 2380910 and WO 2005/044859; the contents of which are incorporated herewith by reference. Non-limiting examples of such increases are increases of at least 1.2-fold, at least 1.5-fold, at least 2-fold, at least 3-fold, at least 4-fold, at least 5-fold or at least 10-fold (relative to the non-glycoengineered antibody).

In accordance with the present invention, the terms "identity" or "identical" or "percent identity" or "percentage identity" or "sequence identity" in the context of two (or more) nucleic acid sequences refer to two (or more) sequences or subsequences that are the same, or that have a specified percentage of nucleotides that are the same (preferably at least 80% identity, more preferably at least 85%, 90%, 95%, 96%, 97% or 98% identity, most preferably at least 99% identity), when compared and aligned for maximum correspondence over a window of comparison, or over a designated region as measured using a sequence comparison algorithm as known in the art, or by manual alignment and visual inspection. Sequences having, for example, 80% to 90% or greater sequence identity may be considered to be substantially identical. Such a definition also applies to the complement of a test sequence. The described identity may exist over a region that is at least about 15 to 25 nucleotides in length, over a region that is at least about 50 to 100 nucleotides in length or over a region that is at least about 800 to 1200 nucleotides in length (or over the entire length of the sequence). Those of skill in the art will know how to determine percent identity between/among sequences using, for example, algorithms such as those based on CLUSTALW computer program (Thompson Nucl. Acids Res. 2 (1994), 4673-4680) or FASTDB (Brutlag Comp. App. Biosci. 6 (1990), 237-245), as known in the art.

Although the FASTDB algorithm typically does not consider internal non-matching deletions or additions in sequences, i.e., gaps, in its calculation, this can be corrected manually to avoid an overestimation of the % identity. CLUSTALW, however, does take sequence gaps into account in its identity calculations. Also available to those having skill in this art are the BLAST and BLAST 2.0 algorithms (Altschul, (1997) Nucl. Acids Res. 25:3389-3402; Altschul (1993) J. Mol. Evol. 36:290-300; Altschul (1990) J. Mol. Biol. 215:403-410). The BLASTN program for nucleic acid sequences uses as defaults a word length (W) of 11, an expectation (E) of 10, M=5, N=4, and a comparison of both strands. The BLOSUM62 scoring matrix (Henikoff (1989) PNAS 89:10915) uses alignments (B) of 50, expectation (E) of 10, M=5, N=4, and a comparison of both strands.

In order to determine whether a nucleotide residue in a nucleic acid sequence corresponds to a certain position in a given nucleotide sequence, the skilled person can use means and methods well-known in the art, e.g., alignments, either manually or by using computer programs such as those mentioned herein. For example, BLAST 2.0, which stands for Basic Local Alignment Search Tool BLAST (Altschul (1997), loc. cit.; Altschul (1993), loc. cit.; Altschul (1990), loc. cit.), can be used to search for local sequence alignments. BLAST, as discussed above, produces alignments of nucleotide sequences to determine sequence similarity. Because of the local nature of the alignments, BLAST is especially useful in determining exact matches or in identifying similar sequences. The fundamental unit of BLAST algorithm output is the High-scoring Segment Pair (HSP). An HSP consists of two sequence fragments of arbitrary but equal lengths whose alignment is locally maximal and for which the alignment score meets or exceeds a threshold or cut-off score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper limit of the expected frequency of chance occurrence of an HSP (or set of HSPs) within the context of the entire database search. Any database sequence whose match satisfies E is reported in the program output.

Analogous computer techniques using BLAST (Altschul (1997), loc. cit.; Altschul (1993), loc. cit.; Altschul (1990), loc. cit.) are used to search for identical or related molecules in nucleotide databases such as GenBank or EMBL. This analysis is much faster than multiple membrane-based hybridizations. In addition, the sensitivity of the computer search can be modified to determine whether any particular match is categorized as exact or similar. The basis of the search is the product score which is defined as:

$$\frac{\% \text{ sequence identity} \times \% \text{ maximum BLAST score}}{100}$$

and it takes into account both the degree of similarity between two sequences and the length of the sequence match. For example, with a product score of 40, the match will be exact within a 1-2% error; and at 70, the match will be exact. Similar molecules are usually identified by selecting those which show product scores between 15 and 40, although lower scores may identify related molecules. Another example for a program capable of generating sequence alignments is the CLUSTALW computer program (Thompson (1994) Nucl. Acids Res. 2:4673-4680) or FASTDB (Brutlag (1990) Comp. App. Biosci. 6:237-245), as known in the art.

In general, the terms "antibody", "antibodies" or "functional equivalents thereof" as used herein are art recognized terms and are understood to refer to molecules or active fragments of molecules that bind to known antigens, particularly to immunoglobulin molecules and to immunologically active portions of immunoglobulin molecules, i.e molecules that contain a binding site that immunospecifically binds an antigen. The immunoglobulin may, in principle, be of any type (IgG, IgM, IgD, IgE, IgA and IgY) or class (IgG1, IgG2, IgG3, IgG4, IgA1 and IgA2) or subclasses of immunoglobulin molecule.

"Antibodies" are intended within the scope of the present invention to include monoclonal antibodies, polyclonal, chimeric, single chain, bispecific, simianized, human and humanized antibodies as well as active fragments thereof. Examples of active fragments of molecules that bind to known antigens include Fab and F(ab')2 fragments, including the products of a Fab immunoglobulin expression library and epitope-binding fragments of any of the antibodies and fragments mentioned above.

These active fragments can be derived from a particular antibody (e.g. obinutuzumab) by a number of techniques. For example, purified monoclonal antibodies can be cleaved with an enzyme, such as pepsin, and subjected to HPLC gel filtration. The appropriate fraction containing Fab fragments can then be collected and concentrated by membrane filtration and the like. For further description of general techniques for the isolation of active fragments of antibodies, see, for example, Khaw, B. A. et al. J. Nucl. Med. 23:1011-1019 (1982); Rousseaux et al. Methods Enzymology, 121: 663-69, Academic Press, 1986.

A "humanized antibody" refers to a type of engineered antibody having its CDRs derived from a non-human donor immunoglobulin, the remaining immunoglobulin-derived parts of the molecule being derived from one (or more) human immunoglobulin(s).

A humanized antibody may further refer to an antibody having a variable region where one or more of its framework regions have human (or primate) amino acids. In addition, framework support residues may be altered to preserve binding affinity. Methods to obtain "humanized antibodies" are well known to those skilled in the art. (see, e.g., Queen et al., Proc. Natl. Acad. Sci. USA, 86:10029-10032 (1989), Hodgson et al., Bio/Technoloy, 9:421 (1991)).

A "humanized antibody" may also be obtained by a novel genetic engineering approach that enables production of affinity-matured humanlike polyclonal antibodies in large animals such as, for example, rabbits.

The term "monoclonal antibody" is also well recognized in the art and refers to an antibody that is mass produced in the laboratory from a single clone and that recognizes only one antigen. Monoclonal antibodies are typically made by fusing a normally short-lived, antibody-producing B cell to a fast-growing cell, such as a cancer cell (sometimes referred to as an "immortal" cell). The resulting hybrid cell, or hybridoma, multiplies rapidly, creating a clone that produces large quantities of the antibody.

The term "antigen" refers to an entity or fragment thereof which can induce an immune response in an organism, particularly an animal, more particularly a mammal including a human. The term includes immunogens and regions responsible for antigenicity or antigenic determinants.

As used herein, the term "soluble" means partially or completely dissolved in an aqueous solution.

Also as used herein, the term "immunogenic" refers to substances which elicit or enhance the production of antibodies, T-cells and other reactive immune cells directed against an immunogenic agent and contribute to an immune response in humans or animals.

The term "hybridoma" is art recognized and is understood by those of ordinary skill in the art to refer to a cell produced by the fusion of an antibody-producing cell and an immortal cell, e.g. a multiple myeloma cell. This hybrid cell is capable of producing a continuous supply of antibody. See the definition of "monoclonal antibody" above for a more detailed description of the method of fusion.

In one embodiment, the functional equivalent of obinutuzumab is envisaged to comprise the constant heavy chain region of obinutuzumab itself (e.g. amino acid positions 120 to 449 of SEQ ID NO. 5), or the constant light chain region of obinutuzumab itself (e.g. amino acid positions 116 to 219 of SEQ ID NO. 6), or both, the constant heavy and light chain regions of obinutuzumab itself. The amino acid sequence of the constant heavy and/or light chain region to be comprised in the functional equivalent of the obinutuzumab may be 100% identical to the amino acid sequence of the constant heavy and/or light chain region of obinutuzumab itself. However, it may also vary to some extent from this/these amino acid sequence(s). For example, it may be at least 70%, at least 75%, at least 80%, at least 85%, at least 90%, at least 95%, at least 98%, at least 99% identical to the respective amino acid sequence of obinutuzumab itself. It is, however, envisaged that such a variant constant heavy and/or light chain region still contributes to the relevant features of obinutuzumab and the functional equivalent of obinutuzumab, respectively (see above for details), in particular to the feature of being glycoengineered as defined herein and contributing to a significantly higher level of ADCC activity as defined herein, respectively.

Most preferably, the antibody to be used in accordance with the invention is obinutuzumab itself (also know a Gazyva™/Gazyvaro™ and GA101; WHO Drug Information 27(1), 2013, 90, Recommended INN: List 69). As mentioned Obinutuzumab is well known in the art and is, for example, described in EP-B1 2380910 and WO 2005/044859. Obinutuzumab has the following structure:

```
Heavy chain
QVQLVQSGAE VKKPGSSVKV SCKASGYAFS YSWINWVRQA PGQGLEWMGR  50

IFPGDGDTDY NGKFKGRVTI TADXSTSTAY MELSSLRSED TAVYYCARNV 100

FDGYWLVYWG QGTLVTVSSA STKGPSVFPL APSSKSTSGG TAALGCLVKD 150

YFPEPVTVSW NSGALTSGVH TFPAVLQSSG LYSLSSVVTV PSSSLGTQTY 200

ICNVNHKPSN TKVDKKVEPK SCDKTHTCPP CPAPELLGGP SVFLFPPKPK 250

DTLMISRTPE VTCVVVDVSH EDPEVKFNWY VDGVEVHNAK TKPREEQYNS 300

TYRVVSVLTV LHQDWLNGKE YKCKVSNKAL PAPIEKTISK AKGQPREPQV 350

YTLPPSRDEL TKNQVSLTCL VKGFYPSDIA VEWESNGQPE NNYKTTFPVL 400

DSDGSFFLYS KLTVDKSRWQ QGNVFSCSVM HEALHNHYTQ KSLSLSPGK  449

Light chain
DIVMTQTPLS LPVTPGEPAS ISCRSSKSLL HSNGITYLYW YLQKPGQSPQ  50'

LLIYQMSNLV SGVPDRFSGS GSGTDFTLKI SRVEAEDVGV YYCAQNLELP 100'

YTFGGGTKVE IKRTVAAPSV FIFPPSDEQL KSGTASVVCL LNNFYPREAK 150'

VQWKVDNALQ SGNSQESVTE QDSKDSTYSL SSTLTLSKAD YEKHKVYACE 200'

VTHQGLSSPV TKSFNRGEC                                  219'

Disulfide bridges location
22-96 22"-96" 23'-93' 23'''-93''' 139'-199' 139'''-199'''

146-202 146"-202" 219'-222 219'''-222" 228-228" 231-231"

263-323 263"-323" 369-427 369"-427"

Glycosylation sites
H CH2 N84.4 299, 299"

(enriched in bisected non-fucosylated oligosaccharides)
```

The antibody rituximab (medical product name: MabThera®; also known as Rituxan®) is also known in the art. It is, for example, described in EP-B1 1005870 (e.g. FIGS. 4 and 5). The amino acid sequence of the heavy chain of rituximab is the depicted in SEQ ID NO. 9. The amino acid sequence of the light chain of rituximab is depicted in SEQ ID NO. 10.

In accordance with the invention, the skilled person is readily able to assess whether a patient advantageously responds to the treatment with obinutuzumab (in particular in combination with a chemotherapy, more particular in combination with a CHOP chemotherapy), as compared to a treatment with rituximab (in particular in combination with a chemotherapy, more particular in combination with a CHOP chemotherapy). In particular, the clinical outcome or clinical endpoints of the treatment can be assessed in this respect. Clinical outcomes/clinical endpoints which can be assessed in this respect are available to the skilled person and are, for example, described in Goede (loc. cit.), Owen (Expert Opin. Biol. Ther. 12(3), 2012, 343-51) and Illidge (Expert Opin. Biol. Ther. 12(5), 2012, 543-5) and in the appended examples.

Preferred examples of a clinical outcome to be assessed in accordance with the invention are progression free survival (PFS), overall survival (OS) and/or event free survival (EFS). The superiority of Obinutuzumab over rituximab in accordance with the invention may also be determined on the basis of one ore more clinical endpoints. In principle, in accordance with the invention, the term clinical outcome is envisaged to refer to a time during the treatment and the term clinical endpoint is envisaged to refer to the time at (or after) the end of the treatment. In accordance with the invention, the clinical endpoint may be a primary clinical endpoint. Particular, however non-limiting, clinical outcomes and clinical endpoints are described in the appended examples.

The skilled person is readily able to decide whether a given clinical outcome is improved in accordance with the invention, i.e. improved as compared to a treatment with rituximab. For example, "improved" in this context means that the clinical outcome (resulting from the treatment with obinutuzumab/a functional equivalent of obinutuzumab (in particular in combination with a chemotherapy, more particular in combination with a CHOP chemotherapy)) is at least 3% higher, at least 5% higher, at least 7% higher, at least 10% higher, at least 15% higher, at least 20% higher, at least 25% higher, at least 30% higher, at least 40% higher, at least 50% higher, at least 75% higher, at least 100% higher, or at least 120% higher, as compared to the clinical outcome resulting from a comparable treatment with rituximab (in particular in combination with a chemotherapy, more particular in combination with a CHOP chemotherapy).

The time at which the clinical outcome/clinical endpoint is assessed can readily be determined by the skilled person. In principle, it is determined at a timepoint when the difference in the clinical outcome/clinical endpoint between the two treatments (obinutuzumab treatment vs. rituximab treatment) becomes (significantly) evident. This time may, for example, be at least 1 month, at least 2 months, at least 3 months, at least 6 months, at least 12 months, at least 18 months, at least 24 months, at least 30 months, at least 36 months, at least 42 months, or at least 48 months, after the beginning of the treatment.

Preferably, the (DLBCL) patient to be treated in accordance with the invention is a human patient/human. Most preferably, the (DLBCL) patient to be treated in accordance with the invention is a 1L DLBCL human patient. This means that the DLBCL patient is a previously untreated DLBCL patient.

However, in principle, also other patients may be treated in accordance with the invention, for example a non-human patient, for example, a pet (e.g. dog, cat, rabbit, rat or mouse), a cattle (e.g. cow, pig, sheep), a horse or a pony or a bird (e.g. chicken, turkey, parrot). Also other warm-blooded animals may be treated in accordance with the invention.

As mentioned, it is particularly envisaged in the context of the invention that the patient defined herein responds to a treatment with obinutuzumab (in particular in combination with a chemotherapy, more particular in combination with a CHOP chemotherapy) by reaching an improved clinical outcome as compared to a treatment with rituximab (in particular in combination with a chemotherapy, more particular in combination with a CHOP chemotherapy).

The antibody to be used in the context of the invention (i.e. obinutuzumab or a functional equivalent thereof) may be administered in combination with further agents. For example, one or more additional other cytotoxic or chemotherapeutic agent(s), or ionizing radiation enhancing the effects of such agent(s), may be co-administered; see, for example, EP-B1 2380910, WO 2005/044859, WO 2015/067586 and WO 2016/207312 for respective examples.

The terms "administered in combination with" or "co-administration", "co-administering", "combination therapy" or "combination treatment" refer to the administration of the antibody as described herein, and the other agent(s) as described herein, e.g. as separate formulations/applications (or as one single formulation/application). The co-administration can be simultaneous or sequential in either order, wherein preferably there is a time period while both (or all) active agents simultaneously exert their biological activities. Said antibody and said further agent(s) are co-administered either simultaneously or sequentially (e.g. intravenous (i.v.)), for example through a continuous infusion. When both therapeutic agents are co-administered sequentially the dose administered either on the same day in two separate administrations, or one of the agents may be administered on day 1 and the second may be co-administered on day 2 to day 7, preferably on day 2 to 4. Thus in one embodiment the term "sequentially" means within (about) 7 days after the dose of the first component, preferably within (about) 4 days after the dose of the first component; and the term "simultaneously" means at the same time. The term "co-administration" with respect to the maintenance doses of the antibody and/or further agent(s) means that the maintenance doses can be either co-administered simultaneously, if the treatment cycle is appropriate for both drugs, e.g. every week or the further agent is, e.g., administered, e.g., every first to third day and said antibody is administered every week. Or the maintenance doses are co-administered sequentially, either within one or within several days. In addition to the antibody, optionally in combination with the other agent(s), also (a) chemotherapeutic agent(s) or targeted therapies may be administered.

Such additional chemotherapeutic agents, which may be co-administered, include, but are not limited to, anti-neoplastic agents including alkylating agents including: nitrogen mustards, such as mechlorethamine, cyclophosphamide, ifosfamide, melphalan and chlorambucil; nitrosoureas, such as carmustine (BCNU), lomustine (CCNU), and semustine (methyl-CCNU); Temodal(TM) (temozolamide), ethylenimines/methylmelamine such as thriethylenemelamine (TEM), triethylene, thiophosphoramide (thiotepa), hexamethylmelamine (HMM, altretamine); alkyl sulfonates such as busulfan; triazines such as dacarbazine (DTIC); antimetabolites including folic acid analogs such as methotrexate and trimetrexate, pyrimidine analogs such as 5-fluorouracil (5FU), fluorodeoxyuridine, gemcitabine, cytosine arabinoside (AraC, cytarabine), 5-azacytidine, 2,2'-difluorodeoxycytidine, purine analogs such as 6-merca.rho.topurine, 6-thioguamne, azathioprine, T-deoxycoformycin (pentostatin), erythrohydroxynonyladenine (EHNA), fludarabine phosphate, and 2-chlorodeoxyadenosine (cladribine, 2-CdA); natural products including antimitotic drugs such as paclitaxel, vinca alkaloids including vinblastine (VLB), vincristine, and vinorelbine, taxotere, estramustine, and estramustine phosphate; pipodophylotoxins such as etoposide and teniposide; antibiotics such as actinomycin D, daunomycin (rubidomycin), doxorubicin, mitoxantrone, idarubicin, bleomycins, plicamycin (mithramycin), mitomycin C, and actinomycin; enzymes such as L-asparaginase; biological response modifiers such as interferon-alpha, IL-2, G-CSF and GM-CSF; miscellaneous agents including platinum coordination complexes such as oxaliplatin, cisplatin and carboplatin, anthracenediones such as mitoxantrone, substituted urea such as hydroxyurea, methylhydrazine derivatives including N-methylhydrazine (MIH) and procarbazine, adrenocortical suppressants such as mitotane (o, p-DDD) and aminoglutethimide; hormones and antagonists including adrenocorticosteroid antagonists such as prednisone and equivalents, dexamethasone and aminoglutethimide; Gemzar(TM) (gemcitabine), progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/equivalents; antiandrogens such as flutamide, gonadotropin-releasing hormone analogs and leuprolide; and non-steroidal antiandrogens such as flutamide. Therapies targeting epigenetic mechanism including, but not limited to, histone deacetylase inhibitors, demethylating agents (e.g., Vidaza) and release of transcriptional repression (ATRA) therapies can also be combined with the antigen binding proteins. In one embodiment the chemotherapeutic agent is selected from the group consisting of taxanes (like e.g. paclitaxel (Taxol), docetaxel (Taxotere), modified paclitaxel (e.g., Abraxane and Opaxio), doxorubicin, sunitinib (Sutent), sorafenib (Nexavar), and other multikinase inhibitors, oxaliplatin, cisplatin and carboplatin, etoposide, gemcitabine, and vinblastine. In one embodiment the chemotherapeutic agent is selected from the group consisting of taxanes (like e.g. taxol (paclitaxel), docetaxel (Taxotere), modified paclitaxel (e.g. Abraxane and Opaxio). In one embodiment, the additional chemotherapeutic agent is selected from 5-fluorouracil (5-FU), leucovorin, irinotecan, or oxaliplatin. In one embodiment the chemotherapeutic agent is 5-fluorouracil, leucovorin and irinotecan (FOLFIRI). In one embodiment the chemotherapeutic agent is 5-fluorouracil, and oxaliplatin (FOLFOX).

In a preferred embodiment, the antibody defined herein (i.e. obinutuzumab and its functional equivalents) may be administered in combination with a chemotherapy, for example with a CHOP chemotherapy (more preferred) or with variants of a CHOP chemotherapy, like a CHOEP chemotherapy, a CHOP-14 chemotherapy or a ACVBP chemotherapy (see, for example, the appended examples, infra, and also EP-B1 2380910, WO 2005/044859 and Scott, 2014 and 2015, loc. cit.). Therefore, in a preferred embodiment, the additional chemotherapeutic agents to be co-administered are selected from the group consisting of Cyclophosphamide, Hydroxydaunorubicin, Oncovein, Prednisone or Prednisolone and, optionally, Etoposide.

The antibody to be used in the context of the invention may be comprised in a composition, in particular in a pharmaceutical composition. The pharmaceutical composition may comprise a pharmaceutically acceptable carrier.

Suitable pharmaceutical compositions and pharmaceutically acceptable carriers are known in the art and are, for example, described in EP-B1 2380910, WO 2005/044859, WO 2015/067586 and WO 2016/207312.

Accordingly, in another aspect, a composition, e.g. a pharmaceutical composition, containing an antibody, or an antigen-binding portion thereof, as defined herein, optionally formulated together with a pharmaceutically acceptable carrier, is envisaged to be employed in accordance with the invention.

As used herein, "pharmaceutically acceptable carrier" includes any and all suitable solvents, dispersion media, coatings, antibacterial and antifungal agents, isotonic and absorption/resorption delaying agents, and the like, that are physiologically compatible. Preferably, the pharmaceutical composition and carrier, respectively is suitable for injection or infusion.

Pharmaceutically acceptable carriers include sterile aqueous solutions or dispersions and sterile powders for the preparation of sterile injectable solutions or dispersion. The use of such media and agents for pharmaceutically active substances is known in the art. In addition to water, the carrier can be, for example, an isotonic buffered saline solution.

Acceptable carriers, excipients, or stabilizers are envisaged to be nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

A composition/antibody of the present invention can be administered by a variety of methods known in the art. As will be appreciated by the skilled artisan, the route and/or mode of administration will vary depending upon the desired results.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Exemplary antibody formulations which, appropriately adapted, may be employed also in accordance with the invention are described in WO98/56418. This publication describes a liquid multidose formulation comprising 40 mg/mL antibody, 25 mM acetate, 150 mM trehalose, 0.9% benzyl alcohol, 0.02% polysorbate 20 at pH 5.0 that has a minimum shelf life of two years storage at 2-8° C. Another antibody formulation comprises 10 mg/mL antibody in 9.0 mg/mL sodium chloride, 7.35 mg/mL sodium citrate dihydrate, 0.7 mg/mL polysorbate 80, and Sterile Water for Injection, pH6.5.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient (effective amount). The selected dosage level will depend upon a variety of pharmacokinetic factors including the activity of the particular compositions of the present invention employed, or the ester, salt or amide thereof, the route of administration, the time of administration, the rate of excretion of the particular compound being employed, other drugs, compounds and/or materials used in combination with the particular compositions employed, the age, sex, weight, condition, general health and prior medical history of the patient being treated, and like (other) factors well known in the medical arts.

The term "a method of treating" or its equivalent, when applied to, for example, DLBCL, and the patient defined herein, respectively, refers to a procedure or course of action that is, for example, designed to reduce or eliminate the number of DLBCL tumor cells in a patient, or to alleviate the symptoms of a DLBCL tumor. "A method of treating" DLBCL, however, may not necessarily mean that the DLBCL tumor cells will, in fact, be eliminated, that the number of cells will, in fact, be reduced, or that the symptoms of a DLBCL tumor will, in fact, be alleviated. Often, a method of treating DLBCL will be performed even with a low likelihood of success, but which, given the medical history and estimated survival expectancy of a patient, is nevertheless deemed to induce an overall beneficial course of action, in particular as compared to a rituximab treatment.

It is self-evident that the antibody is (to be) administered to the patient in a "therapeutically effective amount" (or simply "effective amount") which is the amount of the respective compound or combination that will elicit the biological or medical response, for example of a tissue, system, animal or human, that is being sought by the researcher, veterinarian, medical doctor or other clinician.

The amount of (co-)administration and the timing of (co-)administration will depend on the type (species, gender, age, weight, etc.) and condition of the patient being treated and the severity of the disease or condition being treated. The antibody, and optionally a further agent, are suitably (co-)administered to the patient at one time or over a series of treatments e.g. on the same day or on the day after.

Depending on the type and severity of the disease, about 0.1 mg/kg to 50 mg/kg (e.g. 0.1-20 mg/kg) of the antibody defined herein is an initial candidate dosage for co-administration to the patient.

A particular, however non-limiting, example of a scheme of administration (including administration routes and dosages) for obinutuzumab/a functional equivalent of obinutuzumab (more particular G-CHOP) is described in and provided by the appended examples (in particular example 1 and example 2 which describes the study design and treatments applied in the context of the GOYA study in detail). The skilled person is, if need be, readily able to adapt this example of a G administration scheme to any other G administration scheme which might be appropriate in accordance with the invention.

The antibody and pharmaceutical composition, respectively, to be employed in accordance with the invention may be provided together with an instruction manual or instruction leaflet. The instruction manual/leaflet may comprise guidance for the skilled person/attending physician on how to treat DLBCL and the patient defined herein in accordance with the invention. For example, the instruction manual/leaflet may comprise guidance as to the herein described mode of administration/administration regimen (for example route of administration, dosage regimen, time of administration, frequency of administration). In particular, the instruction manual/leaflet may comprise information as to the patient to be treated, i.e. the patient defined herein. In principle, what has been said herein elsewhere with respect to obinutuzumab, the patient to be treated, the mode of administration/administration regimen (including dosages etc.) etc. may be comprised in the instruction manual/leaflet.

A preferred sample to be employed in the context of the invention is derived from the patient's tumor tissue (e.g. as a biopsy). For example, formalin-fixed or, preferably and, paraffin-embedded tumor tissue may be employed (e.g. sections of tumor tissue on an object slide). However, also other samples are envisaged to be employed in the context of the invention, for example, sections/biopsies of other tissues, blood samples, serum samples, or other body fluid samples, and the like.

In this specification, a number of documents including patents/patent applications are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The invention will now be described by reference to the following figures and examples which are not to be construed as a limitation of the scope of the present invention.

BRIEF DESCRIPTION OF THE DRAWINGS

The application file contains at least one drawing executed in color. Copies of this patent or patent application with color drawings will be provided by the Office upon request and payment of the necessary fee.

Disposition of patients in GOYA.

*Discontinued refers to patients who discontinued study (antibody) treatment.

†Median observation time was 29 months in each group; completed treatment refers to patients who completed study (antibody) treatment.

Patients were stratified at randomization by IPI score (low/low-intermediate, high-intermediate, and high-risk), planned number of CHOP cycles (8 vs. 6), and geographic region (Western Europe, Eastern Europe, South and Central America, North America, Asia, and others).

G-CHOP, obinutuzumab plus cyclophosphamide, doxorubicin, vincristine, and prednisone/prednisolone; R-CHOP, rituximab plus cyclophosphamide, doxorubicin, vincristine, and prednisone/prednisolone.

Kaplan-Meier estimates of PFS and OS in GOYA.

Figure 2A:
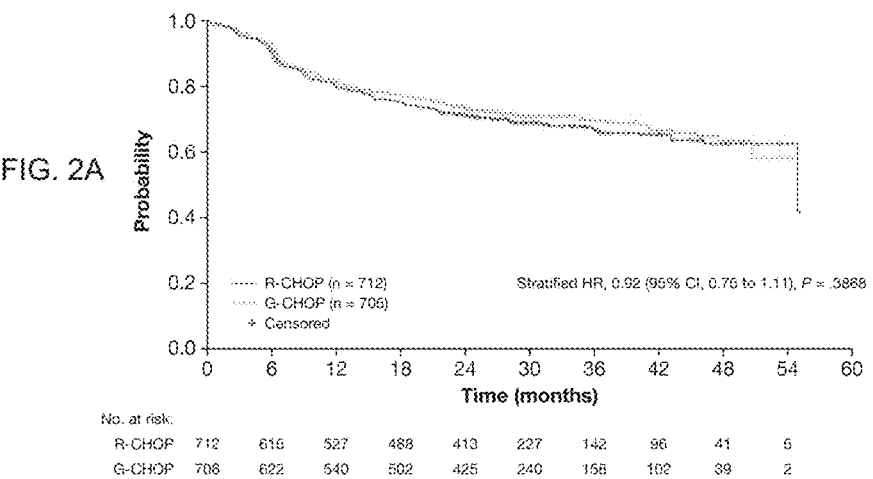
Figure 2B:
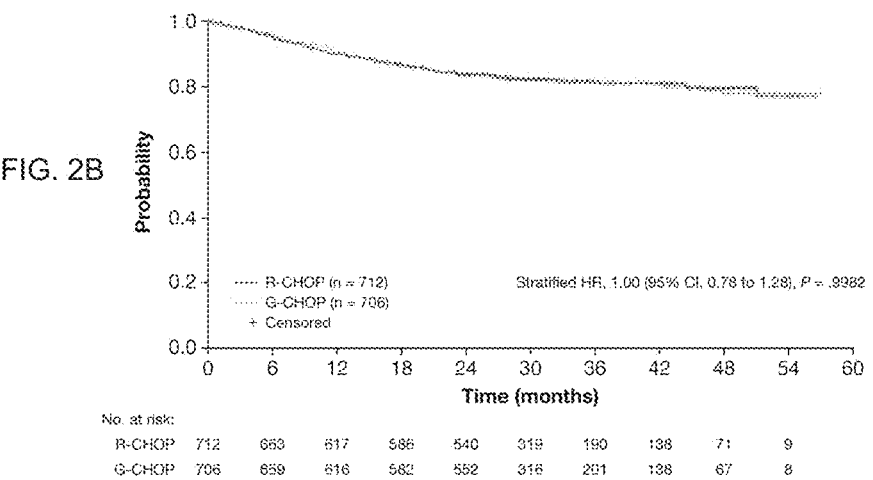
Figure 2C:
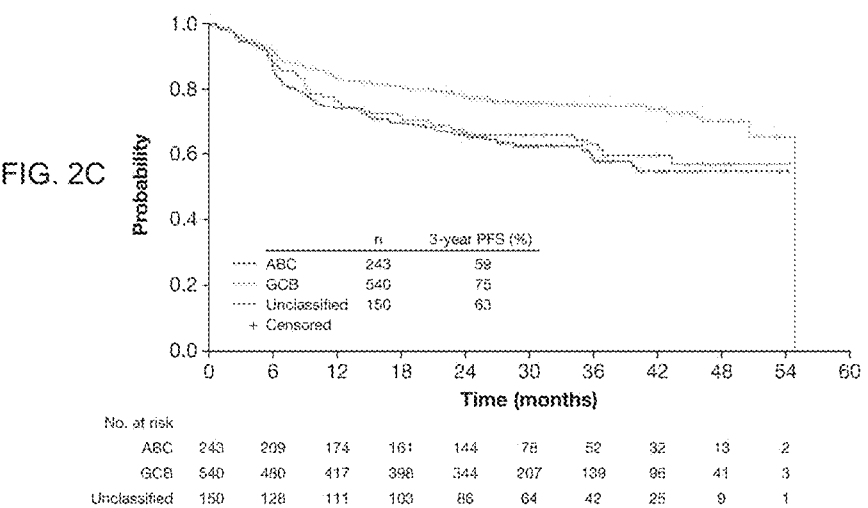

FIG. 2A: investigator-assessed PFS (primary endpoint) by treatment, intent-to-treat population, FIG. 2B: OS by treatment, intent-to-treat population FIG. 2C: investigator-assessed PFS by cell-of-origin subtype (irrespective of study treatment) in patients with cell-of-origin data.

ABC, activated B-cell-like; CI, confidence interval; GCB, germinal-center B-cell-like; G-CHOP, obinutuzumab plus cyclophosphamide, doxorubicin, vincristine, and prednisone; HR, hazard ratio; OS, overall survival; PFS, progression-free survival; R-CHOP, rituximab plus cyclophosphamide, doxorubicin, vincristine, and prednisone.

Unstratified hazard ratios for investigator-assessed PFS in GOYA patient subgroups.

Figure 3A:
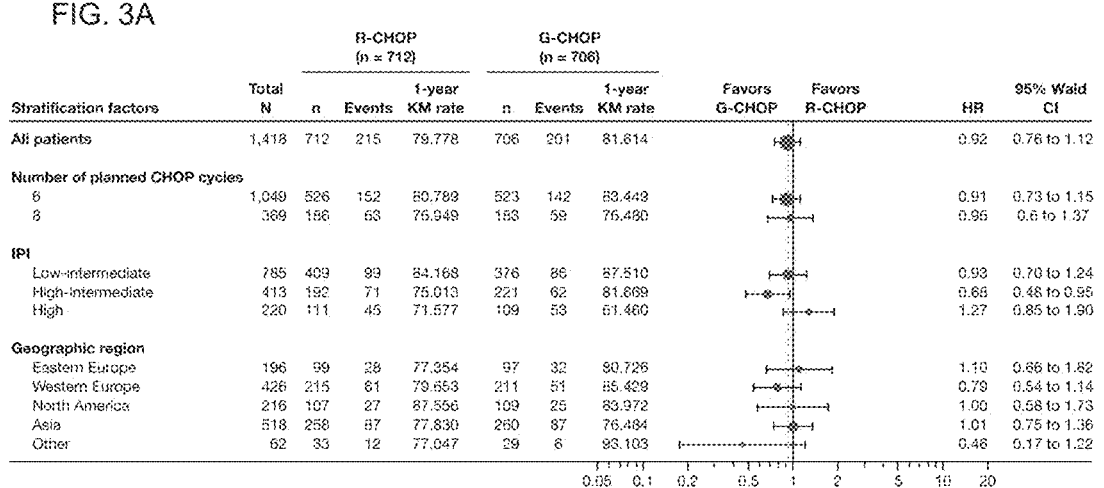
Figure 3B:
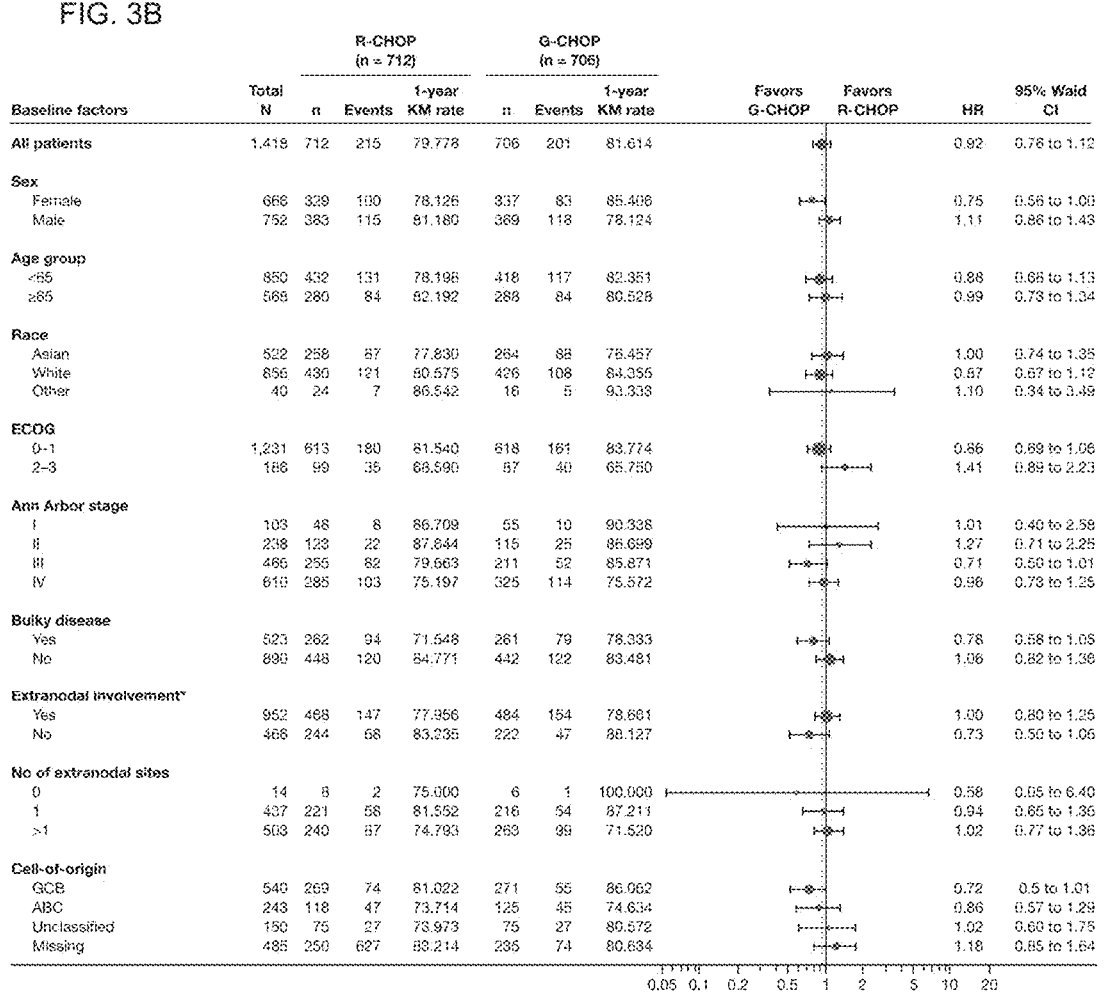

FIG. 3A: randomization stratification factors and FIG. 3B: baseline characteristics.

ABC, activated B-cell-like; CI, confidence interval; DLBCL, diffuse large B-cell lymphoma;

ECOG PS, Eastern Cooperative Oncology Group performance status; GCB, germinal-center B-cell-like; G-CHOP, obinutuzumab plus cyclophosphamide, doxorubicin, vincristine, and prednisone; IPI, International Prognostic Index; KM, Kaplan-Meier; PFS, progression-free survival; R-CHOP, rituximab plus cyclophosphamide, doxorubicin, vincristine, and prednisone.

*Cases where 'yes' was ticked in the eCRF for extranodal involvement; 14 patients with extranodal sites 0 were ticked in error.

FIG. 4

Gazyva benefit in BCL2 translocated patients in GOYA

FIG. 5

Gazyva benefit in BCL2 protein expression positive patients in GOYA

FIG. 6

Gazyva benefit in BCL2 translocated patients that are BCL2 protein expression positive in GOYA Evaluation of treatment effect in quadrants defined by BCL2 IHC (pos/neg) and BCL2 FISH (pos/neg) in GOYA. Gazyva superiority shown to be specific to BCL2 $IHC_+$/$FISH_+$ pts.

Figure 7A:
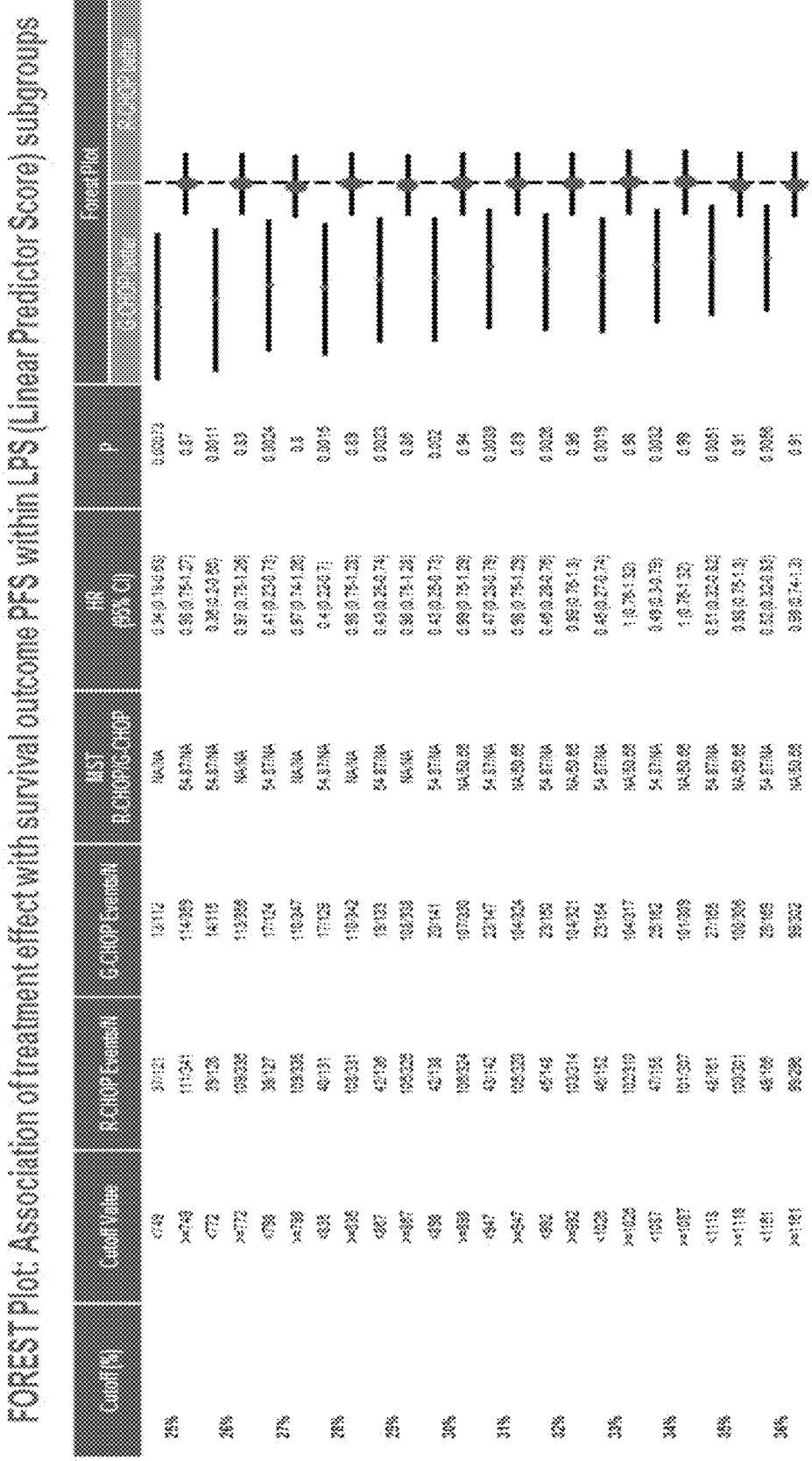

Gazyva benefit in subgroups of GCB defined by various cutoffs of the Linear Predictor Score in GOYA FIG. 7A: FOREST Plot 25%-36% cutoff (%)

Figure 7B:
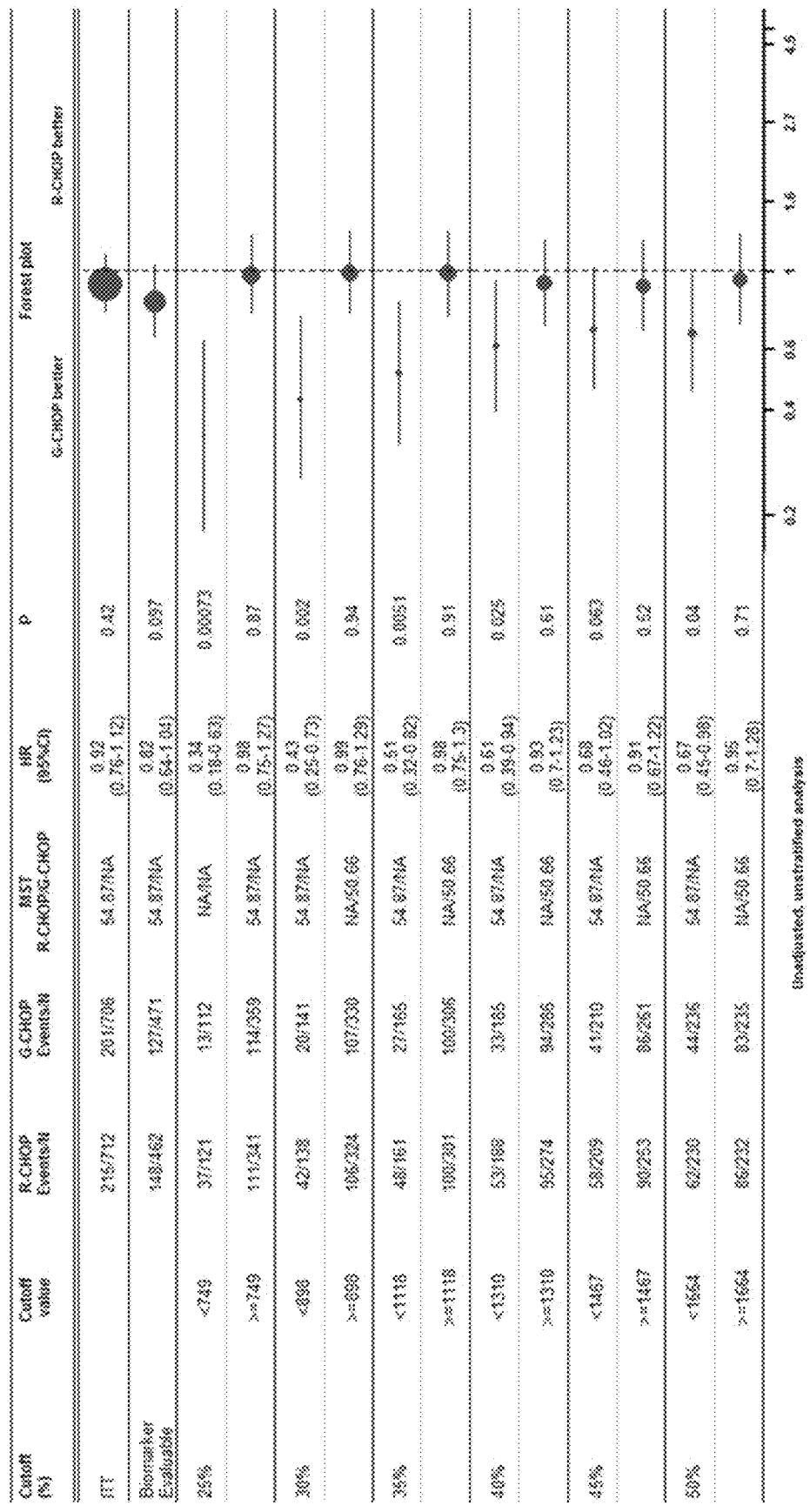

FIG. 7B: FOREST Plot 25%-50% cutoff (%)

Figure 7C:
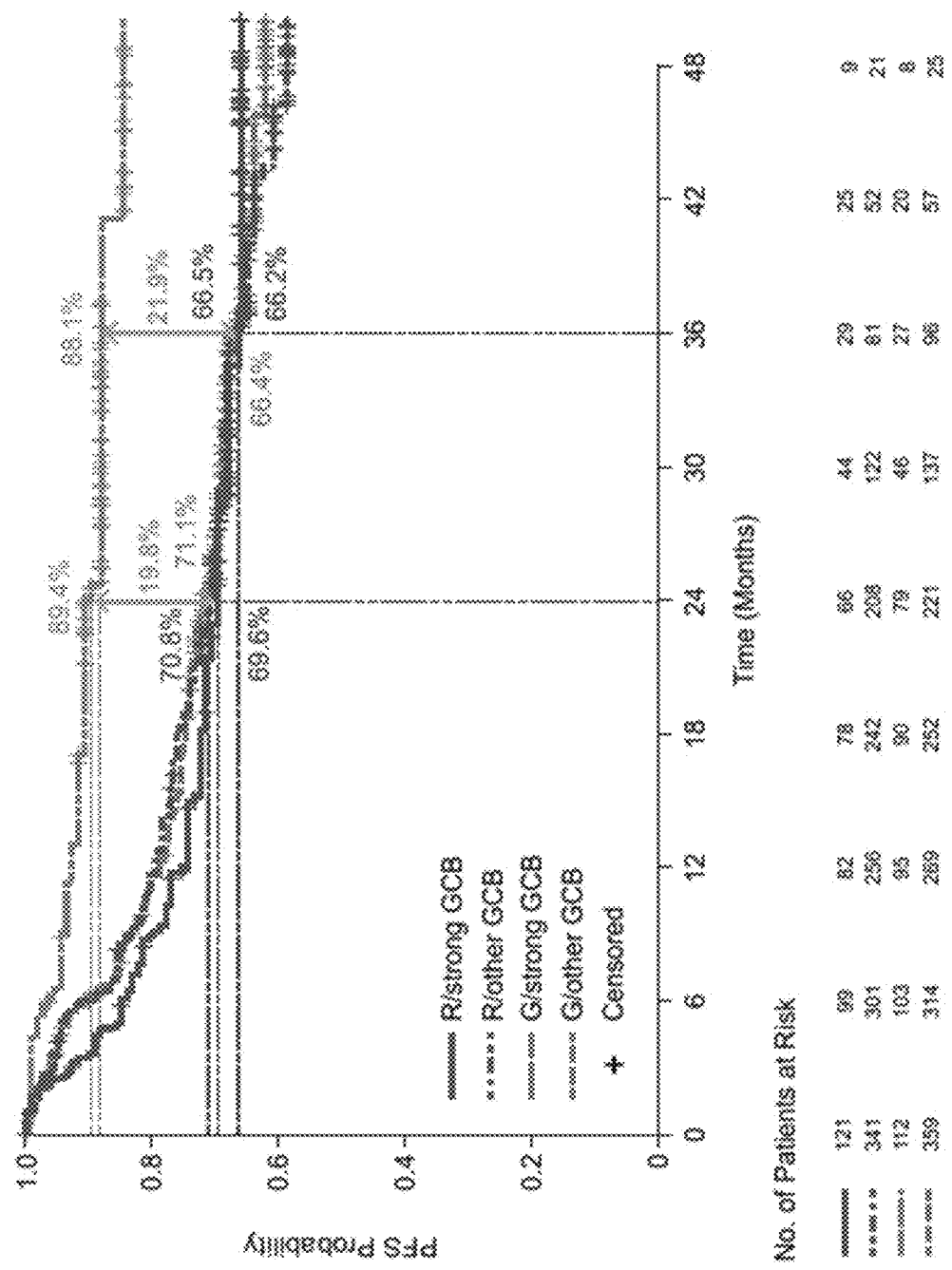

FIG. 7C: Benefit of Gazyva in strong-GCB subgroup for the primary endpoint (INV-PFS) at LPS cut-off of <749.

HR* (95% CI) in strong-GCB GOYA pts

PFS: 0.33 [0.18-0.63], p-value=0.0007

Strong-GCB pts represent the 25% (n=233/933) of all DLBCL pts in GOYA with LPS<749.

Strong-GCB pts make up 43% (n=233/540) of GCB pts in GOYA

FIG. 8

Gazyva benefit in GCB patients that are BCL2 translocated and BCL2 protein expression positive in GOYA.

FIG. 9

Gazyva benefit in CD58 mutated patients and/or patients with low CD58 gene expression in GOYA.

FIG. 10

Multivariate simulation optimization of the LPS cutoff for G-CHOP benefit over R-CHOP on progression-free survival in biomarker-evaluable pts with COO analysis (N=xx).

LPS cutoff optimization for strong-GCB treatment effect in GOYA original data.

*Multivariate HR adjusted for treatment, International Prognostic Index, number of chemotherapy cycles (6 or 8), and geographical region. Blue line, point estimate of the HR, yellow line, 95% CI; CI, confidence interval; COO, cell of origin; HR, hazard ratio; LPS, Linear Predictor Score.

Molecular characterization of strong-GCB patients[#] in GOYA.

Strong-GCB patients have significantly higher prevalence of FL somatic mutation hallmarks.

Figure 11B:
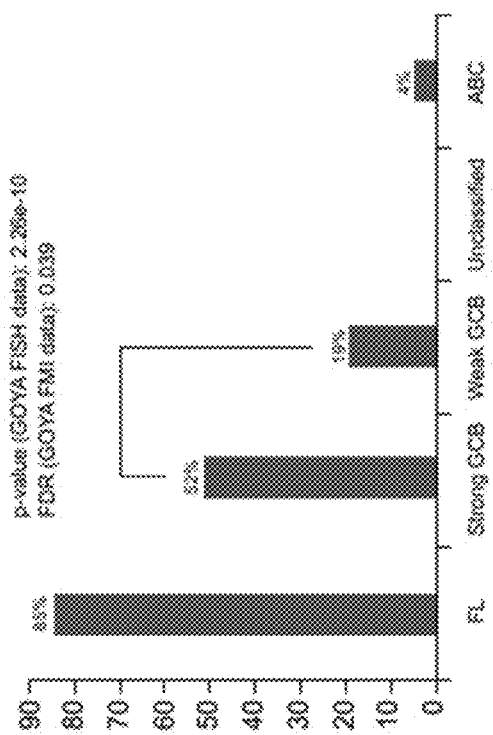
Figure 11A:
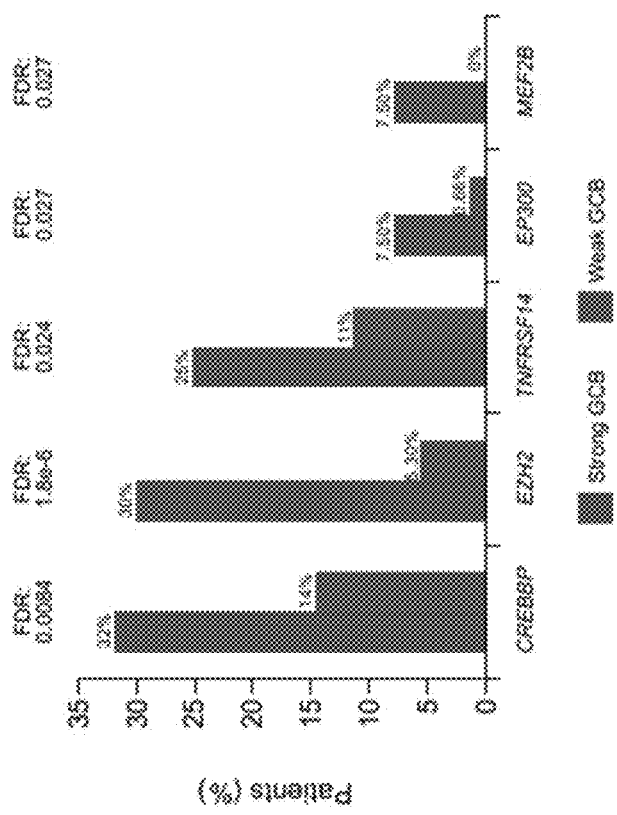

FIG. 11A: Prevalence of FL somatic mutation hallmarks* (any mutation type).

FIG. 11 B: Prevalence of BCL2 Translocations[†]

[#] Other biomarkers evaluated to characterize strong-from weak-GCB, where no significant difference in prevalence rate was identified, were: by gene expression, stromal-1/2 gene signatures, immune-response 1/2 gene signatures, CD20, and PTEN; by protein expression, BCL2, MYC, and BCL2/MYC double-expressors; and by gene translocations, MYC translocations and BCL2/MYC double-hit. ABC, activated B-cell; DLBCL, diffuse large B-cell lymphoma; FDR, false discovery rate; FISH, fluorescence in situ hybridization; FL, follicular lymphoma; GCB, germinal center B-cell; NGS, next-generation sequencing.

FIG. 12

Distribution of optimal LPS cutoff across bootstrap samples

Bootstrap multivariate simulations to further test robustness and generalizability of an optimal LPS identified using the "min.HR rule"

Extreme peak across bootstrap samples is at LPS=725

LPS distribution with its unique peak, supports robustness of treatment effect signal Optimal LPS cutoff suggested for new potential confirmatory study is LPS≤725

Historically all GOYA biomarker analyses has defined strong-GCB as <749 (25% of pts in GOYA), including biomarker analyses presented in this OBRF n=4 pts with 725<LPS<749, all G-CHOP (1 event)

FIG. 13

Kaplan-Meier Estimates of Time to Next Anti-Lymphoma Treatment (Secondary Endpoint) in the Intent-To-Treat Population.

CI, confidence interval; G-CHOP, obinutuzumab plus cyclophosphamide, doxorubicin, vincristine, and prednisone/prednisolone; HR, hazard ratio; R-CHOP, rituximab plus cyclophosphamide, doxorubicin, vincristine, and prednisone/prednisolone.

Kaplan-Meier Estimates of Investigator-Assessed PFS by Treatment Arm in Patients With COO Data, Subgrouped by COO Subtype.

Figure 14A:
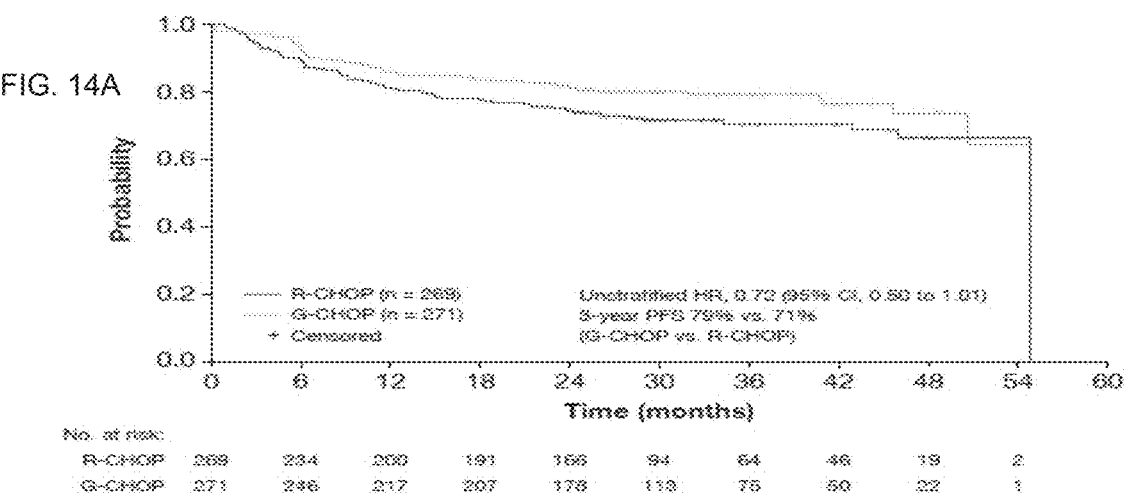
Figure 14B:
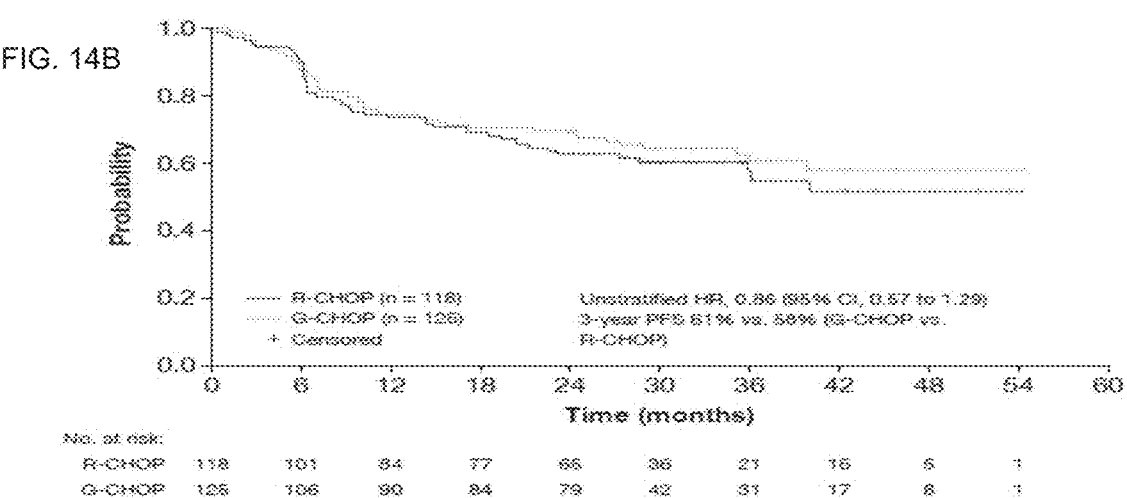

FIG. 14A GCB; FIG. 14B ABC; FIG. 14C Unclassified.

ABC, activated B-cell-like; CI, confidence interval; COO, cell of origin; GCB, germinal-center B-cell-like; G-CHOP, obinutuzumab plus cyclophosphamide, doxorubicin, vincristine, and prednisone/prednisolone; HR, hazard ratio; R-CHOP, rituximab plus cyclophosphamide, doxorubicin, vincristine, and prednisone/prednisolone.

The present invention also refers to the following tables.

TABLE 1

Baseline Patient and Disease Characteristics (Intent-to-Treat Population)

| Characteristic | G-CHOP (N = 706)* | R-CHOP (N = 712)* |
|---|---|---|
| Median age, years (range) | 62.0 (18-86) | 62.0 (18-83) |
| Male - no. (%) | 369 (52.3) | 383 (53.8) |
| Geographic region - no. (%) | | |
| Asia | 260 (36.8) | 258 (36.2) |
| Western Europe | 211 (29.9) | 215 (30.2) |
| North America | 109 (15.4) | 107 (15.0) |
| Eastern Europe | 97 (13.7) | 99 (13.9) |
| Other | 29 (4.1) | 33 (4.6) |
| ECOG PS - no. (%) | n = 705 | n = 712 |
| 0-1 | 618 (87.7) | 613 (86.1) |
| 2-3 | 87 (12.3) | 99 (13.9) |
| Ann Arbor stage - no. (%) | n = 706 | n = 711 |
| I and II | 170 (24.1) | 171 (24.0) |
| III and IV | 536 (75.9) | 540 (75.8) |
| IPI risk group - no. (%) | | |
| Low/low intermediate | 376 (53.3) | 409 (57.4) |
| High-intermediate | 221 (31.3) | 192 (27.0) |
| High | 109 (15.4) | 111 (15.6) |
| Planned chemotherapy cycles - no. (%) | | |
| 6 | 523 (74.1) | 526 (73.9) |
| 8 | 183 (25.9) | 186 (26.1) |
| LDH elevated - no. (%) | n = 705 | n = 708 |
| | 415 (58.9) | 401 (56.6) |
| Extranodal involvement - no. (%)[†] | 484 (68.6) | 468 (65.7) |
| Bulky disease (7.5 cm) - no. (%) | 261/703 (37.1) | 262/710 (36.9) |
| Cell of origin | n = 471[‡] | n = 462[‡] |
| GCB | 271 (57.5) | 269 (58.2) |
| ABC | 125 (26.5) | 118 (25.5) |
| Unclassified | 75 (15.9) | 75 (16.2) |

ABC, activated B cell-like (subgroup); ECOG PS, Eastern Cooperative Oncology Group performance status; G-CHOP, obinutuzumab plus cyclophosphamide, doxorubicin, vincristine, and prednisone/prednisolone; GCB, germinal-center B cell-like (subgroup); IPI, International Prognostic Index; LDH, lactate dehydrogenase; PET, positron emission tomography; R-CHOP, rituximab plus cyclophosphamide, doxorubicin, vincristine, and prednisone/prednisolone.
*n = 706 for G-CHOP and n = 712 for R-CHOP for all parameters unless otherwise specified.
[†]Cases where 'yes' was ticked in the eCRF for extranodal involvement; 14 patients with extranodal sites 0 were ticked in error.
[‡]COO subtype classification was missing for 485 patients (G-CHOP, 235; R-CHOP, 250); includes samples from China which could not be analyzed due to lack of an export license - analysis of these samples is planned in the near future.

TABLE 2

Summary of Efficacy Endpoints (Intent-to-Treat Population)

| | Investigator Assessment | |
|---|---|---|
| Endpoint | G-CHOP N = 706) | R-CHOP N = 712) |
| Median observation time, months (range) | 29.0 (0.1-56.6) | 28.9 (0.1-56.2) |
| Investigator-assessed PFS (primary endpoint) | N = 706 | N = 712 |
| Patients with event, no. (%) | 201 (28.5) | 215 (30.2) |
| 3-year PFS, % | 69.6 | 66.9 |
| Stratified HR (95% CI) - P value (log-rank)* | 0.92 (0.76-1.11), P = .3868 | |
| IRC-assessed PFS | N = 706 | N = 712 |
| Patients with event, no. (%) | 171 (24.2) | 186 (26.1) |

TABLE 2-continued

Summary of Efficacy Endpoints (Intent-to-Treat Population)

| Endpoint | Investigator Assessment | |
|---|---|---|
| | G-CHOP N = 706) | R-CHOP N = 712) |
| 3-year PFS, % | 72.5 | 70.6 |
| Stratified HR (95% CI), P value (log-rank)* | 0.89 (0.72 to 1.10), P = .2736 | |
| OS | N = 706 | N = 712 |
| Patients with event, no. (%) | 126 (17.8) | 126 (17.7) |
| 3-year OS, % (95% CI) | 81.2 (77.9 to 84.1) | 81.4 (78.1 to 84.3) |
| Stratified HR (95% CI)* | 1.00 (0.78 to 1.28) | |
| DFS in patients with investigator-assessed CR | n = 397 | n = 369 |
| Patients with event, no. (%) | 77 (19.4) | 64 (17.3) |
| Stratified HR (95% CI)* | 1.27 (0.91 to 1.77) | |
| Investigator-assessed EFS | N = 706 | N = 712 |
| Events, no. (%) | 236 (33.4) | 250 (35.1) |
| Stratified HR (95% CI)* | 0.92 (0.77 to 1.11) | |
| Time to start of new anti-lymphoma treatment | N = 706 | N = 712 |
| Patients with event, no. (%) | 213 (30.2) | 230 (32.3) |
| Proportion event-free at 3 years, % (95% CI) | 69.9 (66.2 to 73.2) | 66.5 (62.7 to 70.1) |
| Stratified HR (95% CI)* | 0.92 (0.76 to 1.11) | |
| Investigator-assessed response (with PET) at end of treatment[†] | n = 669 | n = 665 |
| ORR | | |
| Proportion, no. (%) | 518 (77.4) | 518 (77.9) |
| Percentage difference (95% CI) | −0.47 (−5.01 to 4.08) | |
| CR | | |
| Proportion, no. (%) | 379 (56.7) | 396 (59.5) |
| Difference (95% CI) | −2.90 (−8.27 to 2.48) | |
| Investigator-assessed response (without PET) at end of treatment[†] | N = 706 | N = 712 |
| ORR | | |
| Proportion, no. (%) | 577 (81.7) | 572 (80.3) |
| Percentage difference (95% CI) | 1.39 (−2.76 to 5.54) | |
| CR | | |
| Proportion, no. (%) | 248 (35.1) | 241 (33.8) |
| Difference (95% CI) | 1.28 (−3.74 to 6.30) | |

CI, confidence interval; CR, complete response; DFS, disease-free survival; EFS, event-free survival; G-CHOP, obinutuzumab plus cyclophosphamide, doxorubicin, vincristine, and prednisone/prednisolone; HR, hazard ratio; IRC, Independent Review Committee; ORR, overall response rate; OS, overall survival; PET, positron emission tomography; PFS, progression-free survival; R-CHOP, rituximab plus cyclophosphamide, doxorubicin, vincristine, and prednisone/prednisolone.
*Stratification factors were International Prognostic Index score and planned number of CHOP cycles (6 or 8).
[†]According to revised response criteria.[13]

TABLE 3

Summary of AEs Including Grade 3-5 and Serious AEs Reported by 5% of Patients in Either Group (At Preferred Term Level; Safety Population)

| | G-CHOP (N = 704), No. (%) | R-CHOP (N = 703), No. (%) | | |
|---|---|---|---|---|
| Number of deaths for any reason | 126 (17.9) | 122 (17.4) | | |
| Number of patients withdrawn from study due to an AE | 4 (0.6) | 3 (0.4) | | |
| Patients with at least one | | | | |
| AE | 683 (97.0%) | 657 (93.5) | | |
| Grade 3-5 AE | 519 (73.7) | 455 (64.7) | | |
| AE with fatal outcome* | 41 (5.8) | 30 (4.3) | | |
| Serious AE | 300 (42.6) | 264 (37.6) | | |
| Treatment-related AEs | 639 (90.8) | 596 (84.8) | | |
| AEs leading to withdrawal of any treatment | 84 (11.9) | 60 (8.5) | | |
| AEs leading to dose reduction for any treatment | 145 (20.6) | 138 (19.6) | | |
| | Grade 3-5 AEs | Serious AEs | Grade 3-5 AEs | Serious AEs |
| Blood and lymphatic system disorders | | | | |
| Total number of patients with at least one AE | 415 (58.9) | 135 (19.2) | 348 (49.5) | 113 (16.1) |
| Neutropenia | 325 (46.2) | 52 (7.4) | 268 (38.1) | 40 (5.7) |

TABLE 3-continued

Summary of AEs Including Grade 3-5 and Serious AEs Reported by 5% of Patients in Either Group (At Preferred Term Level; Safety Population)

|  | G-CHOP (N = 704), No. (%) | | R-CHOP (N = 703), No. (%) | |
|---|---|---|---|---|
| Febrile neutropenia | 123 (17.5) | 81 (11.5) | 107 (15.2) | 72 (10.2) |
| Leukopenia | 96 (13.6) | 10 (1.4) | 71 (10.1) | 5 (0.7) |
| Anemia | 51 (7.2) | 9 (1.3) | 53 (7.5) | 6 (0.9) |
| Infections and infestations | | | | |
| Total number of patients with at least one AE | 135 (19.2) | 121 (17.2) | 109 (15.5) | 94 (13.4) |
| Pneumonia | 40 (5.7) | 40 (5.7) | 35 (5.0) | 32 (4.6) |

AE, adverse event; G-CHOP, obinutuzumab plus cyclophosphamide, doxorubicin, vincristine, and prednisone/prednisolone; R-CHOP, rituximab plus cyclophosphamide, doxorubicin, vincristine, and prednisone/prednisolone.
*Fatal AEs that were reported in more than one patient in either group, listed as preferred terms, were: septic shock (6 [0.9%] patients), pneumonia (5 [0.7%]), death (cause unknown; 3 [0.4%]), pulmonary embolism (2 [0.3%]) and cerebrovascular accident (2 [0.3%]) in the G-CHOP group and pneumonia (6 [0.9%]), sepsis (3 [0.4%]), cerebrovascular accident (2 [0.3%]) and death (cause unknown; 2 [0.3%]) in the R-CHOP group.

TABLE 4

Effect of G-CHOP and R-CHOP on clinical outcomes in strong-GCB and all other patients

| Multivariate Analysis HR (G vs R)* [95% CI]; p-value 3-yr rate (%) | Strong-GCB Pts (n = 233) R-CHOP: n = 121 G-CHOP: n = 112 | All Other Pts (n = 700) R-CHOP: n = 341 G-CHOP: n = 359 |
|---|---|---|
| PFS | 0.33 [0.18-0.63]; p = 0.0007 R: 66%; G: 88% | 0.99 [0.76-1.28]; p = 0.9117 R: 66%; G: 66% |
| EFS | 0.47 [0.28-0.78]; p = 0.00344 R: 59%; G: 80% | 1.01 [0.79-1.29]; p = 0.9513 R: 63%; G: 62% |
| OS | 0.41 [0.20-0.87]; p = 0.019 R: 79%; G: 92% | 1.10 [0.79-1.53]; p = 0.582 R: 81%; G: 78% |

*Adjusted for treatment arm, International Prognostic Index, number of chemotherapy cycles (6 or 8), and geographic region
CI, confidence interval; EFS, event-free survival; GCB, germinal center B-cell; HR, hazard ratio; OS, overall survival; PFS, progression-free survival (investigator-assessed); yr, year

TABLE 5

Study Drug Exposure

| | G-CHOP (N = 704), No. (%) | R-CHOP (N = 703), No. (%) |
|---|---|---|
| Number of obinutuzumab or rituximab doses received, median (range) | 10 (1-10) | 8 (1-8) |
| Patients with modifications to any obinutuzumab or rituximab dose* | 222 (31.5) | 210 (29.9%) |
| Patients with modifications to obinutuzumab or rituximab doses in cycle 1* | 192/702 (27.4) | 155/703 (22.0) |
| Day 1 | 39/651 (6.0) | 0 |
| Day 8 | 41/624 (6.6) | 0 |
| Day 15 | | |
| Patients with delays to obinutuzumab or rituximab doses of > 7 days | 92 (13.1) | 64 (9.1) |
| Patients with 90% planned dose intensity of obinutuzumab or rituximab | 671 (95.3) | 697 (99.1) |
| Patients with 90% planned dose intensity of | | |
| Cyclophosphamide | 642 (91.3) | 647 (92.0) |
| Doxorubicin | 631 (89.8) | 639 (90.9) |
| Prednisone | 662 (94.0) | 643 (91.5) |
| Vincristine | 642 (91.3) | 625 (88.9) |
| Duration of exposure to obinutuzumab or rituximab, weeks, median (range) | 25.3 (1-32) | 25.3 (0-32) |
| Cumulative dose of obinutuzumab or rituximab in mg, median (range) | 10,000 (998-10,065) | 5,133.5 (515-8,084) |

G-CHOP, obinutuzumab plus cyclophosphamide, doxorubicin, vincristine, and prednisone; R-CHOP, rituximab plus cyclophosphamide, doxorubicin, vincristine, and prednisone.
*Including interruptions to infusions and slowing of infusion rates.

TABLE 6

Number (and %) of Patients Reporting AEs of Any Grade With an Incidence
Rate of At Least 10% (At Preferred Term Level) in Either Treatment Arm,
Listed by System Organ Class and Preferred Term (Safety Population)

|  | G-CHOP (N = 704), No. (%) | R-CHOP (N = 703), No. (%) |
|---|---|---|
| Blood and lymphatic system disorders | | |
| Total number of patients with at least one AE | 451 (64.1) | 389 (55.3) |
| Neutropenia | 340 (48.3) | 286 (40.7) |
| Febrile neutropenia | 127 (18.0) | 108 (15.4) |
| Leukopenia | 115 (16.3) | 87 (12.4) |
| Anemia | 95 (13.5) | 99 (14.1) |
| Gastrointestinal disorders | | |
| Total number of patients with at least one AE | 428 (60.8) | 410 (58.3) |
| Nausea | 207 (29.4) | 199 (28.3) |
| Constipation | 165 (23.4) | 172 (24.5) |
| Diarrhea | 112 (15.9) | 92 (13.1) |
| Vomiting | 103 (14.6) | 74 (10.5) |
| General disorders and administration site conditions | | |
| Total number of patients with at least one AE | 420 (59.7) | 323 (45.9) |
| Fatigue | 137 (19.5) | 123 (17.5) |
| Pyrexia | 142 (20.2) | 83 (11.8) |
| Chills | 133 (18.9) | 37 (5.3) |
| Asthenia | 71 (10.1) | 76 (10.8) |
| Injury, poisoning and procedural complications | | |
| Total number of patients with at least one AE | 281 (39.9) | 204 (29.0) |
| Infusion-related reaction | 254 (36.1) | 165 (23.5) |
| Metabolism and nutrition disorders | | |
| Total number of patients with at least one AE | 202 (28.7) | 170 (24.2)) |
| Decreased appetite | 97 (13.8) | 71 (10.1) |
| Nervous system disorders | | |
| Total number of patients with at least one AE | 336 (47.7) | 299 (42.5) |
| Peripheral neuropathy | 88 (12.5) | 89 (12.7) |
| Headache | 75 (10.7) | 57 (8.1) |
| Psychiatric disorders | | |
| Total number of patients with at least one AE | 107 (15.2) | 83 (11.8) |
| Insomnia | 76 (10.8) | 58 (8.3) |
| Respiratory, thoracic and mediastinal disorders | | |
| Total number of patients with at least one AE | 232 (33.0) | 197 (28.0) |
| Cough | 83 (11.8) | 60 (8.5) |
| Skin and subcutaneous tissue disorders | | |
| Total number of patients with at least one AE | 226 (32.1) | 226 (32.1) |
| Alopecia | 145 (20.6) | 142 (20.2) |

AE, adverse event; G-CHOP, obinutuzumab plus cyclophosphamide, doxorubicin, vincristine, and prednisone/prednisolone; R-CHOP, rituximab plus cyclophosphamide, doxorubicin, vincristine, and prednisone/prednisolone.

TABLE 7

Summary of AEs of Particular Interest as Preferred Terms or Predefined Categories (Safety Population)

| | All grades | | Grades 3-5 | |
|---|---|---|---|---|
| Category | G-CHOP (N =704), No. (%) | R-CHOP (N =703), No. (%) | G-CHOP (N =704), No. (%) | R-CHOP (N =703), No. (%) |
| Infections* | 379 (53.8) | 310 (44.1) | 135 (19.2) | 109 (15.5) |
| Opportunistic infections† | 13 (1.8) | 15 (2.1) | 8 (1.1) | 9 (1.3) |
| Neutropenia‡ | 398 (56.5) | 338 (48.1) | 384 (54.5) | 324 (46.1) |
| Infusion-related reactions§ | 319 (45.3) | 223 (31.7) | 69 (9.8) | 24 (3.4) |
| Infusion-related reactions (antibody related)§ | 273 (38.8) | 174 (24.8) | 53 (7.5) | 16 (2.3) |
| Tumor lysis syndrome | 4 (0.6) | 4 (0.6) | 4 (0.6) | 4 (0.6) |
| Cardiac events¶ | 75 (10.7) | 53 (7.5) | 33 (4.7) | 20 (2.8) |
| Thrombocytopenia‖ | 55 (7.8) | 18 (2.6) | 31 (4.4) | 10 (1.4) |
| Second malignancies** | 15 (2.1) | 15 (2.1) | 12 (1.7) | 13 (1.8) |
| Hepatitis B reactivation†† | 16 (2.3) | 6 (0.9) | 2 (0.3) | 2 (0.3) |
| Progressive multifocal leukoencephalopathy | 1 (0.1) | 0 | 1 (0.1) | 0 |
| Gastrointestinal perforation‡‡ | 14 (2.0) | 8 (1.1) | 12 (1.7) | 8 (1.1) |
| Perforation events | 7 (1.0) | 7 (1.0) | 6 (0.9) | 7 (1.0) |

TABLE 7-continued

Summary of AEs of Particular Interest as Preferred Terms or Predefined Categories (Safety Population)

|  | All grades | | Grades 3-5 | |
|---|---|---|---|---|
| Category | G-CHOP (N =704), No. (%) | R-CHOP (N =703), No. (%) | G-CHOP (N =704), No. (%) | R-CHOP (N =703), No. (%) |
| Abscesses/other | 8 (1.1) | 2 (0.3) | 8 (1.1) | 2 (0.3) |
| Hemorrhagic events§§ | 65 (9.2) | 39 (5.5) | 23 (3.3) | 10 (1.4) |

AE, adverse event; G-CHOP, obinutuzumab plus cyclophosphamide, doxorubicin, vincristine, and prednisone/prednisolone; HBV, hepatitis B infection; MedDRA, Medical Dictionary for Regulatory Activities; R-CHOP rituximab plus cyclophosphamide, doxorubicin, vincristine, and prednisone/prednisolone.
*Any preferred term in the System Organ Class Infections and infestations.
†Standardized MedDRA query.
‡Neutropenia and associated complications reported as AEs, not including abnormal laboratory values.
§Related to any infused treatment and occurring during/within 24 hours of infusion.
¶Any preferred term in the System Organ Class Cardiac disorders.
**Any preferred term in the System Organ Class Neoplasms benign, malignant and unspecified (including cysts and polyps) that started 6 months after the first study drug intake.
††At least one of an increase in HBV DNA level of ≥100 IU/ml or an AE of hepatitis B reactivation.
‡‡Standardized MedDRA query, comprising perforation events (preferred terms in the System Organ Class Gastrointestinal disorders) and abscesses and other events (preferred terms in other System Organ Classes).
§§Standardized MedDRA query, comprising hemorrhagic cerebrovascular conditions, and hemorrhage (laboratory and non-laboratory terms).

EXAMPLE 1

General Materials and Methods

Description of the NanoString LST Assay

If not indicated to the contrary, the NanoString LST Assay was performed in the context of the invention in accordance with the manual of the distributor (NanoString Technologies, Inc., Seattle, Wash., USA). Further guidance as to the assay is provided in Scott (2014 and 2015 loc cit.).

Overview of COO Assay

NanoString's LST gene expression assay was developed to enable the identification of the COO subtypes on the nCounter® Analysis System. The nCounter® Gene Expression Assay together with the NanoString technology provide an ultra-sensitive and highly multiplexed method for detecting mRNAs with molecular barcodes called nCounter Reporter Probes without the use of reverse transcription or amplification (Geissloc. cit.). The detection of mRNA is based on digital detection and direct molecular barcoding of target molecules through the use of a color coded probe pair. The probe pair consists of a Reporter Probe, which carries the signal on its 5' end, and a Capture Probe. The color codes carry six positions and each position can be one of four colors, thus allowing for a large diversity of tags that can be mixed together in a single well for direct hybridization to the target and yet still be individually resolved and identified during data collection. The NanoString Reporter and Capture Probe Technology employs the reporter probe that carries the color-coded barcode and the capture probe that allows the complex to be immobilized for data collection.

Customized LST probe pairs are mixed with specimen RNA in massive excess to target mRNA to ensure that each target finds a probe pair. After hybridization, excess unbound probes are washed away, and the Target/Probe complexes are immobilized in the cartridge for data collection. Data Collection is carried out in the nCounter® Digital Analyzer. Digital images are processed and barcode counts are tabulated in a comma separated value (CSV) format ready for sample normalization and data analysis.

Prior to data analyses, each sample is normalized to the reference counts generated from the synthetic RNA reference control transcript and the house keeping genes.

Determination of COO Status in Patient Samples

The LST assay generates gene expression data for each patient for 20 genes (see Table 8). Five of these genes are housekeeping reference genes, while the 15 other genes distinguish GCB from ABC, specifically eight genes are known to be overexpressed in ABC-like DLBCL, and seven genes are known to be overexpressed in GCB-like DLBCL (based on Scott 2014 loc.cit.

TABLE 8

Twenty gene list in the NanoString LST Assay

| Type | Genes |
|---|---|
| Overexpressed in ABC-like DLBCL | TNFRSF13B; LIMD1; IRF4; CREB3L2; PIM2; CYB5R2; RAB7L1; CCDC50 |
| Housekeeping genes | R3HDM1; WDR55; ISY1; UBXN4; TRIM56MME; SERPINA9; ASB13; |
| Overexpressed in GCB-like DLBCL | MAML3; ITPKB; MYBL1; S1PR2 |

A Linear Predictor Score (LPS) is calculated for each patient based on the gene expression data. The LPS is a weighted sum of the gene expression of the 20 genes in the LST assay:

$$LPS(X) = \Sigma_j a_j X_j,$$

where $X_j$ the gene expression for gene j and $a_j$ is the coefficient for gene j.

The LPS for each patient is then compared against predefined thresholds to determine the DLBCL COO subtype for a patient. For an individual LPS score, a probability is determined as to whether the tumor is likely to be part of the ABC subtype or the GCB subtype. Tumors with a probability of being ABC greater than 90% are considered ABC, whereas those with a probability of being GCB of greater than 90% are considered GCB. Tumors with a probability of being ABC or of being GCB of less than 90%, are considered Unclassified (Scott 2014 and 2015 loc. cit.)

G-CHOP and R-CHOP Regimens

Patients will receive treatment with one of two immunochemotherapy regimens:
  G-CHOP (investigational arm): CHOP chemotherapy combined with obinutuzumab
  R-CHOP (control arm): CHOP chemotherapy combined with rituximab Obinutuzumab and rituximab are considered the investigational medicinal products for the purposes of this protocol.

In the investigational arm, obinutuzumab will be administered by IV infusion at an absolute (flat) dose of 1000 mg on Day 1 of each 21-day cycle for 8 cycles. During Cycle 1, obinutuzumab will also be infused on Days 8 and 15. Administration of obinutuzumab on days when both obinutuzumab and CHOP are to be given should be completed for at least 30 minutes before chemotherapy administration is started.

CHOP chemotherapy may be given on the next day after obinutuzumab administration if the duration of the obinutuzumab infusion necessitates administration of the CHOP infusion the next day. CHOP chemotherapy will be given for a maximum of 6 or 8 cycles, as described in Section 4.5.3.a and Table 5. If only 6 cycles of CHOP chemotherapy are to be administered (see Table 5), Cycles 7 and 8 of obinutuzumab will be given as monotherapy on an every-21-day schedule.

In the control arm of the study, rituximab at a dose of 375 mg/m² will be administered by IV infusion on Day 1 of each 21-day cycle for 8 cycles. Rituximab will be administered prior to CHOP, and the infusion should be completed and patients observed for at least 30 minutes prior to starting CHOP. CHOP may be given on Day 2 if the duration of rituximab infusion necessitates administration of the CHOP infusion the next day. If only 6 cycles of CHOP chemotherapy are to be administered (see Table 5), Cycles 7 and 8 of rituximab will be given as monotherapy on an every-21-day schedule.

The dose of the rituximab and chemotherapy should be calculated on the basis of a patient's body weight at the screening assessment (Day-14 to Day-1). For changes>10% in body weight from screening for all subsequent doses, the doses of rituximab and chemotherapy should be modified accordingly. The weight that triggered a dose adjustment will be taken as the new reference weight for future dose adjustments. As noted in Section 3.6.1.c, the use of G-CSF is recommended according to ASCO, EORTC, and ESMO guidelines for patients who are 60 years old and those with co-morbidities. It is strongly recommended in Cycle 1 for all patients treated with G-CHOP.

Obinutuzumab (technical data)

a Formulation

Obinutuzumab is provided as a single-dose, sterile liquid formulation in a 50-mL pharmaceutical grade glass vial containing a nominal 1000 mg of obinutuzumab (G3 material). The formulated drug product consists of 25 mg/mL drug substance (G3) formulated in histidine, trehalose, and poloxamer 188. The vial contains 41 mL (with 2.5% overfill).

For further details, see the Obinutuzumab Investigator's Brochure.

b Handling and Storage

The recommended storage conditions for the obinutuzumab drug product are between 2° C. and 8° C. protected from light. Chemical and physical in-use stability for obinutuzumab dilutions in 0.9% sodium chloride (NaCl) have been demonstrated for 24 hours at 2° C.-8° C. and at ambient temperature and ambient room lighting. The prepared diluted product should be used immediately. If not used immediately, in-use storage times and conditions prior to use are the responsibility of the user and would normally not be longer than 24 hours at 2° C.-8° C. Obinutuzumab should not be frozen or shaken. Mix gently. All transfer procedures require strict adherence to aseptic techniques. Do not use an additional in-line filter because of potential adsorption. For further details, see the Obinutuzumab Investigator's Brochure.

c Obinutuzumab Dose and Schedule

Obinutuzumab will be administered by IV infusion as an absolute (flat) dose of 1000 mg on Day 1 of each 21-day cycle for 8 cycles. Obinutuzumab will be administered prior to CHOP, and patients should be observed 30 minutes prior to starting CHOP. If CHOP is not completed on Day 1 because of the long duration of obinutuzumab therapy, CHOP chemotherapy may be administered on Day 2. During Cycle 1, obinutuzumab will also be infused on Days 8 and 15. If CHOP chemotherapy is not given at Cycles 7 and 8, obinutuzumab will be administered as monotherapy.

d Obinutuzumab Preparation

Obinutuzumab drug product intended for IV infusion is prepared by dilution of the drug product into an infusion bag containing 0.9% NaCl to the final drug concentration of 4 mg/mL. Using a 250-mL infusion bag containing 0.9% NaCl, withdraw and discard 40 mL of the sodium chloride. Withdraw 40 mL of obinutuzumab from a single glass vial and inject into the infusion bag (discard any unused portion of obinutuzumab left in the vial). Gently invert the infusion bag to mix the solution; do not shake.

Administration sets with polyvinyl chloride (PVC), polyurethane (PUR), or polyethylene as product contact surface and IV bags with polyolefine, polypropylene (PP), PVC, or polyethylene, as product contact surface are compatible and may be used.

Do not use obinutuzumab beyond the expiration date stamped on the carton.

e Obinutuzumab Administration

Obinutuzumab should be administered to patients in a clinical setting (inpatient or outpatient), where full emergency resuscitation facilities are immediately available and patients should be under close supervision of the investigator at all times. Do not administer as an IV push or bolus. After the end of the first infusion, the IV line or central venous catheter should remain in place for 2 hours in order to be able to administer IV drugs if necessary. If no adverse events occur after 2 hours, the IV line may be removed or the central venous catheter may be de-accessed. For subsequent infusions, access (either through an IV line or central venous catheter) should remain in place for at least 1 hour from the end of infusion, and if no adverse events occur after 1 hour, the IV access may be removed.

Please refer to Section 4.3.5, General Precautions (for guidance on the use of pre-medication and prophylaxis of tumor lysis syndrome), prior to administration of obinutuzumab. Instructions for the first and subsequent infusions of obinutuzumab are presented in Table 1.

TABLE 9

Administration of First and Subsequent Infusions of Obinutuzumab

| First Infusion (Day 1) | Subsequent Infusions |
|---|---|
| Begin infusion at and initial rate of 50 mg/hr. If no infusion reaction occurs, increase the infusion rate in 50-mg/hr increments every 30 minutes, to a maximum of 400 mg/hr. If an infusion reaction develops, stop or slow the infusion. Administer infusion-reaction medications and supportive care in accordance with institutional protocol. Resume the infusion at a 50% reduction in rate (the rate being used at the time that the hypersensitivity or infusion-related reaction occurred) if the reaction has resolved. | If a patient experienced an infusion reaction during the prior infusion, start at the same rate as the first infusion (50 mg/hr) and follow directions as noted. If the patient tolerated the prior infusion well (defined as an absence of Grade 2 reactions during a final infusion rate of 100 mg/hr), begin the infusion at a rate of 100 mg/hr. If no infusion reaction occurs, increase the infusion rate in 100-mg/hr increments every 30 minutes, to a maximum of 400 mg/hr. If an infusion reaction develops, stop or slow the infusion. Administer infusion-reaction medications and supportive care in accordance with institutional protocol. Resume the infusion at a 50% reduction |

TABLE 9-continued

Administration of First and Subsequent Infusions of Obinutuzumab

| First Infusion (Day 1) | Subsequent Infusions |
|---|---|
| | in rate (the rate being used at the time that the hypersensitivity or infusion-related reaction occurred) if the reaction has resolved. |

Obinutuzumab should be given as a slow IV infusion through a dedicated line. IV infusion pumps should be used to control the infusion rate of obinutuzumab. Do not administer as an IV push or bolus.

On days when both obinutuzumab and CHOP are given, obinutuzumab will be administered prior to CHOP and patients should be observed 30 minutes prior to starting CHOP. CHOP chemotherapy may be administered the next day if it cannot be given on the same day as obinutuzumab administration. Prior to each obinutuzumab infusion that is given in combination with CHOP (Day 1 of Cycles 1-6 or Cycles 1-8), patients should take the Day 1 dose of oral prednisone (100 mg) specified for each cycle of the CHOP regimen. The prophylactic use of corticosteroids (e.g., 100 mg of IV prednisolone or equivalent) may also be considered for patients thought to be at high risk for IRRs, if deemed appropriate by the investigator, and should be also administered prior to the obinutuzumab infusion.

For management of IRRs and anaphylaxis, see Section 4.3.6.a and Table 3.

CHOP Chemotherapy

CHOP is considered standard therapy for treatment of DLBCL. By center choice, sites will elect prior to study start whether they will be administering 8 cycles or 6 cycles of CHOP chemotherapy.

a Dosage and Administration

CHOP chemotherapy consists of IV cyclophosphamide, IV doxorubicin, vincristine administered by IV push, and oral prednisone or prednisolone. Standard CHOP will be administered for six to eight 21-day cycles. CHOP chemotherapy at Cycles 7 and 8 is to be administered according to a center's prospective choice for 6 versus 8 planned cycles.

Cyclophosphamide 750 mg/m$^2$ administered intravenously on Day 1

Doxorubicin 50 mg/m$^2$ administered intravenously on Day 1

Vincristine 1.4 mg/m$^2$ administered by IV push on Day 1 with a recommended cap of 2.0 mg Prednisone 100 mg/day orally (PO) on Days 1-5

Note: The dose of prednisone follows the National Comprehensive Cancer Network's recommendations (2010), which were based on Cruzman et al. 1999; Hiddemann et al. 2005. Prednisone may be replaced with prednisolone (1:1-conversion, 100 mg) in countries where prednisone is not available or is not the therapy of choice or it may be replaced with 80 mg methylprednisolone in countries or sites that do not have access to prednisone/prednisolone.

CHOP will be administered according to the standard preparation and infusion procedures at each investigational site and after the rituximab or obinutuzumab infusion. Refer to the specific package inserts for preparation, administration, and storage guidelines. At the discretion of the investigator, the dose of vincristine may be capped at 2 mg. For patients who are ≥70 years old, the dose of vincristine may be capped at 1.5 mg. BSA may be capped at 2 m$^2$ per institutional standards.

When obinutuzumab or rituximab and CHOP are scheduled to be administered on the same day, it is recommended that prednisone (100 mg) be given prior to the obinutuzumab or rituximab infusion. Obinutuzumab or rituximab administration should be completed at least 30 minutes prior to administration of the CHOP (cyclophosphamide, vincristine, and adriamycin) infusions. If it is the strong preference of the investigator or of the site (e.g., for logistical reasons), the administration of rituximab or obinutuzumab is allowed one day prior to administration of CHOP with pre-medication (defined in Section 4.3.5). It is also allowed to split the antibody (rituximab or obinutuzumab) infusion over 2 days if the patient is at increased risk for an IRR (high tumor burden, high peripheral lymphocyte count). Also, in patients who experience an adverse event during obinutuzumab or rituximab infusion, administration of obinutuzumab may be continued on the following day if needed. If Cycle 1 Day 1 dose of obinutuzumab is split, both infusions must happen with appropriate pre-medication and at the First Infusion Rate (Please see Table 2). If CHOP is started later than the Day 1 of the cycle, then planned Day 1 of the next cycle should be calculated from the day when CHOP was actually initiated, in order to maintain the regular chemotherapy interval of 21 days.

EXAMPLE 2

Obinutuzumab or Rituximab (plus CHOP) in Previously Untreated DLBCL (Description of the Roche GOYA (B021005) Clinical Phase 3 Study)

Patients

Eligible patients were aged 18 years with: previously-untreated, histologically documented, CD20-positive DLBCL (as assessed by local pathology laboratory); 1 bi-dimensionally measurable lesion (>1.5 cm largest dimension on computed tomography [CT] scan); Eastern Cooperative Oncology Group performance status of 0-2; adequate hematologic, liver, and kidney function; left ventricular ejection fraction ≥50%; and an International Prognostic Index (IPI) score of 2 (and patients with an IPI score of 1 aged ≤60 years, with or without bulky disease, and those with an IPI score of 0 and bulky disease, ie, one lesion 7.5 cm). Full inclusion/exclusion criteria are detailed below. All patients provided written informed consent.

Full Inclusion and Exclusion Criteria

Patients had to meet the following criteria for study entry:
1. Written informed consent.
2. Previously untreated CD20-positive diffuse large B-cell lymphoma (DLBCL) histologically documented using the following:
    a. The pathology report must be available for review and a tissue block sent for retrospective central confirmation.
    b. Formalin-fixed paraffin-embedded tissue blocks are preferred; however, in countries using a different fixative, any tissue block available will be accepted and notation of the type of fixative included.
  c. If a tissue block is not available, 15 unstained slides (3-5 μm in thickness) will be accepted.
  d. The optional Roche clinical repository sample and required exploratory biomarker samples will be obtained from the same tissue block. If central confirmation is unable to be performed on submitted material, stained slides used for diagnosis may also be requested.
3. Patients in an International Prognostic Index (IPI) disease risk group that is one of the following: high, high-intermediate, or low-intermediate.
  a. Patients in the low-risk group are eligible but must have an IPI score of 1, irrespective of bulky disease, or IPI score of 0 with bulky disease, defined as one lesion ≥7.5 cm.
  b. Note: patients with IPI 1 due to age alone (ie, patients >60 years old with no other risk factors) with no bulky disease are not eligible for this trial.
4. At least one bi-dimensionally measurable lesion defined as >1.5 cm in its largest dimension on computed tomography scan.
5. Ability and willingness to comply with the study protocol procedures.
6. Age 18 years.
7. Eastern Cooperative Oncology Group performance status of 0, 1, or 2.
8. Left ventricular ejection fraction 50% on cardiac multiple-gated acquisition scan or cardiac echocardiogram.
9. Adequate hematologic function (unless due to underlying disease, as established by extensive bone marrow involvement or due to hypersplenism secondary to the involvement of the spleen by DLBCL per the investigator) defined as follows:
  a. Hemoglobin≥9 g/dl;
  b. Absolute neutrophil count≥1.5×10$^9$/l;
  c. Platelet count≥75×10$^9$/l.
10. For men who are not surgically sterile: agreement to use a barrier method of contraception during the treatment period and until ≥3 months after the last dose of obinutuzumab or rituximab, or according to institutional guidelines for CHOP chemotherapy, whichever is longer, and agreement to request that their partners use an additional method of contraception, such as oral contraceptives, intrauterine device, barrier method, or spermicidal jelly.
11. For women of reproductive potential who are not surgically sterile: agreement to use two adequate methods of contraception, such as oral contraceptives, intrauterine device, or barrier method of contraception in conjunction with spermicidal jelly during the treatment period and until ≥12 months after the last dose of obinutuzumab or rituximab, or according to institutional guidelines for CHOP chemotherapy, whichever is longer.

Patients who met any of the following criteria were excluded from study entry:
1. History of severe allergic or anaphylactic reactions to humanized or murine monoclonal antibodies, or known sensitivity or allergy to murine products or to any component of CHOP or obinutuzumab.
2. Contraindication to any of the individual components of CHOP, including prior receipt of anthracyclines.
3. Patients with transformed lymphoma and patients with stage 3b follicular lymphoma.
4. Prior therapy for DLBCL, with the exception of nodal biopsy or local irradiation.
5. Prior treatment with cytotoxic drugs or rituximab for another condition (eg, rheumatoid arthritis) or prior use of an anti-CD20 antibody.
6. Prior use of any monoclonal antibody within 3 months of the start of cycle 1.
7. Corticosteroid use>30 mg/day of prednisone or equivalent, for purposes other than lymphoma symptom control.
  a. Patients receiving corticosteroid treatment with ≤30 mg/day of prednisone or equivalent must be documented to be on a stable dose of at least 4 weeks' duration prior to randomization (cycle 1, day 1).
  b. If glucocorticoid treatment is urgently required for lymphoma symptom control prior to the start of study treatment, prednisone 100 mg or equivalent could be given for a maximum of 5 days, but all tumor assessments must be completed prior to start of glucocorticoid treatment.
8. Primary central nervous system (CNS) lymphoma and secondary CNS involvement by lymphoma, mantle cell lymphoma, or histologic evidence of transformation to a Burkitt lymphoma, primary mediastinal DLBCL, primary effusion lymphoma, plasmablastic lymphoma, and primary cutaneous DLBCL.
9. Vaccination with live vaccines within 28 days prior to randomization.
10. Any investigational therapy within 28 days prior to the start of cycle 1.
11. History of other malignancy that could affect compliance with the protocol or interpretation of results.
  a. Patients with a history of curatively treated basal or squamous cell carcinoma, or melanoma of the skin or in-situ carcinoma of the cervix at any time prior to the study are eligible.
  b. Patients with any other malignancy that has been treated with surgery alone with curative intent and the malignancy has been in remission without treatment for 5 years prior to enrollment are eligible.
12. Evidence of significant, uncontrolled concomitant diseases that could affect compliance with the protocol or interpretation of results, including significant cardiovascular disease (such as New York Heart Association Class III or IV cardiac disease, myocardial infarction within the last 6 months, unstable arrhythmias, or unstable angina) or pulmonary disease (including obstructive pulmonary disease and history of bronchospasm).
13. Recent major surgery (within 4 weeks prior to the start of cycle 1), other than for diagnosis.
14. Any of the following abnormal laboratory values (unless any of these abnormalities are due to underlying lymphoma):
  a. Creatinine>1.5 times the upper limit of normal (ULN; unless creatinine clearance normal), or calculated creatinine clearance<40 ml/min (using the Cockcroft-Gault formula).
  b. Aspartate amino transferase or alanine amino transferase>2.5×the ULN.
  c. Total bilirubin≥1.5×the ULN: Patients with documented Gilbert disease may be enrolled if total bilirubin is ≤3.0×the ULN.
  d. International normalized ratio>1.5×the ULN in the absence of therapeutic anticoagulation.

e. Partial thromboplastin time or activated partial thromboplastin time>1.5×the ULN in the absence of a lupus anticoagulant.
15. Known active bacterial, viral, fungal, mycobacterial, parasitic, or other infection (excluding fungal infections of nail beds) or any major episode of infection requiring treatment with intravenous antibiotics or hospitalization (relating to the completion of the course of antibiotics except if for tumor fever) within 4 weeks prior to the start of cycle 1.
16. Patients with suspected active or latent tuberculosis.
    a. Latent tuberculosis needs to be confirmed by positive interferon-gamma release assay.
17. Positive test results for chronic hepatitis B infection (defined as positive HBsAg serology).
    a. Patients with occult or prior hepatitis B infection (defined as positive total hepatitis B core antibody and negative HBsAg) may be included if HBV DNA is undetectable. These patients must be willing to undergo monthly DNA testing.
18. Positive test results for hepatitis C (HCV antibody serology testing).
    a. Patients positive for HCV antibody are eligible only if polymerase chain reaction is negative for HCV RNA.
19. Known history of HIV seropositive status.
    a. For patients with unknown HIV status, HIV testing will be performed at screening if required by local regulations.
20. Positive results for the human T-lymphotrophic 1 virus (HTLV).
    a. HTLV testing is required for patients at sites in endemic countries (Japan and Melanesia, and countries in the Caribbean basin, South America, Central America, and sub-Saharan Africa).
21. Patients with a history of confirmed progressive multifocal leukoencephalopathy.
22. Pregnancy or lactation.
23. Life expectancy of <12 months.

Study Design and Treatments

GOYA is a multicenter, open-label, randomized, phase 3 study. Patients were randomized (1:1 ratio) to receive eight 21-day cycles of either G (1000 mg intravenously [IV] on days 1, 8, and 15 of cycle 1, and on day 1 of cycles 2-8), or R (375 mg/m$^2$ IV on day 1, cycles 1-8), plus 6 or 8 cycles of CHOP at the following doses: cyclophosphamide 750 mg/m$^2$ IV (day 1); doxorubicin 50 mg/m$^2$ IV (day 1); vincristine 1.4 mg/m$^2$ IV (day 1, maximum 2.0 mg); and prednisone 100 mg/day orally (days 1-5). The number of CHOP cycles for both arms was agreed in advance with each study site; if only 6 CHOP cycles were administered, antibody was administered as monotherapy during cycles 7-8. Pre-planned radiotherapy at initial sites of bulky or extranodal disease was permitted within 8 weeks of day 1 of the last antibody cycle and after completion of end-of-treatment assessments. Details of pre-medications, permitted concomitant therapies, and permitted reasons for dose delays/reductions are given in the Supplementary Appendix. Randomization was via an interactive voice-response system with stratification according to the number of planned chemotherapy cycles (6/8 cycles of CHOP), IPI score, and geographic region (Western Europe, Eastern Europe, South and Central America, North America, and Asia and others).

GOYA was conducted in accordance with the European Clinical Trial Directive (for European centers) and International Conference on Harmonization guidelines for Good Clinical Practice. The protocol was approved by the ethics committees of participating centers and was registered at ClinicalTrials.gov (NCT01287741).

Pre-Medications, Dose Alterations, and Permitted Therapies

All patients received pre-medication with oral acetaminophen and an antihistamine before administration of obinutuzumab (G) or rituximab (R). It was recommended that cyclophosphamide, doxorubicin, vincristine, and prednisone (CHOP) administration be started at least 30 minutes after administration of G or R. In each cycle when G or R was given with CHOP, the day 1 dose of oral prednisone was administered before the antibody infusion. Additional glucocorticoid therapy could also be administered to patients considered at high risk of infusion-related reactions. Tumor lysis prophylaxis (adequate hydration and allopurinol) was recommended for patients with high tumor burden and who were considered to be at risk of tumor lysis. Treatment doses were delayed for up to 2 weeks in the event of grade 3 or 4 hematologic toxicity or grade 2-4 non-hematologic toxicity; if toxicity did not resolve, the patient was withdrawn from study treatment. Dose reductions were allowed for chemotherapy, but not for G or R.

Prophylaxis with G-CSF was recommended for patients aged 60 years and/or with co-morbidities and during cycle 1 for all patients in the G-CHOP arm. G-CSF was also permitted for the treatment of neutropenia. Use of chemotherapy (other than CHOP), immunotherapy, hormone therapy (other than contraceptives, hormone-replacement therapy, or megestrol acetate), and any therapies intended for the treatment of lymphoma was prohibited (for radiotherapy, see main text).

Study Endpoints and Assessments

The primary study endpoint was investigator-assessed progression-free survival (PFS), defined as the time from the date of randomization until the first occurrence of disease progression, relapse, or death from any cause. To rule out bias and support the primary analysis, PFS was also assessed by an Independent Review Committee (IRC). Secondary endpoints included overall survival (OS), event-free survival (EFS), CR rate, overall response rate (ORR, including CR and partial response), disease-free survival (DFS), duration of response, time to next anti-lymphoma treatment (TTNT), and safety. PFS was also analyzed in DLBCL cell-of-origin (COO) subgroups (germinal-center B-cell-like [GCB], activated B-cell-like [ABC], and unclassified; exploratory analysis). COO classification was based on gene-expression profiling using the NanoString Research Use Only Lymphoma Subtyping Test (NanoString Technologies, Inc., Seattle, Wash., USA). Tumor response and progression were assessed by the investigator using regular clinical and laboratory examinations and CT scans, according to the Revised Response Criteria for Malignant Lymphoma (Cheson, J Clin Oncol 25, 2007, 579-586). For those patients with $^{18}$F-fludeoxyglucose positron emission tomography (FDG-PET) scans (mandatory at sites with a PET scanner), a separate response assessment was performed incorporating the FDG-PET results. Primary endpoint analysis was based on the assessment of all patients using conventional CT scan. Response was evaluated 4-8 weeks (CT) or 6-8 weeks (FDG-PET) after last study treatment, or sooner in case of early discontinuation.

Safety was assessed by monitoring and recording all adverse events (AEs) and serious AEs (SAEs), including abnormalities identified from laboratory evaluations, vital sign measurement, and physical examination. AEs were graded using National Cancer Institute Common Terminology Criteria for Adverse Events v4.0. Laboratory safety assessments included routine hematology and blood chemistry, and tests of immunologic parameters. An independent data monitoring committee (IDMC) performed periodic safety reviews.

Statistical Analysis

Sample size was calculated to allow detection of a 25% reduction in the risk of disease progression, relapse, or death with G-CHOP versus R-CHOP (ie, a PFS hazard ratio [HR] for G-CHOP over R-CHOP of 0.75), with a two-sided alpha level of 0.05 and 80% power. To achieve this, and allowing for an annual dropout rate of 5%, 405 PFS events were needed for the primary analysis, requiring enrollment of 1,400 patients over 3 years.

Efficacy assessments were performed on the intent-to-treat (ITT) population, comprising all randomized patients. The safety analysis population included all patients who received any study drug (antibody or CHOP). Treatment comparison of PFS was performed using a two-sided level 0.05 stratified log-rank test. The Kaplan-Meier method was used to estimate PFS distribution for each treatment arm. Estimates of treatment effect were expressed as HRs using a stratified Cox proportional-hazards analysis, including 95% confidence intervals (Cis).

The IDMC evaluated efficacy and safety at three formal interim analyses; two for futility and one for efficacy. Pre-planned subgroup analyses assessed the effect of selected baseline patient characteristics, including COO subtype, on PFS.

Results

Overview

After 29 months' median observation, the number of investigator-assessed PFS events was similar with G (201, 28.5%) and R (215, 30.2%); stratified hazard ratio was 0.92 (95% confidence interval, 0.76 to 1.11; P=0.39); 3-year PFS rates were 70% and 67%, respectively. Secondary endpoints of independently-reviewed PFS, other time-to-event endpoints, and tumor response rates were similar between arms. In exploratory subgroup analyses, patients with germinal-center B-cell-like subtype had a better PFS than activated B-cell-like, irrespective of treatment. Frequencies of grade 3-5 adverse events (AEs; 73.7% vs. 64.7%) and serious AEs (42.6% vs. 37.6%) were higher with G-CHOP. Fatal AE frequencies were 5.8% for G-CHOP and 4.3% for R-CHOP. The most common AEs were neutropenia (G-CHOP, 48.3%; R-CHOP, 40.7%), infusion-related reactions (36.1%; 23.5%), nausea (29.4%; 28.3%), and constipation (23.4%; 24.5%).

Patient Characteristics and Treatment

Figure 1:
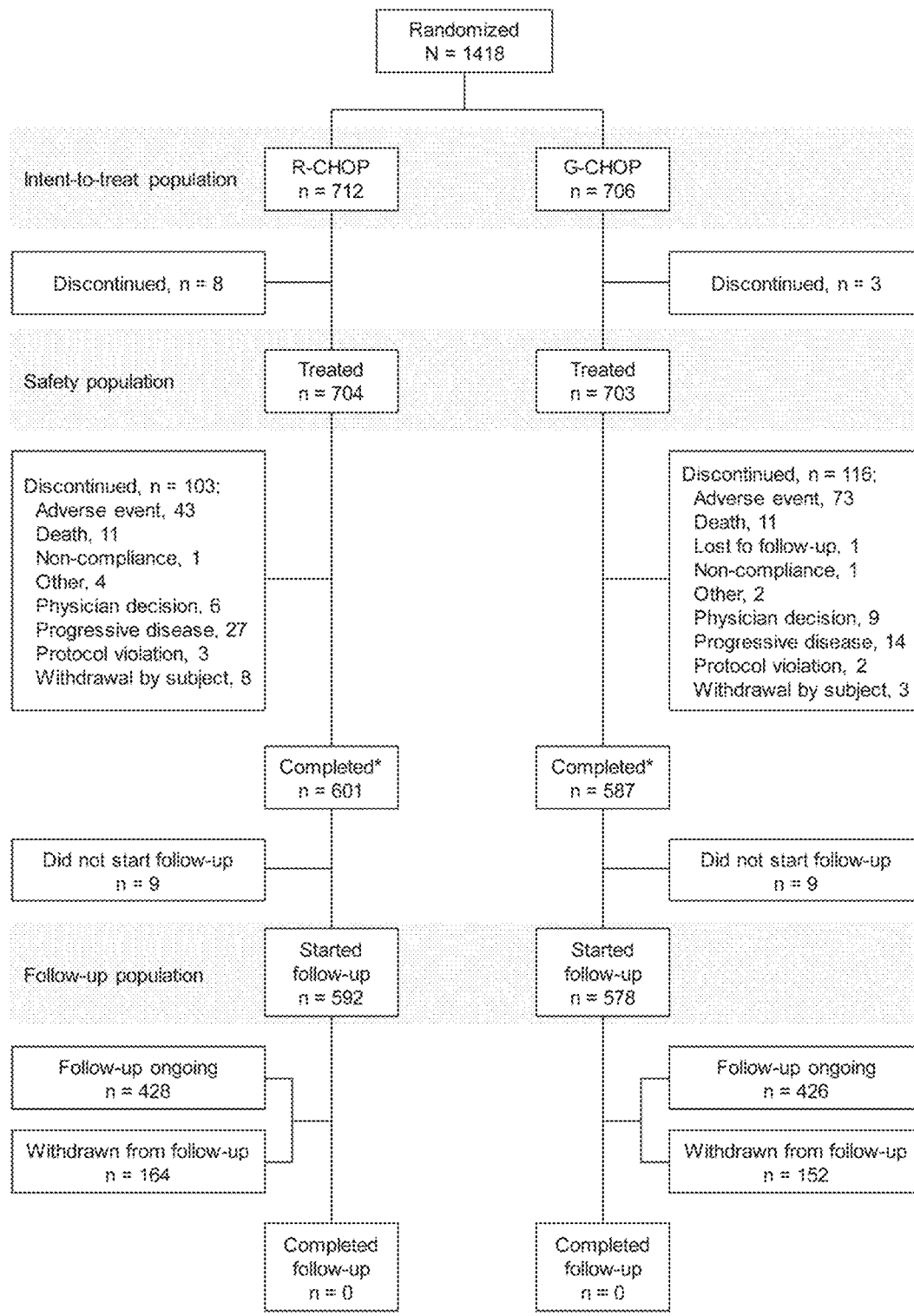
FIG. 1

Patients were enrolled at 207 centers in 29 countries. A total of 1,418 patients were randomized between July 2011 and June 2014 to receive either G-CHOP (n=706) or R-CHOP (n=712), and 1,188 patients (G-CHOP, 587; R-CHOP, 601) completed planned treatment (FIG. 1). AEs were the main reason for study (antibody) treatment discontinuation in both arms, and this was reported more frequently in the G-CHOP arm. Study (antibody) treatment discontinuation as a result of progressive disease was approximately twice as frequent in the R-CHOP arm compared with the G-CHOP arm.

Demographic and baseline disease characteristics were well balanced between the two arms (Table 1). COO subgroup information was available for 933 patients; distribution by subtype was well-balanced and there were no clinically relevant differences between arms within COO subtypes. The reasons for missing COO information were: a restricted Chinese sample export license precluding biomarker assessments (n=252), CD20-positive DLBCL not confirmed by central laboratory (n=102; note that these patients were balanced between treatment arms: G-CHOP, n=53; R-CHOP, n=49), and missing/inadequate tissue (n=131). Median duration of exposure was 25.3 (range, 1-32) weeks for G and 25.3 (0-32) weeks for R. The dose intensity of G and R exceeded 90% for 95.3% and 99.1% of patients, respectively. Most patients in both arms (>88%) received more than 90% of the planned dose of each CHOP component. Antibody dose delays were more common in the G-CHOP arm: at least one delay of 5, 7 days (G-CHOP, 34.9%; R-CHOP, 30.0%) and of >7 days (G-CHOP, 13.1%; R-CHOP, 9.1%) (Table 5). New (unplanned) anti-lymphoma treatment was received by 103 patients (G-CHOP, 49; R-CHOP, 54) before disease progression, including radiotherapy for 23 patients with signs of residual disease after study treatment completion (G-CHOP, 9; R-CHOP, 14), and 227 patients (G-CHOP, 102; R-CHOP, 125) after disease progression.

Efficacy

As of Apr. 30, 2016, and after 29 months' median observation, the number of investigator-assessed PFS events in the ITT population was similar for G-CHOP (201, 28.5%) and R-CHOP (215, 30.2%), with stratified HR, 0.92 (95% CI, 0.76 to 1.11; P=0.3868). Estimated 3-year PFS rates were 69.6% and 66.9%, respectively (FIG. 2A; Table 2).

Figure 13:
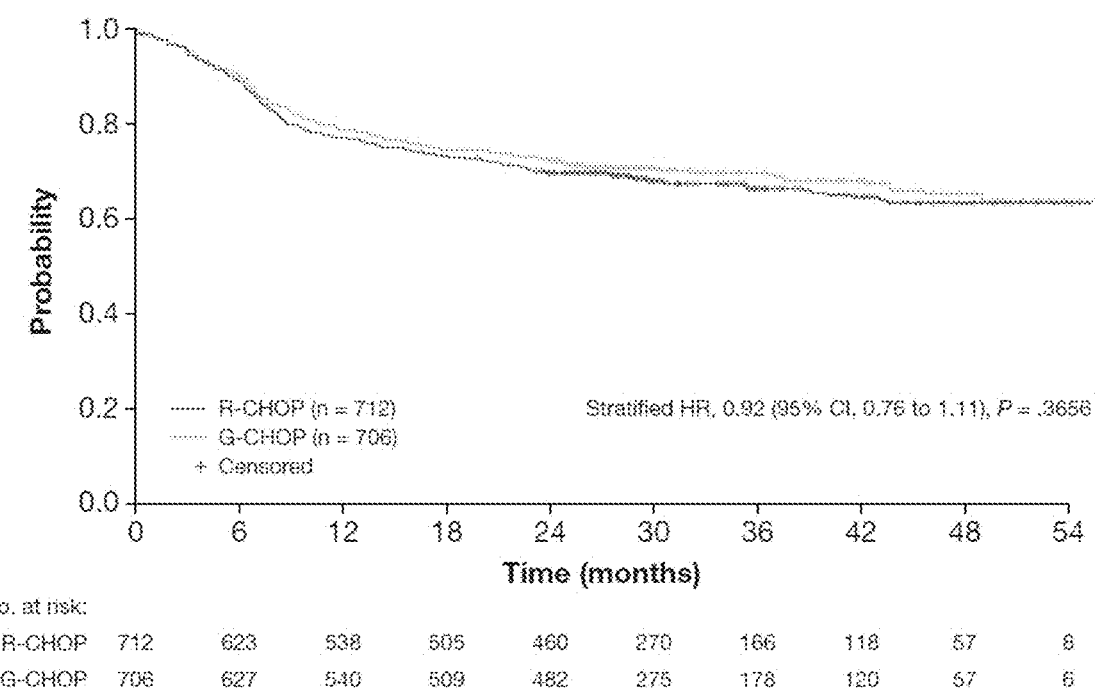

Secondary endpoints were consistent with the primary endpoint, with no clinically meaningful differences between treatment arms for IRC-assessed PFS or any other time-to-event endpoint (OS, EFS, DFS, and TTNT) (FIG. 2B, Table 2, FIG. 13).

Subgroup and Exploratory Analyses

The efficacy of G-CHOP versus R-CHOP (unstratified HR for investigator-assessed PFS) was generally similar across selected patient subgroups, including patients who received 6 versus 8 cycles of CHOP (FIG. 3).

Kaplan-Meier analysis of PFS in patients with different COO subtypes (irrespective of study treatment) suggested that the GCB subtype is associated with a better outcome than ABC or unclassified subtypes. The HRs for PFS were 1.71 (95% CI, 1.31 to 2.23) for the ABC-GCB comparison, 1.57 (95% CI, 1.14 to 2.15) for the unclassified-GCB comparison and 1.08 (95% CI 0.77 to 1.52) for the ABC-unclassified comparison (FIG. 2C); 3-year PFS rates were 75%, 59%, and 63% for the GCB, ABC, and unclassified subtypes, respectively. In an exploratory analysis of investigator-assessed PFS, the stratified HR for G-CHOP relative to R-CHOP for the 933 patients with available COO data was 0.82 (95% CI, 0.64 to 1.04), suggesting a potential selection bias vs. the ITT population. The stratified HR for 540 patients in the GCB COO subgroup was 0.72 (95% CI, 0.51 to 1.03; 3-year PFS, 79% [G-CHOP] vs. 71% [R-CHOP]); no clinically meaningful differences in PFS between treatment groups were seen in the 243 patients with ABC subtype (HR, 0.86 [95% CI, 0.57 to 1.29]; 3-year PFS, 61% vs. 58%])) or 150 patients with unclassified COO subtype (HR, 1.02 [95% CI, 0.60 to 1.75]; 3-year PFS, 62% vs. 64%]; FIG. 14).

Safety

In the safety population, the proportion of patients experiencing at least one AE of any grade was similar in the G-CHOP and R-CHOP arms (97.0% [683/704] and 93.5% [657/703], respectively) (Table 3). The most common AEs in both arms were neutropenia (G-CHOP, 48.3%; R-CHOP, 40.7%), infusion-related reactions (IRRs; 36.1%; 23.5%), nausea (29.4%; 28.3%), and constipation (23.4%; 24.5%) (Table 6). Grade 3-5 AEs were more common in the G-CHOP arm (73.7% [519/704] vs. 64.7% [455/703]), as were SAEs (42.6% [300/704] vs. 37.6% [264/703]). The most common grade 3-5 AEs in both arms were neutropenia (G-CHOP, 46.2%; R-CHOP, 38.1%), infections (19.2%; 15.5%), febrile neutropenia (17.5%; 15.2%), and leukopenia (13.6%; 10.1%) (Table 3).

Analysis of AEs of particular interest showed that infections, neutropenia, IRRs, cardiac events, thrombocytopenia, and hemorrhagic events of any grade (as well as grade 3-5 AEs and SAEs) were more common with G-CHOP than R-CHOP (Table 7). Of note, rates of hepatitis B reactivation were higher with G-CHOP (2.3%) than R-CHOP (0.9%), the majority of events were grade 1 or 2, and grade 3 or 4 events were well balanced between the two arms (G-CHOP 0.3% vs R-CHOP 0.3%). All other AE groups of particular interest, namely opportunistic infections, tumor lysis syndrome, secondary malignancies, and gastrointestinal perforation (excluding abscesses) occurred at similar frequencies in the two arms (Table 7).

A similar proportion of patients in each arm received at least one dose of G-CSF during the study (G-CHOP, 611 [86.5%]; R-CHOP, 586 [82.3%]).

A higher proportion of patients in the G-CHOP arm than in the R-CHOP arm discontinued 1 component of the study treatment due to an AE (84 [11.9%] vs. 60 [8.5%]). Fatal AEs were experienced by 71 patients (G-CHOP, 5.8% [41/704]; R-CHOP, 4.3% [30/703]) and are detailed in Table 3.

Discussion

In the current study of patients with previously untreated DLBCL, G-CHOP and R-CHOP demonstrated similar efficacy for all time-to-event endpoints, and the primary study endpoint of investigator-assessed PFS was not met. The lack of superiority of G-CHOP over R-CHOP in a population with aggressive NHL contrasts with the results of studies evaluating G in CLL and FL. In the GALLIUM study, G-based induction and maintenance therapy significantly improved investigator-assessed PFS relative to R-based therapy in 1,202 previously untreated FL patients (Marcus loc. cit.). G also prolonged PFS relative to R in untreated CLL patients (n=663) when both were combined with chlorambucil in the phase 3 CLL11 study (Goede loc. cit.).

Given the advantages of G-based therapy in FL and CLL patients, the lack of benefit of G-CHOP in DLBCL patients in GOYA was unexpected.It might simply have resulted from the differences in biologic and clinical profiles between indolent lymphoproliferative diseases, such as FL and CLL, and aggressive ones, such as DLBCL (Lenz, N. Engl. J. Med. 362, 2010, 1417-1429; Lim loc. cit.). Indeed, obinutuzumab may be more beneficial in lymphomas that are less aggressive or, like FL, are derived from the germinal center. The trend towards a benefit of G-CHOP over R-CHOP in GOYA for the GCB subtype, which is derived from the germinal center and is known to be more like FL compared to other DLBCL subtypes (Morin, Nature 476 2011, 298-303; Shaffer, Nat. Rev. Immunol. 2, 2002, 920-932), with a more favorable prognosis and different immune microenvironment than the ABC and unclassified subtypes, appears to support this finding. The different mode of action of obinutuzumab and rituximab may also play a role in the differential benefit of these agents in FL and DLBCL, however, no data are yet available to support this statement. Ongoing analyses of GOYA biomarker data will provide further insight into these differences. Notably, dose interruptions and skipped doses in cycle 1 were more frequent with G-CHOP, reflecting a higher rate of AEs (IRRs and cytopenias); this might have contributed to the lack of efficacy benefit compared with R-CHOP.

Since the dramatic improvement in outcomes after rituximab was first added to CHOP (Coiffier loc. cit.), no major advances have been made in the management of DLBCL patients. Randomized trials failed to show a benefit of shortening intervals between cycles (Cunningham, Lancet 381, 2013, 1817-1826), or from consolidation with high-dose chemotherapy and autologous stem cell transplantation (Stiff, N. Engl. J. Med. 369, 2013, 1681-1690; Schmitz, Lancet Oncol 13, 2012, 1250-1259); the addition of bortezomib to R-CHOP also failed to improve outcomes in a randomized trial of patients with non-GCB DLBCL (Leonard, Blood 126, 2015, 811), and maintenance with lenalidomide did not improve OS (Thieblemont, Blood 128, 2016, 471). Given the aggressive behavior of DLBCL, the substitution of rituximab by a new anti-CD20 antibody with a different mode of action may not be sufficient to overcome refractoriness to chemotherapy. Combinations of drug-conjugated antibody or anti-BCL2 agents with R-CHOP could hold more promise, as shown by preliminary results of recent phase 1/2 studies (Zelenetz, Blood 128, 2016, 3032; Tilly, Blood 128, 2016, 1853).

Determination of COO status using gene-expression profiling has identified biologically distinct subtypes of DLBCL, including GCB and ABC origin subtypes (Lenz, Proc Natl Acad Sci USA 105, 2008, 13520-13525; Scott, J. Clin. Oncol. 33, 2015, 2848-2856). These molecular subtypes have important implications for oncogenesis and treatment outcome, as reflected by their inclusion in the current World Health Organization classification for DLBCL (Swerdlow, Blood 127, 2016, 2375-2390). Patients with the GCB subtype typically have more favorable outcomes, whereas the ABC subtype has been associated with inferior outcomes following chemotherapy or immunochemotherapy (including R-CHOP), and may represent a poor-risk subset of patients with unmet medical need (as shown in retrospective studies) (Lenz, Proc. Natl. Acad. Sci. USA loc. cit.; Scott 2015 loc. cit.). GOYA is the largest prospective study to assess the impact of COO on clinical outcomes. Comparison of PFS by COO subtype was consistent with a better outcome in GCB DLBCL, with the HR indicating a 70% increase in risk of disease progression in patients with ABC relative to GCB subtype. Outcome for the unclassified subgroup was similar to that of the ABC subgroup, which is in contrast to what has been reported in some prior studies (Scott 2015 loc. cit.). Interestingly, COO classification was not correlated with ORR and/or preliminary assessment of PFS in other prospectively defined studies, such as REMoDL-B (Davies, Blood 126, 2015, 812) or PYRAMID (Leonard loc. cit.), although these studies used different COO assays. Specific treatments aimed at COO subtypes of DLBCL may offer an alternative strategy for improving outcomes. Selectively targeting the B-cell receptor or NF-κB pathways, for example, may prove beneficial in DLBCL subtypes (ABC or non-GCB), as suggested by results of phase 2 studies that evaluated lenalidomide or ibrutinib with R-CHOP (Nowakowski, J Clin Oncol 33, 2015, 251-257; Vitolo, Lancet Oncol. 152014, 730-737; Younes, Lancet Oncol 15, 2014, 1019-1026). These strategies are currently being evaluated in randomized phase 3 studies.

The profile and nature of the AEs reported among G-CHOP-treated patients was as expected, with no new safety signals. The incidence of grade 3-5 AEs, SAEs, and treatment discontinuations due to AEs was slightly higher in the G-CHOP group than in the R-CHOP group, in keeping with what has been reported in other studies. These discrepancies may be due to different structural and biologic properties of G and R.

In conclusion, the current study demonstrated that G-CHOP did not improve PFS in a large population of patients with previously untreated DLBCL compared with R-CHOP, which remains the standard treatment for these patients. No new safety signals were identified.

EXAMPLE 3

Superiority of Obinutuzumab Over Rituximab in New Subgroups of DLBCL (Predictive Biomarker-Defined; Description and Results of Exploratory Analyses of the GOYA Clinical Phase 3 Study)

EXAMPLE 3.1

Gazyva™-CHOP is Superior to Ritixumab-CHOP in a Biomarker Defined Subset of DLBCL—Results from the Roche GOYA (BO21005) ph3 Clinical Trial Summary Rituximab (R) plus CHOP chemotherapy is standard-of-care in previously untreated diffuse large B-cell lymphoma (DLBCL). Obinutuzumab (G) is a glycoengineered, type II anti-CD20 monoclonal antibody. GOYA was a randomized phase 3 study comparing G-CHOP and R-CHOP in previously untreated advanced-stage DLBCL.

The GOYA trial in 1L DLBCL did not meet its primary endpoint: stratified HR, PFS: 0.92 (95% CI 0.76-1.12), but the GALLIUM trial demonstrated superiority of Gazyva over Rituximab in 1L FL (HR 0.66, 95% CI 0.51-0.85; currently in filing).

In exploratory analyses of GOYA, superiority of Gazyva™ over Rituximab is seen in a subset of GCB DLBCL patients and/or also in patients with mutations in CD58 and/or low expression of CD58. This is the first time a Gazyva benefit has been identified in a biomarker defined subgroup of DLBCL.

The results suggest that (a) subset(s) of GCB DLBCL patients that respond to Gazyva can be identified in several ways, e.g. by determining BCL2 translocation and BCL2 protein overexpression, and also by measuring gene expression profiling, e.g. Nanostring Cell of Origin (COO) assay using novel cutoffs for the Linear Predictor Score, LPS.

Methods

Cell-of-origin (COO) classification into subgroups germinal-center B-cell (GCB), activated B-cell (ABC), and Unclassified was based on gene-expression profiling using the NanoString Research Use Only Lymphoma Subtyping Test (NanoString Technologies, Inc., Seattle, Wash., USA).

The Linear Predictor Score (LPS) is a continuous variable (weighted average for gene expression of the genes in the Nanostring Lymphoma Subtyping assay) with a range in GOYA from −1138 to 4504. Normally the LPS used to classify patients into COO subgroups GCB, ABC, Unclassified. Default COO algorithm uses a bayesian approach with GCB/ABC classification based on ≥90% cut-off on likelihood of being GCB or ABC (unclassified works as a buffer).

The LPS has been analysed directly for clinical outcome for the first time. LPS was treated as a continuous variable for assessment of treatment effect (efficacy of G-CHOP vs. R-CHP) in exploratory un-specified analyses in the GOYA trial.

BCL-2 translocations were assessed using the Bcl-2 Dual Color Break Apart (Vysis, Abbott Molecular) and also with the Foundation Medicine next-generation sequencing assay, FoundationOne Heme. BCL-2 protein expression was assessed using a Ventana investigational-use IHC assay (BCL2 antibody clone, 124). Whole-transcriptome gene expression in the GOYA trial was evaluated using the TruSeq® RNA Access Library Prep Kit. CD58 mutations were identified using the FoundationOne heme gene panel.

Results

Figure 4:
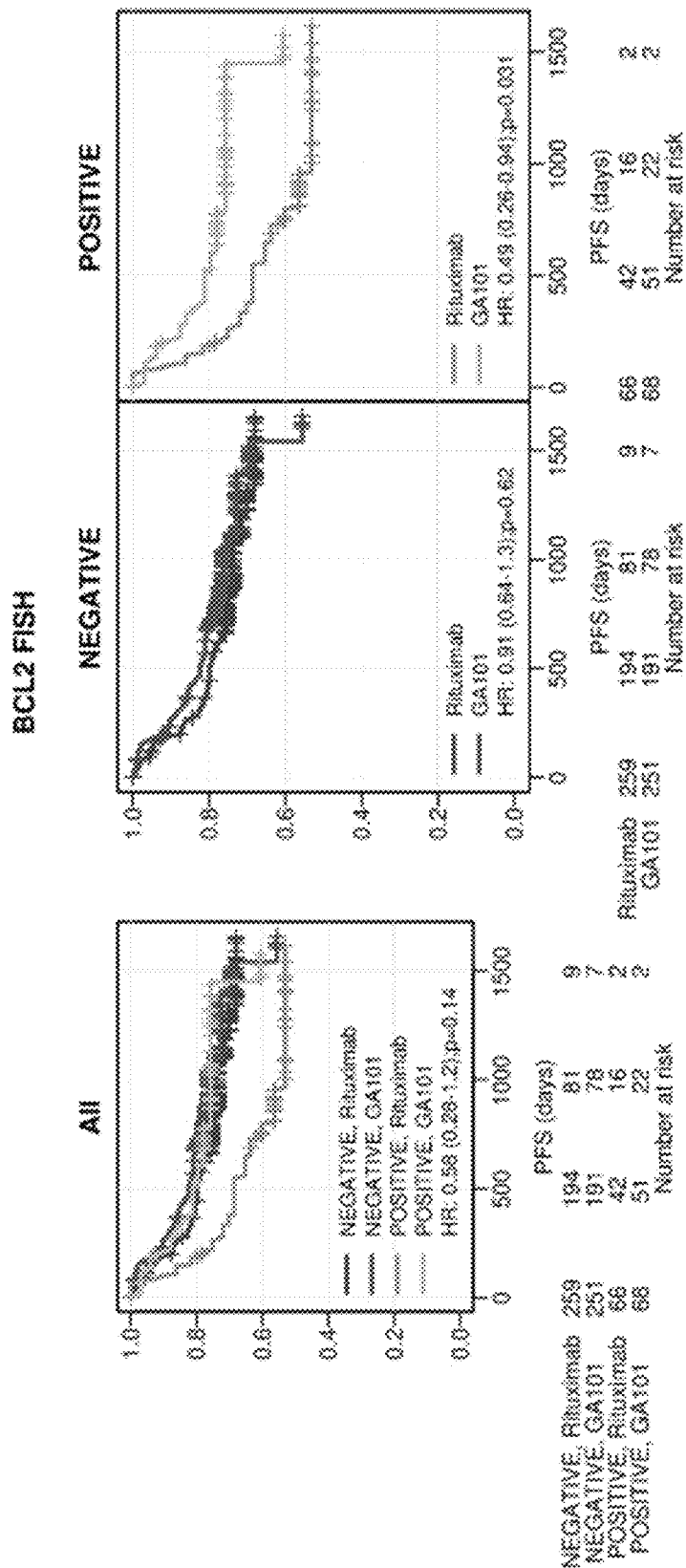
Figure 5:
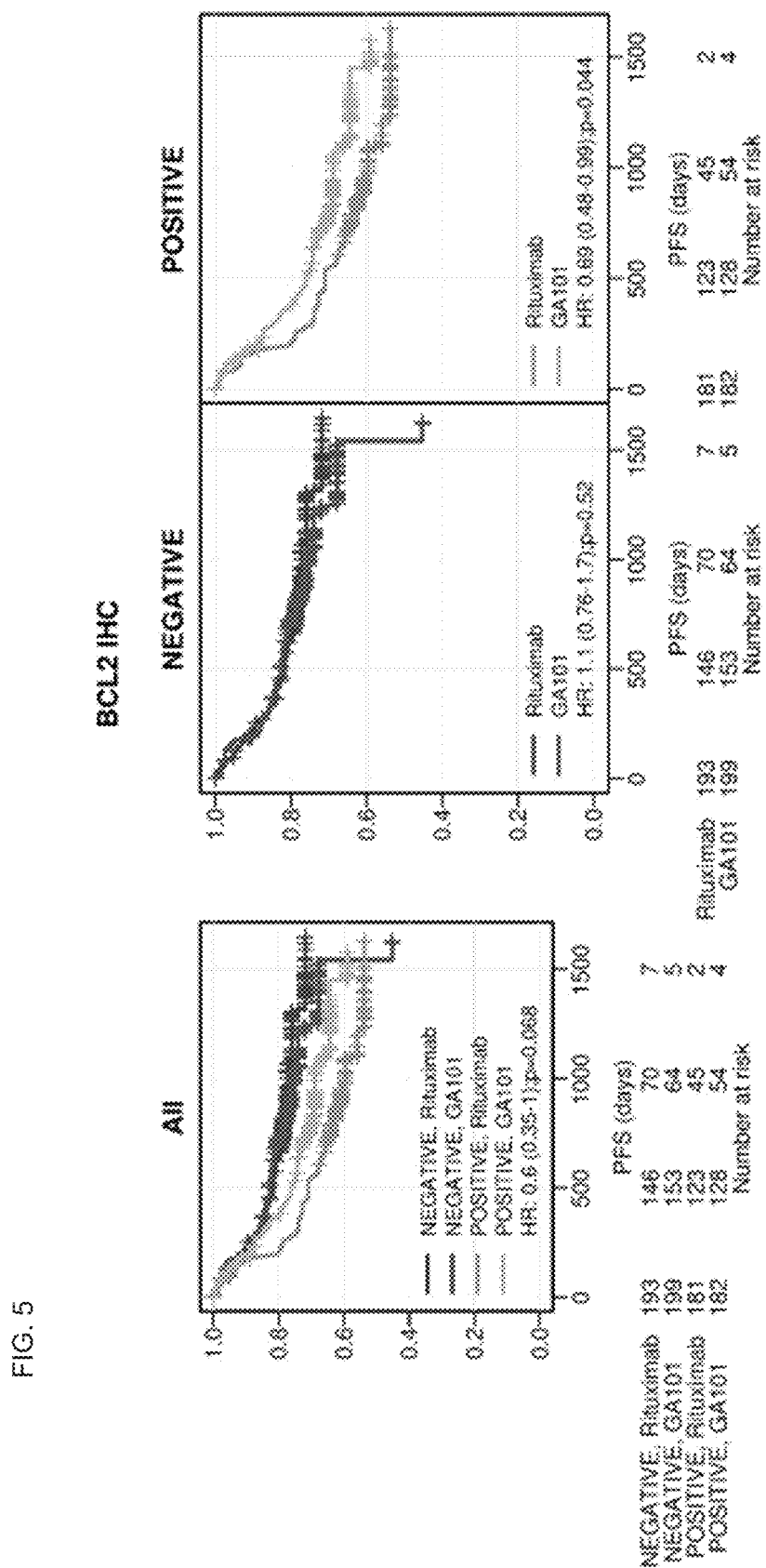
Figure 6:
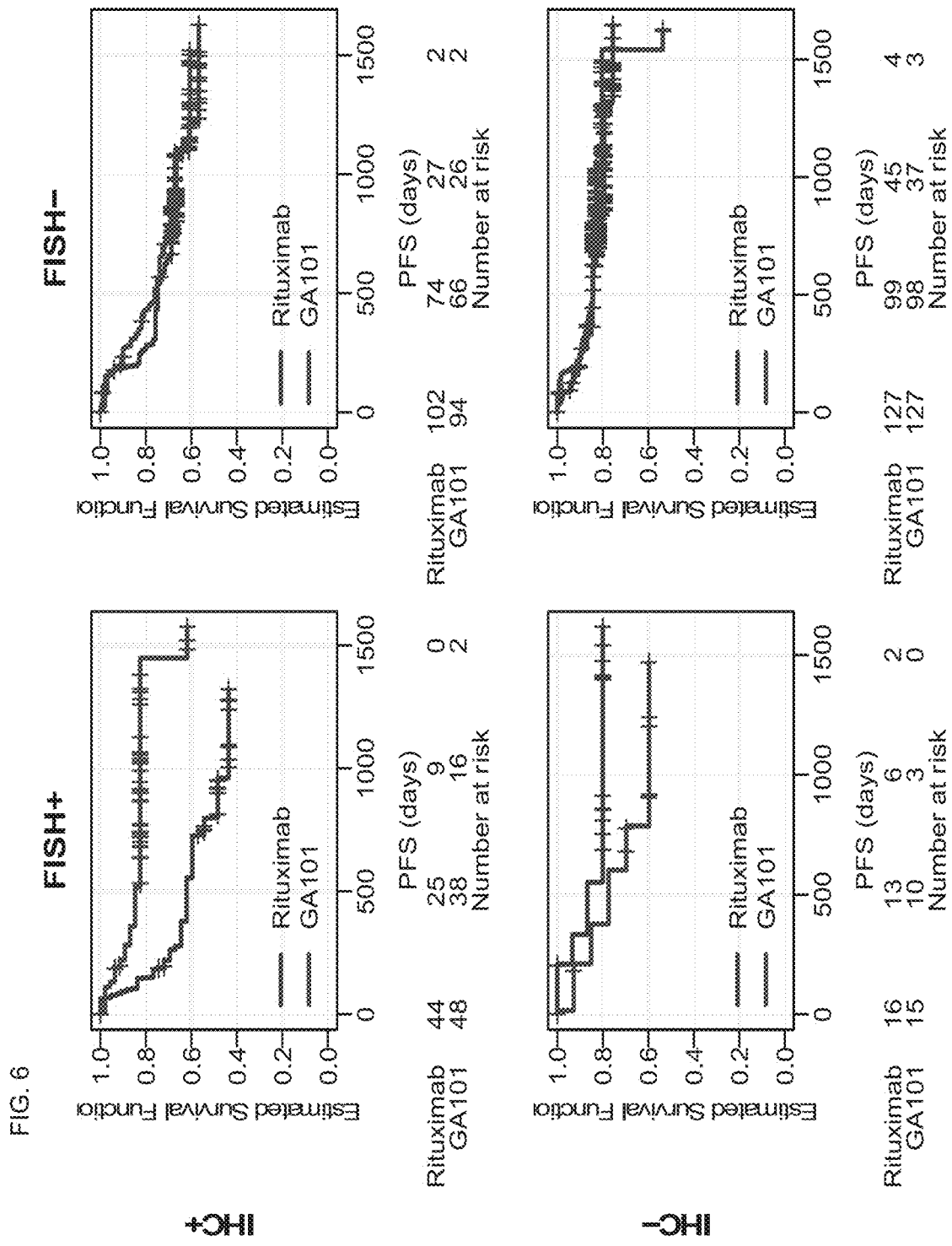
Figure 8:
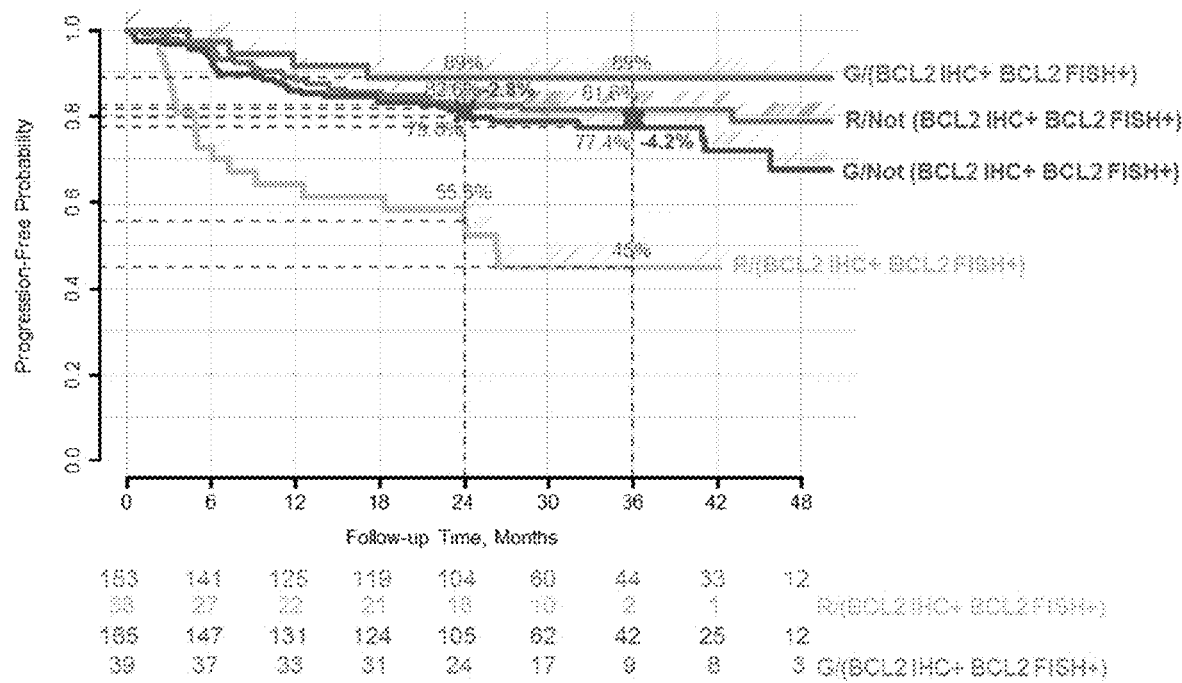
Figure 9:
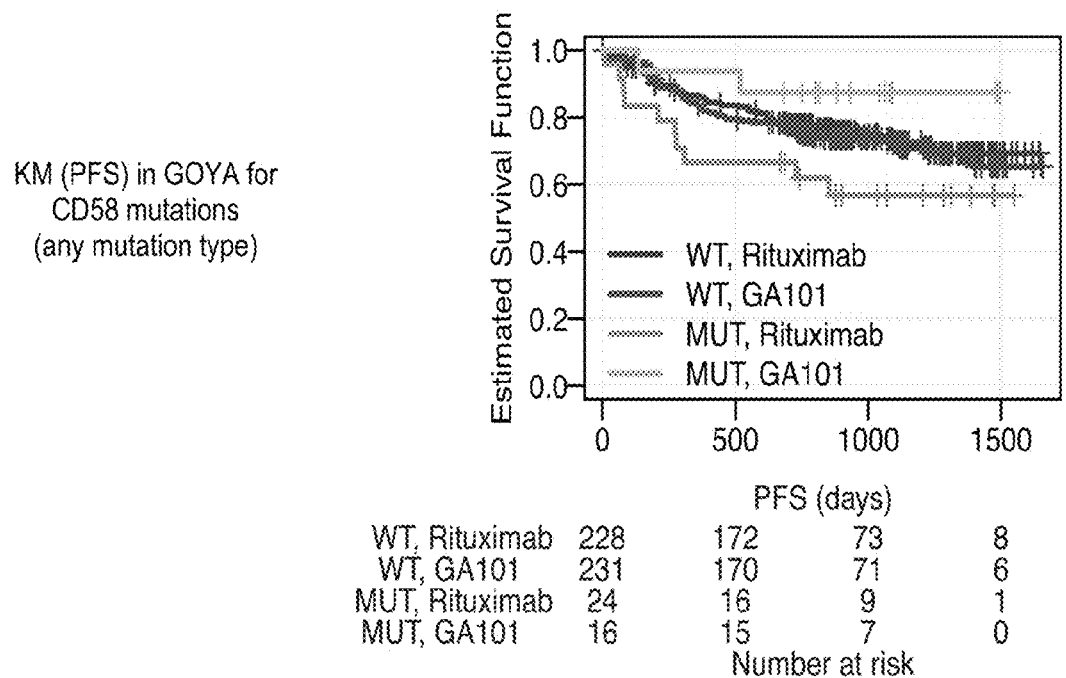

Biomarker defined subgroups of DLBCL were identified that benefit from G (G-CHOP) over R (R-CHOP):
 BCL2 translocated patients (see FIG. 4)
 BCL2 protein expression positive patients (see FIG. 5)
 BCL2 translocated patients that are BCL2 protein expression positive (see FIG. 6)
 A subset of GCB DLBCL patients. These can be identified as:
  Novel subgroup classification of GCB patients by novel cutoffs of the Linear Predictor Score into novel subgroup "strong-GCB" (patients with LPS<cutoff) (see FIGS. 7A-7C)
  or GCB patients with high BCL2 gene expression
  or GCB patients that are BCL2 protein expression positive
  or GCB patients with BCL2 translocation
  or GCB patients with BCL2 translocation that are BCL2 protein expression positive (see FIG. 8)
 In general, CD58 mutated patients, and/or patients with low expression of CD58 (see FIG. 9)

EXAMPLE 3.2

Superiority of Obinutuzumab Over Rituximab in a New Molecular FL-Like Subgroup of DLBCL—Results from the Phase 3 GOYA Trial Methods GOYA was an open-label, randomized phase 3 study comparing 1L G-CHOP with R-CHOP in 1418 DLBCL patients (pts). Biomarker testing was performed on formalin fixed, paraffin-embedded tumor tissue collected prior to treatment and tested retrospectively in central laboratories. COO was assessed using the NanoString Research Use Only LST (NanoString Technologies Inc., Seattle, Wash., USA) in 933 pts. Additional biomarker analyses used for molecualar characterization included DNA-targeted sequencing of 467 genes using the FoundationOne® Herne (FOH) panel (n=499 pts) and whole-transcriptome gene expression was evaluated using TruSeq® RNA sequencing in 552 pts. Vysis LSI Dual Color Break Apart ASH Probes were used to identify BCL2 translocations (n=644 pts; ASH cut-off, 50%), and the Ventana investigational-use IHC assay was used to assess BCL2 expression (BCL2 antibody clone, 124); BCL2+ IHC was defined as moderate/strong staining in ≥50% of tumor cells. Multivariate Cox regression and elastic net penalized regression (alpha=0.5) was used to evaluate biomarker treatment effects. In addition, bootstrap simulations were conducted to identify the optimal LPS (NanoString LST) to reflect the robustness of the observed treatment effectin GOYA and the generalizability of treatment effect to independent study populations. Multiple testing adjustment was done by estimating FDRs using the Benjamini-Hochberg procedure (significance, <5% FDR).

Pathway enrichment analysis was performed using a hypergeometric test; by gene-set enrichment using gene sets defined by MSigDB Hallmarks and a curated FL somatic mutation hallmark gene set based on a recent published review. All pts consented to the biomarker analyses.

Results

Figure 10:
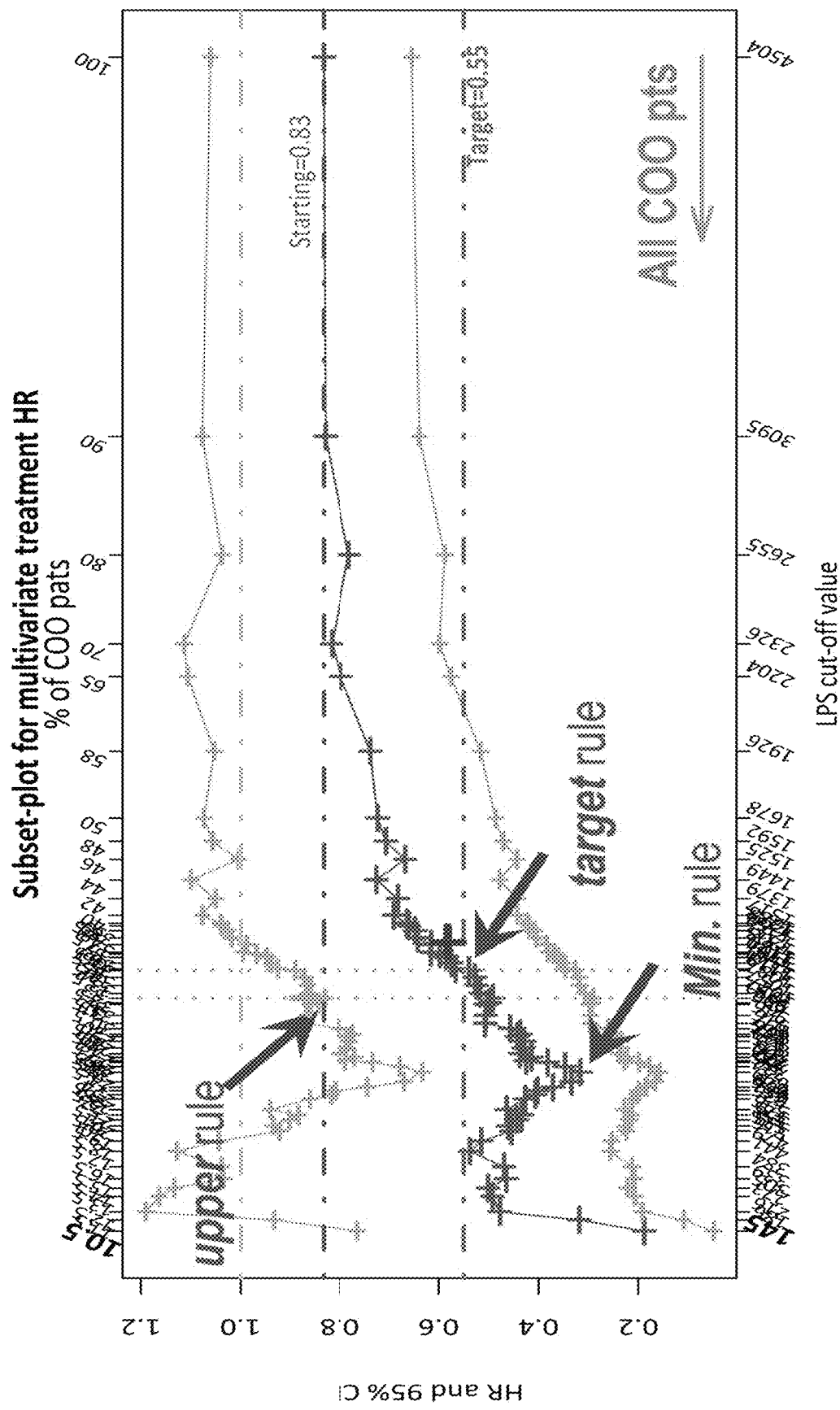
Figure 12:
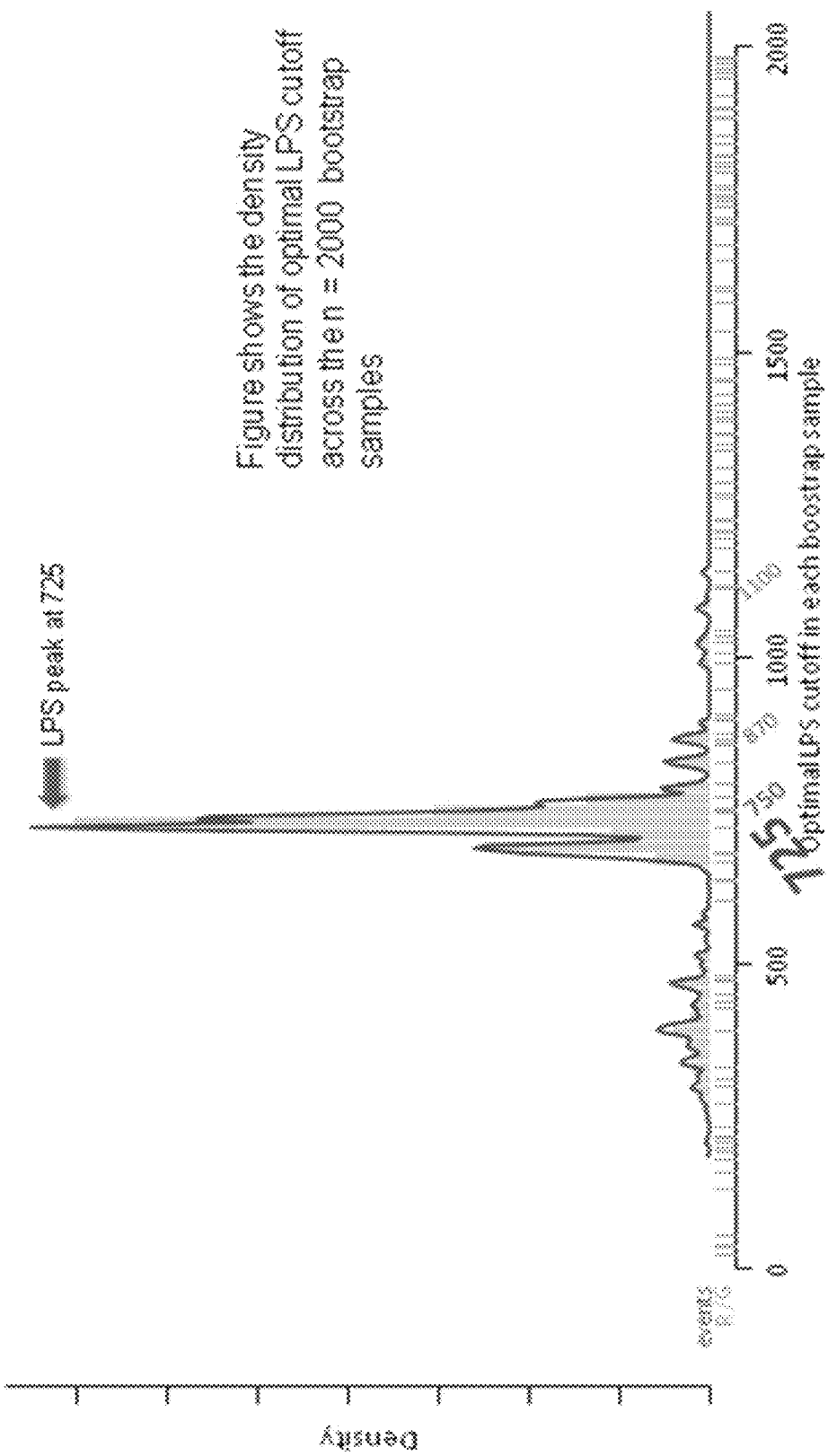

Assessment of LPS as a continuous variable identified a subgroup of GCB pts that benefitted from G-CHOP. In particular, strong expression of a germinal-center gene expression profile (by LPS) was linked with a benefit in outcome from treatment with G-CHOP vs R-CHOP among pts in GOYA. Bootstrap simulations identified an optimal LPS cut-off (≤725) for predicting G-CHOP benefit as the 25% (233/933) of GOYA pts with the lowest LPS scores. These pts are referred to as particularly 'strong-GCB' pts, and comprised 43% (233/540) of evaluable GCB pts in GOYA. Strong-GCB pts treated with G-CHOP achieved significantly better clinical outcomes in terms of investigator-assessed progression-free (HR=0.33, p=0.0007), event-free (HR=0.47, p=0.003), and overall survival (HR=0.41, p=0.019) than those treated with R-CHOP (cf. FIGS. 10, 12; Table 4). In multivariate analyses, the observed benefit was independent of baseline demographics and disease characteristics. Safety was similar with either regimen. FOH, TruSeq RNA, and BCL2 IHC/FISH GOYA data were used for molecular characterization of the strong-GCB pts. In gene-set analyses on the FOH data, compared with other GCB pts, strong-GCB pts were significantly enriched for mutations that are characteristic for FL pts ('weak-GCB': FDR, 3.54e-9). In particular, BCL2 translocations and mutations in several m7-FLIPI genes were highly enriched in strong-GCB pts vs other DLBCL subgroups (FIGS. 11A and 11B). There was no evidence for transformed indolent NHL in the strong-GCB subset on central pathology review.

CONCLUSIONS

By analyzing the data from the GOYA trial, identified was a new clinically and molecularly distinct subgroup of GCB DLBCL that comprises at least around 25% of all DLBCL pts, referred to as 'strong-GCB'. This distinct subgroup is identifiable by gene-expression profiling (using, for example, an LPS cutoff of ≤725 on the Nanostring LST assay) and characterized by mutations that are also commonly identified in FL pts (cf. Morin loc. cit.). Treatment with G-CHOP confers substantial clinical benefit over R-CHOP in this new subset of IL DLBCL patients.

The present invention refers the following nucleotide and amino acid sequences:

```
SEQ ID NO: 1:
Amino acid sequence of the heavy chain variable region of
obinutuzumab.
Mouse-human chimeric polypeptide.
Gln Val Gln Leu Val Gln Ser Gly Ala Glu Val Lys Lys Pro Gly Ser Ser Val Lys Val Ser Cys Lys Ala Ser Gly Tyr Ala Phe Ser Tyr Ser Trp Ile Asn Trp Val Arg Gln Ala Pro Gly Gln Gly Leu Glu Trp Met Gly Arg Ile Phe Pro Gly Asp Gly Asp Thr Asp Tyr Asn Gly Lys Phe Lys Gly Arg Val Thr Ile Thr Ala Asp Lys Ser Thr Ser Thr Ala Tyr Met Glu Leu Ser Ser Leu Arg Ser Glu Asp Thr Ala Val Tyr Tyr Cys Ala Arg Asn Val Phe Asp Gly Tyr Trp Leu Val Tyr Trp Gly Gln Gly Thr Leu Val Thr Val Ser Ser SEQ ID NO: 2: Amino acid sequence of the KV1 light chain variable
region of obinutuzumab
Mouse-human chimeric polypeptide
Asp Ile Val Met Thr Gln Thr Pro Leu Ser Leu Pro Val Thr Pro Gly Glu Pro Ala Ser Ile Ser Cys Arg Ser Ser Lys Ser Leu Leu His Ser Asn Gly Ile Thr Tyr Leu Tyr Trp Tyr Leu Gln Lys Pro Gly Gln Ser Pro Gln Leu Leu Ile Tyr Gln Met Ser Asn Leu Val Ser Gly Val Pro Asp Arg Phe Ser Gly Ser Gly Ser Gly Thr Asp Phe Thr Leu Lys Ile Ser Arg Val Glu Ala Glu Asp Val Gly Val Tyr Tyr Cys Ala Gln Asn Leu Glu Leu Pro Tyr Thr Phe Gly Gly Gly Thr Lys Val Glu Ile Lys Arg Thr Val SEQ ID NO: 3:
Nucleic acid sequence encoding the heavy chain variable region
of obinutuzumab
Mouse-human chimeric DNA
caggtgcaat tggtgcagtc tggcgctgaa gttaagaagc ctgggagttc agtgaaggtc    60
tcctgcaagg cttccggata cgccttcagc tattcttgga tcaattgggt gcggcaggcg   120
cctggacaag ggctcgagtg gatgggacgg atctttcccg gcgatgggga tactgactac   180
```

```
aatgggaaat tcaagggcag agtcacaatt accgccgaca atccactag cacagcctat  240 atggagctga gcagcctgag atctgaggac acggccgtgt attactgtgc aagaaatgtc  300
tttgatggtt actggcttgt ttactggggc cagggaaccc tggtcaccgt ctcctca    357

SEQ ID NO: 4:
Nucleic acid sequence encoding the KV1 light chain variable region
of obinutuzumab
Mouse-human chimeric DNA.
gatatcgtga tgacccagac tccactctcc ctgcccgtca cccctggaga gcccgccagc   60
attagctgca gagcctcttg ggtctagcaa cacagcaatg gcatcactta tttgtattgg  120
tacctgcaaa agccagggca gtctccacag ctcctgattt atcaaatgtc aaccttgtc   180 tctggcgtcc ctgaccggtt ctccggatcc gggtcaggca ctgatttcac actgaaaatc  240
agcagggtgg aggctgagga tgttggagtt tattactgcg ctcagaatct agaacttcct  300
tacaccttcg gcggagggac caaggtggag atcaaacgta cggtg                 345

SEQ ID NO: 5:
Amino acid sequence of the heavy chain of obinutuzumab.
The variable region comprises amino acid positions 1 to 119.
QVQLVQSGAE VKKPGSSVKV SCKASGYAFS YSWIHWVRQA PGQGLEWMGR   50

IFPGDGDTGY NGKFKGRVTI TADKSTSTAY MELSSLRSED TAVYYCARNV  100

FDGYWLVYWG QGTLVTVSSA STKGPSVFPL APSSKSTSGG TAALGCLVKD  150

YFPEPVTVSW NSGALTSGVH TFPAVLQSSG LYSLSSVVTV PSSSLGTQTY  200

ICNVNHKPSN TKVDKKVEPK SCDKTHTCPP CPAPELLGGP SVFLFPPKPK  250

DTLMISRTPE VTCVVVDVSH EDPEVKFNWY VDGVEVHNAK TKPREEQYNS  300

TYRVVSVLTV LHQDWLNGKE YKCKVSNKAL PAPIEKTISK AKGQPREPQV  350

YTLPPSRDEL TKNQVSLTCL VKGFYPSDIA VEWESNGQPE NNYKTTPPVL  400

DSDGSFFLYS KLTVDKSRWQ QGNVFSCSVM HEALHNHYTQ KSLSLSPGK   449

SEQ ID NO: 6:
Amino acid sequence of the KV1 light chain of obinutuzumab.
The variable region comprises amino acid positions 1 to 115.
DIVMTQTPLS LPVTPGEPAS ISCRSSKSLL HSNGITYLYW YLQKPGQSPQ   50'

LLIYQMSNLV SGVPDRFSGS GSGTDFTLKI SRVEAEDVGV YYCAQNLELP  100'

YTFGGGTKVE IKRTVAAFSV FIFPPSDEQL KSGTASVVCL LHNFYPREAK  150'

VQWKVDNALQ SGNSQESVTE QDSKDSTYSL SSTLTLSKAD YEKHKVYACE  200*

VTHQGLSSPV TKSFNRGEC                                   219'

SEQ ID NO: 7:
Nucleic acid sequence encoding the heavy chain variable region
of obinutuzumab (B-HH6).
CAGGTGCAATTGGTGCAGTCTGGCGCTGAAGTTAAGAAGCCTGGGAGTTCAGTGAAGGTCTCCTGCAAGG

CTTCCGGATACGCCTTCAGCTATTCTTGGATCAATTGGGTGCGGCAGGCGCCTGGACAAGGGCTCGAGTG

GATGGGACGGATCTTTCCCGGCGATGGGGATACTGACTACAATGGGAAATTCAAGGGCAGAGTCACAATT

ACCGCCGACAAATCCACTAGCACAGCCTATATGGAGCTGAGCAGCCTGAGATCTGAGGACACGGCCGTGT

ATTACTGTGCAAGAAATGTCTTTGATGGTTACTGGCTTGTTTACTGGGGCCAGGGAACCCTGGTCACCGT

CTCCTCA

SEQ ID NO: 8:
Nucleic acid sequence encoding the KV1 light chain variable
region of obinutuzumab.
GATATCGTGATGACCCAGACTCCACTCTCCCTGCCCGTCACCCCTGGAGAGCCCGCCAGCATFAGCTGCA

GGTCTAGCAAGAGCCTCTTGCACAGCAATGGCATCACTTATTTGTATTGGTACCTGCAAAAGCCAGGGCA

GTCTCCACAGCTCCTGATTTATCAAATGTCCAACCTTGTCTCTGGCGTCCCTGACCGGTTCTCCGGATCC
```

-continued

GGGTCAGGCACTGATTTCACACTGAAAATCAGCAGGGTGGAGGCTGAGGATGTTGGAGTTTATTACTGCG

CTCAGAATCTAGAACTTCCTTACACCTTCGGCGGAGGGACCAAGGTGGAGATCAAACGTACGGTG

SEQ ID NO: 9:
Amino acid requence of the heavy chain of rituximab.
Rituximab heavy chain chimeric.
QVQLQQPGAELVKPGASVKMSCKASGYTFTSYNMHWVKQTPGRGLEWIGAIYPGNGDTSY

NQKFKGKATLTADKSSSTAYMQLSSLTSEDSAVYYCARSTYYGGDWYFNVWGAGTTVTVS

AASTKGPSVFPLAPSSKSTSGGTAALGCLVKDYFPEPVTVSWNSGALTSGVHTFPAVLQS

SGLYSLSSVVTVPSSSLGTQTYICNVNHKPSNTKVDKKAEPKSCDKTHTCPPCPAPELLG

GPSVFLFPPKPKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREPQVYTLPPSRD

ELTKNQVSLTCLVKGFYPSDIAVEWESNGQPENNYKTTPPVLDSDGSFFLYSKLTVDKSR

WQQGNVFSCSVMHEALHNHYTQKSLSLSPGK

SEQ ID NO: 10:
Amino acid requence of the light chain of rituximab.
Rituximab light chain chimeric.
QIVLSQSPAILSASPGEKVTMTCRASSSVSYIHWFQQKPGSSPKPWIYATSNLASGVPVR

FSGSGSGTSYSLTISRVEAEDAATYYCQQWTSNPPTFGGGTKLEIKRTVAAPSVFIFPPS

DEQLKSGTASVVOLLNNFYPREAKVQWKVDNALQSGNSQESVTEQDSKDSTYSLSSTLTL

SKADYEKHKVYACEVTHQGLSSPVTKSFNRGEC

SEQ ID NO: 11:
Example of a nucleotide sequence encoding Homo sapiens (human) CD58
(variant 1).
   1 gggccgccgg ctgccagccc agggcgggc ggagccctac ttctggccga ccgcgtaggc 61 ggtgcttgaa cttagggctg cttgtggctg ggcactcgcg cagaggccgg cccgacgagc 121 catggttgct gggagcgacg cggggcgggc cctgggggtc ctcagcgtgg tctgcctgct 181 gcactgcttt ggtttcatca gctgtttttc ccaacaaata tatggtgttg tgtatgggaa 241 tgtaactttc catgtaccaa gcaatgtgcc tttaaaagag gtcctatgga aaaaacaaaa 301 ggataaagtt gcagaactgg aaaattctga attcagagct ttctcatctt ttaaaaatag 361 ggtttattta gacactgtgt caggtagcct cactatctac aacttaacat catcagatga 421 agatgagtat gaaatggaat cgccaaatat tactgatacc atgaagttct ttctttatgt 481 gcttgagtct cttccatctc ccacactaac ttgtgcattg actaatggaa gcattgaagt 541 ccaatgcatg ataccagagc attacaacag ccatcgagga cttataatgt actcatggga 601 ttgtcctatg gagcaatgta acgtaactc aaccagtata tattttaaga tggaaaatga 661 tcttccacaa aaaatacagt gtactcttag caatccatta tttaatacaa catcatcaat 721 cattttgaca acctgtatcc aagcagcgg tcattcaaga cacagatatg cacttatacc 781 cataccatta gcagtaatta caacatgtat tgtgctgtat atgaatggta ttctgaaatg 841 tgacagaaaa ccagacagaa ccaactccaa ttgattggta acagaagatg aagacaacag 901 cataactaaa ttatttttaaa aactaaaaag ccatctgatt tctcatttga gtattacaat 961 ttttgaacaa ctgttggaaa tgtaacttga agcagctgct ttaagaagaa atacccacta 1021 acaaagaaca agcattagtt ttggctgtca tcaacttatt atatgactag gtgcttgctt 1081 tttttgtcag taaattgttt ttactgatga gtagatact tttgtaaata aatgtaaata 1141 tgtacacaag tga SEQ ID NO: 12:
Example of an amino acid sequence of Homo sapiens (human) CD58
(isoform 1).

```
  1 mvagsdagra lgvlsvvcll hcfgfiscfs qqiygvvygn vtfhvpsnvp lkevlwkkqk
 61 dkvaelense frafssfknr vyldtvsgsl tiynitssde deyemespni tdtmkfflyv
121 leslpsptlt caltngsiev qcmipehyns hrglimyswd cpmeqckrns tsiyfkmend
181 lpqkiqctls nplfnttssi ilttcipssg hsrhryalip iplavittci vlymngilkc
241 drkpdrtnsn
```

SEQ ID NO: 13:
Example of a nucleotide sequence encoding Homo sapiens (human) BCL2
(variant alpha).

```
   1 tttctgtgaa gcagaagtct gggaatcgat ctggaaatcc tcctaattt tactccctct
  61 ccccgcgact cctgattcat tgggaagttt caaatcagct ataactggag agtgctgaag
 121 attgatggga tcgttgcctt atgcatttgt tttggtttta caaaaaggaa acttgacaga
 181 ggatcatgct gtacttaaaa aatacaacat cacagaggaa gtagactgat attaacaata
 241 cttactaata ataacgtgcc tcatgaaata aagatccgaa aggaattgga ataaaaattt
 301 cctgcatctc atgccaaggg ggaaacacca gaatcaagtg ttccgcgtga ttgaagacac
 361 cccctcgtcc aagaatgcaa agcacatcca ataaaatagc tggattataa ctcctcttct
 421 ttctctgggg gccgtggggt gggagctggg gcgagaggtg ccgttggccc ccgttgcttt
 481 tcctctggga aggatgggcg acgctgggag aacagggtac gataaccggg agatagtgat
 541 gaagtacatc cattataagc tgtcgcagag gggctacgag tgggatgcgg gagatgtggg
 601 cgccgcgccc ccgggggccg ccccgcacc gggcatcttc cctcccagc ccgggcacac
 661 gccccatcca gccgcatccc gggacccggt cgccaggacc tcgccgctgc agaccccggc
 721 tgcccccggc gccgccgcgg ggcctgcgct cagcccggtg ccacctgtgg tccacctgac
 781 cctccgccag gccggcgacg acttctcccg ccgctaccgc cgcgacttcg ccgagatgtc
 841 cagccagctg cacctgacgc ccttcaccgc gcggggacgc tttgccacgg tggtggagga
 901 gctcttcagg gacggggtga actggggag gattgtggcc ttctttgagt cggtggggt
 961 catgtgtgtg gagagcgtca accgggagat gtcgccctg gtggacaaca tcgccctgtg
1021 gatgactgag tacctgaacc ggcacctgca cacctggatc caggataacg gaggctggga
1081 tgcctttgtg gaactgtacg gccccagcat gcggcctctg tttgatttct cctggctgtc
1141 tctgaagact ctgctcagtt tggccctggt gggagcttgc atcaccctgg gtgcctatct
1201 gggccacaag tgaagtcaac atgcctgccc caaacaaata tgcaaaaggt tcactaaagc
1261 agtagaaata atatgcattg tcagtgatgt accatgaaac aaagctgcag gctgtttaag
1321 aaaaaataac acacatataa acatcacaca cacagacaga cacacacaca caacaatt
1381 aacagtcttc aggcaaaacg tcgaatcagc tatttactgc caagggaaa tatcatttat
1441 tttttacatt attaagaaaa aaagatttat ttatttaaga cagtcccatc aaaactcctg
1501 tctttggaaa tccgaccact aattgccaag caccgcttcg tgtggctcca cctggatgtt
1561 ctgtgcctgt aaacatagat tcgctttcca tgttgttggc cggatcacca tctgaagagc
1621 agacggatgg aaaaaggacc tgatcattgg ggaagctggc tttctggctg ctggaggctg
1681 gggagaaggt gttcattcac ttgcatttct ttgccctggg gctgtgata ttaacagagg
1741 gagggttcct gtgggggaa gtccatgcct ccctggcctg aagaagagac tctttgcata
1801 tgactcacat gatgcatacc tggtgggagg aaaagagttg gaacttcag atggacctag
1861 tacccactga gatttccacg ccgaaggaca gcgatgggaa aaatgccctt aaatcatagg
```

-continued

```
1921 aaagtatttt tttaagctac caattgtgcc gagaaaagca ttttagcaat ttatacaata 1981 tcatccagta ccttaagccc tgattgtgta tattcatata ttttggatac gcaccccca 2041 actcccaata ctggctctgt ctgagtaaga aacagaatcc tctggaactt gaggaagtga 2101 acatttcggt gacttccgca tcaggaaggc tagagttacc cagagcatca ggccgccaca 2161 agtgcctgct tttaggagac cgaagtccgc agaacctgcc tgtgtcccag cttggaggcc 2221 tggtcctgga actgagccgg ggccctcact ggcctcctcc agggatgatc aacagggcag 2281 tgtggtctcc gaatgtctgg aagctgatgg agctcagaat tccactgtca agaaagagca 2341 gtagagggt gtggctgggc ctgtcaccct ggggccctcc aggtaggccc gttttcacgt 2401 ggagcatggg agccacgacc cttcttaaga catgtatcac tgtagaggga aggaacagag 2461 gccctgggcc cttcctatca gaaggacatg gtgaaggctg gaacgtgag gagaggcaat 2521 ggccacggcc cattttggct gtagcacatg gcacgttggc tgtgtggcct tggcccacct 2581 gtgagtttaa agcaaggctt taaatgactt tggagagggt cacaaatcct aaaagaagca 2641 ttgaagtgag gtgtcatgga ttaattgacc cctgtctatg gaattacatg taaaacatta 2701 tcttgtcact gtagtttggt tttatttgaa aacctgacaa aaaaaaagtt ccaggtgtgg 2761 aatatggggg ttatctgtac atcctggggc attaaaaaaa aaatcaatgg tggggaacta 2821 taaagaagta acaaaagaag tgacatcttc agcaaataaa ctaggaaatt ttttttcttt 2881 ccagtttaga atcagccttg aaacattgat ggaataactc tgtggcatta ttgcattata 2941 taccatttat ctgtattaac tttggaatgt actctgttca atgtttaatg ctgtggttga 3001 tatttcgaaa gctgctttaa aaaatacat gcatctcagc gttttttgt ttttaattgt 3061 atttagttat ggcctataca ctatttgtga gcaaggtga tcgttttctg tttgagattt 3121 ttatctcttg attcttcaaa agcattctga gaaggtgaga taagccctga gtctcagcta 3181 cctaagaaaa acctggatgt cactggccac tgaggagctt tgtttcaacc aagtcatgtg 3241 catttccacg tcaacagaat tgtttattgt gacagttata tctgttgtcc ctttgacctt 3301 gtttcttgaa ggtttcctcg tccctgggca attccgcatt taattcatgg tattcaggat 3361 tacatgcatg tttggttaaa cccatgagat tcattcagtt aaaaatccag atggcaaatg 3421 accagcagat tcaaatctat ggtggtttga cctttagaga gttgctttac gtggcctgtt 3481 tcaacacaga cccacccaga gccctcctgc cctccttccg cggggctt ctcatggctg 3541 tccttcaggg tcttcctgaa atgcagtggt gcttacgctc caccaagaaa gcaggaaacc 3601 tgtggtatga agccagacct ccccggcggg cctcagggaa cagaatgatc agacctttga 3661 atgattctaa ttttaagca aaatattatt ttatgaaagg tttacattgt caaagtgatg 3721 aatatggaat atccaatcct gtgctgctat cctgccaaaa tcattttaat ggagtcagtt 3781 tgcagtatgc tccacgtggt aagatcctcc aagctgcttt agaagtaaca atgaagaacg 3841 tggacgtttt taatataaag cctgttttgt cttttgttgt tgttcaaacg ggattcacag 3901 agtatttgaa aaatgtatat atattaagag gtcacggggg ctaattgctg gctggctgcc 3961 ttttgctgtg gggttttgtt acctggtttt aataacagta aatgtgccca gcctcttggc 4021 cccagaactg tacagtattg tggctgcact tgctctaaga gtagttgatg ttgcatttc 4081 cttattgtta aaaacatgtt agaagcaatg aatgtatata aaagcctcaa ctagtcattt 4141 ttttctcctc ttctttttt tcattatatc taattatttt gcagttgggc aacagagaac 4201 catccctatt ttgtattgaa gagggattca catctgcatc ttaactgctc tttatgaatg 4261 aaaaaacagt cctctgtatg tactcctctt tacactggcc agggtcagag ttaaatagag 4321 tatatgcact ttccaaattg gggacaaggg ctctaaaaaa agccccaaaa ggagaagaac
```

-continued

```
4381 atctgagaac ctcctcggcc ctcccagtcc ctcgctgcac aaatactccg caagagaggc 4441 cagaatgaca gctgacaggg tctatggcca tcgggtcgtc tccgaagatt tggcaggggc 4501 agaaaactct ggcaggctta agatttggaa taaagtcaca gaattaagga agcacctcaa 4561 tttagttcaa acaagacgcc aacattctct ccacagctca cttacctctc tgtgttcaga 4621 tgtggccttc catttatatg tgatctttgt tttattagta aatgcttatc atctaaagat 4681 gtagctctgg cccagtggga aaattagga agtgattata atcgagagg agttataata 4741 atcaagatta aatgtaaata atcagggcaa tcccaacaca tgtctagctt tcacctccag 4801 gatctattga gtgaacagaa ttgcaaatag tctctatttg taattgaact tatcctaaaa 4861 caaatagttt ataaatgtga acttaaactc taattaattc caactgtact tttaaggcag 4921 tggctgtttt tagactttct tatcacttat agttagtaat gtacacctac tctatcagag 4981 aaaaacagga aaggctcgaa atacaagcca ttctaaggaa attagggagt cagttgaaat 5041 tctattctga tcttattctg tggtgtcttt tgcagcccag acaaatgtgg ttacacactt 5101 tttaagaaat acaattctac attgtcaagc ttatgaaggt tccaatcaga tctttattgt 5161 tattcaattt ggatctttca gggattttt ttttaaatta ttatgggaca aaggacattt 5221 gttggagggg tgggagggag gaagaatttt taaatgtaaa acattcccaa gtttggatca 5281 gggagttgga agttttcaga ataaccagaa ctaagggtat gaaggacctg tattggggtc 5341 gatgtgatgc ctctgcgaag aaccttgtgt gacaaatgag aaacattttg aagtttgtgg 5401 tacgaccttt agattccaga gacatcagca tggctcaaag tgcagctccg tttggcagtg 5461 caatggtata aatttcaagc tggatatgtc taatgggtat ttaaacaata aatgtgcagt 5521 tttaactaac aggatattta atgacaacct tctggttggt agggacatct gtttctaaat 5581 gtttattatg tacaatacag aaaaaaattt tataaaatta agcaatgtga aactgaattg 5641 gagagtgata atacaagtcc tttagtctta cccagtgaat cattctgttc catgtctttg 5701 gacaaccatg accttggaca atcatgaaat atgcatctca ctggatgcaa agaaaatcag 5761 atggagcatg aatggtactg taccggttca tctggactgc cccagaaaaa taacttcaag 5821 caaacatcct atcaacaaca aggttgttct gcataccaag ctgagcacag aagatgggaa 5881 cactggtgga ggatggaaag gctcgctcaa tcaagaaaat tctgagacta ttaataaata 5941 agactgtagt gtagatactg agtaaatcca tgcacctaaa cctttggaa aatctgccgt 6001 gggccctcca gatagctcat ttcattaagt ttttccctcc aaggtagaat ttgcaagagt 6061 gacagtggat tgcatttctt ttggggaagc tttcttttgg tggttttgtt tattatacct 6121 tcttaagttt tcaaccaagg tttgcttttg ttttgagtta ctggggttat ttttgtttta 6181 aataaaaata agtgtacaat aagtgttttt gtattgaaag cttttgttat caagattttc 6241 atacttttac cttccatggc tcttttaag attgatactt ttaagaggtg gctgatattc 6301 tgcaacactg tacacataaa aaatacggta aggatacttt acatggttaa ggtaaagtaa 6361 gtctccagtt ggccaccatt agctataatg gcacttttgtt tgtgttgttg gaaaaagtca 6421 cattgccatt aaactttcct tgtctgtcta gttaatattg tgaagaaaaa taaagtacag 6481 tgtgagatac tg
```

-continued

SEQ ID NO 14::
Example of an amino acid sequence of Homo sapiens (human) BCL2
(isoform alpha).
  1 mahagrtgyd nreivmkyih yklsqrgyew dagdvgaapp gaapapgifs sqpghtphpa 61 asrdpvarts plqtpaapga aagpalspvp pvvhltIrqa gddfsrryrr dfaemssqlh 121 ltpftargrf atvveelfrd gvnwgrivaf fefggymcve synremsply dnialwmtey 181 InrhIhtwiq dnggwdafve lygpsmrplf dfswIsIktlIslalvgaci tlgaylghk

The invention claimed is:

1. A method of treating a patient having a diffuse large B-cell lymphoma (DLBCL), the method comprising administering to the patient a therapeutically effective amount of a humanized Type II anti-CD20 antibody, wherein a tumor sample from the patient has a germinal center B-cell-like (GCB) cell-of-origin (COO) status;

wherein the humanized Type II anti-CD20 antibody comprises a heavy chain variable region comprising an amino acid sequence having at least 90% identity to SEQ ID NO: 1 and a light chain variable region comprising an amino acid sequence having at least 90% identity to SEQ ID NO: 2; and wherein the GCB COO status is a strong GCB COO status identified by a linear predictor score (LPS) for the tumor sample that is less than 1141, and wherein the LPS is a weighted sum of the expression levels of the genes TNFRSF13B, LIMD1, IRF4, CREB3L2, PIM2, CYB5R2, RAB7L1, CCDC50, MME, SERPINA9, ASB13, MAML3, ITPKB, MYBL1, S1PR2, R3HDM1, WDR55, ISY1, UBXN4, and TRIM56 and is calculated according the formula:

$$LPS(X)=\Sigma_j a_j X_j,$$

wherein $X_j$ is the gene expression for gene j and $a_j$ is the coefficient for gene j.

2. The method of claim 1, wherein the humanized Type II anti-CD20 antibody comprises a heavy chain variable region comprising the amino acid sequence of SEQ ID NO: 1 and a light chain variable region comprising the amino acid sequence of SEQ ID NO: 2.

3. The method of claim 1, wherein the tumor sample from the patient further has (a) one or more mutations in one or more of CREBBP, EP300, MEF2B, MYC, EZH2, and TNFRSF14 and (b) one or both of (i) one or more genetic mutations in CD58 and (ii) an expression level of CD58 that is less than 5.3 $\log_2$(nRPKM).

4. The method of claim 1, wherein the tumor sample from the patient further has one or both of (i) a translocation of BCL2 and (ii) a high expression level of BCL2 as compared to a control.

5. The method of claim 1, wherein the patient reaches an improved clinical outcome as compared to a patient treated with rituximab.

6. The method of claim 5, wherein the clinical outcome is progression-free survival (PFS), overall survival (OS), or event-free survival (EFS).

7. The method of claim 1, wherein the humanized Type II anti-CD20 antibody comprises a glycoengineered Fc region.

8. The method of claim 7, wherein the humanized Type II anti-CD20 antibody has an increase in the fraction of non-fucosylated oligosaccharides attached to the glycoengineered Fc region relative to an anti-CD20 antibody that comprises a non-glycoengineered Fc region.

9. The method of claim 8, wherein the non-fucosylated oligosaccharides are bisected non-fucosylated oligosaccharides.

10. The method of claim 1, wherein the humanized Type II anti-CD20 antibody has an increased affinity for human FcγRIII receptors relative to an anti-CD20 antibody that comprises a non-glycoengineered Fc region or rituximab.

11. The method of claim 1, wherein the humanized Type II anti-CD20 antibody is capable of causing increased antibody-dependent cellular cytotoxicity (ADCC) relative to a non-glycoengineered antibody.

12. The method of claim 1, wherein the humanized Type II anti-CD20 antibody is capable of causing increased ADCC relative to rituximab.

13. The method of claim 1, wherein the antibody is obinutuzumab.

14. The method of claim 1, further comprising administering to the patient one or more additional cytotoxic agents or chemotherapeutic agents.

15. The method of claim 14, further comprising administering to the patient ionizing radiation enhancing the effects of the one or more cytotoxic agents or the one or more chemotherapeutic agents.

16. The method of claim 14, comprising administering to the patient the chemotherapeutic agents (i) cyclophosphamide; (ii) doxorubicin; (iii) vincristine; and (iv) prednisone or prednisolone.

17. The method of claim 1, wherein the humanized Type II anti-CD20 antibody is administered to the patient in a pharmaceutical composition comprising a pharmaceutically acceptable carrier.

18. The method of claim 1, wherein the humanized Type II anti-CD20 antibody is administered intravenously at a dose of 1000 mg every three weeks.

19. The method of claim 18, wherein the humanized Type II anti-CD20 antibody is administered on days 1, 8, and 15 of a first 21-day treatment cycle and on day 1 of one or more additional 21-day treatment cycles.

20. The method of claim 19, wherein 8 cycles of treatment are administered.

21. The method of claim 1, wherein the tumor sample from the patient further has an expression level of CD58 that is less than or equal to 5.2 $\log_2$(nRPKM).

22. The method of claim 1, wherein the expression levels of the genes are mRNA expression levels.

23. The method of claim 1, wherein a strong GCB COO status of a tumor sample from the patient is identified by a LPS for the tumor sample that is less than or equal to 1100.

24. The method of claim 23, wherein a strong GCB COO status of a tumor sample from the patient is identified by a LPS for the tumor sample that is less than or equal to 749.

25. The method of claim 24, wherein a strong GCB COO status of a tumor sample from the patient is identified by a LPS for the tumor sample that is less than or equal to 725.

26. The method of claim 1, wherein the tumor sample from the patient further has one or more of:
(a) molecular follicular lymphoma (FL)-like features;
(b) one or more mutations in one or more of CREBBP, EP300, MEF2B, MYC, EZH2, and TNFRSF14;
(c) one or more mutations in CD58;
(d) an expression level of CD58 that is less than 5.3 $\log_2$(nRPKM);
(e) a translocation of BCL2; and
(f) expression of BCL2 in at least 50% of tumor cells.

* * * * *

UNITED STATES PATENT AND TRADEMARK OFFICE
CERTIFICATE OF CORRECTION

PATENT NO. : 11,597,772 B2
APPLICATION NO. : 16/784021
DATED : March 7, 2023
INVENTOR(S) : Mikkel Zahle Oestergaard It is certified that error appears in the above-identified patent and that said Letters Patent is hereby corrected as shown below:

In the Specification

Column 37, Table 3 title. replace "5%" with --$\geq$ 5%--.

Column 46, Line 37. replace "2 hours" with --$\geq$ 2 hours--.

Column 48, Line 43. replace "18 years" with --$\geq$ 18 years--.

Column 49, Line 27. replace "18 years." with --$\geq$ 18 years.--;
　　　Line 30. replace "50%" with --$\geq$ 50%--.

Column 71, Line 5. replace "pvvhltIrqa" with --pvvhltlrqa--;
　　　Line 6. replace "fefggymcve synremsply" with --fefggvmcve svnremsplv--;
　　　Line 7. replace "InrhIhtwiq" with --lnrhlhtwiq--;
　　　Line 7. replace "dfswIsIktlIslalvgaci" with --dfswlslktl lslalvgaci--.

Signed and Sealed this
Thirteenth Day of May, 2025

Coke Morgan Stewart
*Acting Director of the United States Patent and Trademark Office*

SEQUENCE LISTING

<160> NUMBER OF SEQ ID NOS: 14

<210> SEQ ID NO 1
<211> LENGTH: 119
<212> TYPE: PRT
<213> ORGANISM: Artificial Sequence
<220> FEATURE:
<223> OTHER INFORMATION: The heavy chain variable region of
      obinutuzumab; mouse-human chimeric polypeptide

<400> SEQUENCE: 1

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 2
<211> LENGTH: 115
<212> TYPE: PRT
<213> ORGANISM: Artificial Sequence
<220> FEATURE:
<223> OTHER INFORMATION: The KV1 light chain variable region of
      obinutuzumab; mouse-human chimeric polypeptide

<400> SEQUENCE: 2

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn

```
                     85                  90                  95
Leu Glu Leu Pro Tyr Thr Phe Gly Gly Gly Thr Lys Val Glu Ile Lys
                100                 105                 110

Arg Thr Val
        115

<210> SEQ ID NO 3
<211> LENGTH: 357
<212> TYPE: DNA
<213> ORGANISM: Artificial Sequence
<220> FEATURE:
<223> OTHER INFORMATION: Nucleic acid sequence encoding the heavy chain
      variable region of obinutuzumab; mouse-human chimeric DNA

<400> SEQUENCE: 3
caggtgcaat tggtgcagtc tggcgctgaa gttaagaagc ctgggagttc agtgaaggtc      60
tcctgcaagg cttccggata cgccttcagc tattcttgga tcaattgggt gcggcaggcg     120
cctggacaag gctcgagtg gatgggacgg atctttcccg gcgatgggga tactgactac      180
aatgggaaat tcaagggcag agtcacaatt accgccgaca atccactag cacagcctat      240 atggagctga gcagcctgag atctgaggac acggccgtgt attactgtgc aagaaatgtc     300
tttgatggtt actggcttgt ttactgggc cagggaaccc tggtcaccgt ctcctca          357

<210> SEQ ID NO 4
<211> LENGTH: 345
<212> TYPE: DNA
<213> ORGANISM: Artificial Sequence
<220> FEATURE:
<223> OTHER INFORMATION: nucleic acid sequence encoding the KV1 light
      chain variable region of obinutuzumab; mouse-human chimeric DNA

<400> SEQUENCE: 4
gatatcgtga tgacccagac tccactctcc ctgcccgtca cccctggaga gcccgccagc      60
attagctgca ggtctagcaa gagcctcttg cacagcaatg gcatcactta tttgtattgg     120
tacctgcaaa agccagggca gtctccacag ctcctgattt atcaaatgtc caaccttgtc     180
tctggcgtcc ctgaccggtt ctccggatcc gggtcaggca ctgatttcac actgaaaatc     240
agcagggtgg aggctgagga tgttggagtt tattactgcg ctcagaatct agaacttcct     300
tacaccttcg gcggagggac caaggtggag atcaaacgta cggtg                     345

<210> SEQ ID NO 5
<211> LENGTH: 449
<212> TYPE: PRT
<213> ORGANISM: Artificial Sequence
<220> FEATURE:
<223> OTHER INFORMATION: the heavy chain of obinutuzumab

<400> SEQUENCE: 5

Gln Val Gln Leu Val Gln Ser Gly Ala Glu Val Lys Lys Pro Gly Ser
1               5                  10                  15

Ser Val Lys Val Ser Cys Lys Ala Ser Gly Tyr Ala Phe Ser Tyr Ser
                20                  25                  30

Trp Ile Asn Trp Val Arg Gln Ala Pro Gly Gln Gly Leu Glu Trp Met
            35                  40                  45

Gly Arg Ile Phe Pro Gly Asp Gly Asp Thr Asp Tyr Asn Gly Lys Phe
        50                  55                  60

Lys Gly Arg Val Thr Ile Thr Ala Asp Lys Ser Thr Ser Thr Ala Tyr
65                  70                  75                  80
```

```
Met Glu Leu Ser Ser Leu Arg Ser Glu Asp Thr Ala Val Tyr Tyr Cys
                85                  90                  95
Ala Arg Asn Val Phe Asp Gly Tyr Trp Leu Val Tyr Trp Gly Gln Gly
            100                 105                 110
Thr Leu Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
    210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Asp Glu Leu Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445
Lys

<210> SEQ ID NO 6
<211> LENGTH: 219
<212> TYPE: PRT
<213> ORGANISM: Artificial Sequence
<220> FEATURE:
<223> OTHER INFORMATION: the KV1 light chain of obinutuzumab
```

<400> SEQUENCE: 6

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 7
<211> LENGTH: 357
<212> TYPE: DNA
<213> ORGANISM: Artificial Sequence
<220> FEATURE:
<223> OTHER INFORMATION: nucleic acid sequence encoding the heavy chain
      variable region of obinutuzumab (B-HH6)

<400> SEQUENCE: 7
caggtgcaat tggtgcagtc tggcgctgaa gttaagaagc ctgggagttc agtgaaggtc    60
tcctgcaagg cttccggata cgccttcagc tattcttgga tcaattgggt gcggcaggcg   120
cctggacaag gctcgagtg gatgggacgg atctttcccg gcgatgggga tactgactac   180
aatgggaaat tcaagggcag agtcacaatt accgccgaca atccactag cacagcctat   240 atggagctga gcagcctgag atctgaggac acggccgtgt attactgtgc aagaaatgtc   300
tttgatggtt actggcttgt ttactggggc cagggaaccc tggtcaccgt ctcctca      357

<210> SEQ ID NO 8
<211> LENGTH: 345
<212> TYPE: DNA
<213> ORGANISM: Artificial Sequence
<220> FEATURE:
<223> OTHER INFORMATION: nucleic acid sequence encoding the KV1 light
      chain variable region of obinutuzumab

<400> SEQUENCE: 8
gatatcgtga tgacccagac tccactctcc ctgcccgtca cccctggaga gccgccagc     60

```
attagctgca ggtctagcaa gagcctcttg cacagcaatg gcatcactta tttgtattgg    120
tacctgcaaa agccagggca gtctccacag ctcctgattt atcaaatgtc caaccttgtc    180
tctggcgtcc ctgaccggtt ctccggatcc gggtcaggca ctgatttcac actgaaaatc    240
agcagggtgg aggctgagga tgttggagtt tattactgcg ctcagaatct agaacttcct    300
tacaccttcg gcgagggac caaggtggag atcaaacgta cggtg                    345
```

<210> SEQ ID NO 9
<211> LENGTH: 451
<212> TYPE: PRT
<213> ORGANISM: Artificial Sequence
<220> FEATURE:
<223> OTHER INFORMATION: the heavy chain of rituximab

<400> SEQUENCE: 9

```
Gln Val Gln Leu Gln Gln Pro Gly Ala Glu Leu Val Lys Pro Gly Ala
 1               5                  10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Ala Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
```

```
                    305                 310                 315                 320
Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
                355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
    450

<210> SEQ ID NO 10
<211> LENGTH: 213
<212> TYPE: PRT
<213> ORGANISM: Artificial Sequence
<220> FEATURE:
<223> OTHER INFORMATION: the light chain of rituximab

<400> SEQUENCE: 10

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
                20                  25                  30

His Trp Phe Gln Gln Lys Pro Gly Ser Ser Pro Lys Pro Trp Ile Tyr
            35                  40                  45

Ala Thr Ser Asn Leu Ala Ser Gly Val Pro Val Arg Phe Ser Gly Ser
        50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
```

<210> SEQ ID NO 11
<211> LENGTH: 1153
<212> TYPE: DNA
<213> ORGANISM: Homo sapiens

<400> SEQUENCE: 11

```
gggccgccgg ctgccagccc agggcggggc ggagccctac ttctggccga ccgcgtaggc      60
ggtgcttgaa cttagggctg cttgtggctg ggcactcgcg cagaggccgg cccgacgagc     120
catggttgct gggagcgacg cggggcgggc cctgggggtc ctcagcgtgg tctgcctgct     180
gcactgcttt ggtttcatca gctgttttc ccaacaaata tatggtgttg tgtatgggaa      240
tgtaactttc catgtaccaa gcaatgtgcc tttaaaagag gtcctatgga aaaacaaaa      300
ggataaagtt gcagaactgg aaaattctga attcagagct ttctcatctt ttaaaaatag     360
ggtttattta dacactgtgt caggtagcct cactatctac aacttaacat catcagatga     420
agatgagtat gaaatggaat cgccaaatat tactgatacc atgaagttct ttctttatgt     480
gcttgagtct cttccatctc ccacactaac ttgtgcattg actaatggaa gcattgaagt     540
ccaatgcatg ataccagagc attacaacag ccatcgagga cttataatgt actcatggga     600
ttgtcctatg gagcaatgta acgtaactc aaccagtata tattttaaga tggaaaatga     660
tcttccacaa aaaatacagt gtactcttag caatccatta tttaatacaa catcatcaat     720
cattttgaca acctgtatcc caagcagcgg tcattcaaga cacagatatg cacttatacc     780
cataccatta gcagtaatta caacatgtat tgtgctgtat atgaatggta ttctgaaatg     840
tgacagaaaa ccagacagaa ccaactccaa ttgattggta acagaagatg aagacaacag     900
cataactaaa ttattttaaa aactaaaaag ccatctgatt tctcatttga gtattacaat     960
ttttgaacaa ctgttggaaa tgtaacttga agcagctgct ttaagaagaa atacccacta    1020
acaaagaaca agcattagtt ttggctgtca tcaacttatt atatgactag gtgcttgctt    1080
tttttgtcag taaattgttt ttactgatga tgtagatact tttgtaaata aatgtaaata    1140
tgtacacaag tga                                                       1153
```

<210> SEQ ID NO 12
<211> LENGTH: 250
<212> TYPE: PRT
<213> ORGANISM: Homo sapiens

<400> SEQUENCE: 12

```
Met Val Ala Gly Ser Asp Ala Gly Arg Ala Leu Gly Val Leu Ser Val
1               5                  10                  15

Val Cys Leu Leu His Cys Phe Gly Phe Ile Ser Cys Phe Ser Gln Gln
            20                  25                  30

Ile Tyr Gly Val Val Tyr Gly Asn Val Thr Phe His Val Pro Ser Asn
        35                  40                  45

Val Pro Leu Lys Glu Val Leu Trp Lys Lys Gln Lys Asp Lys Val Ala
    50                  55                  60

Glu Leu Glu Asn Ser Glu Phe Arg Ala Phe Ser Ser Phe Lys Asn Arg
65                  70                  75                  80

Val Tyr Leu Asp Thr Val Ser Gly Ser Leu Thr Ile Tyr Asn Leu Thr
                85                  90                  95

Ser Ser Asp Glu Asp Glu Tyr Glu Met Glu Ser Pro Asn Ile Thr Asp
            100                 105                 110
```

```
Thr Met Lys Phe Phe Leu Tyr Val Leu Glu Ser Leu Pro Ser Pro Thr
        115                 120                 125

Leu Thr Cys Ala Leu Thr Asn Gly Ser Ile Glu Val Gln Cys Met Ile
    130                 135                 140

Pro Glu His Tyr Asn Ser His Arg Gly Leu Ile Met Tyr Ser Trp Asp
145                 150                 155                 160

Cys Pro Met Glu Gln Cys Lys Arg Asn Ser Thr Ser Ile Tyr Phe Lys
                165                 170                 175

Met Glu Asn Asp Leu Pro Gln Lys Ile Gln Cys Thr Leu Ser Asn Pro
            180                 185                 190

Leu Phe Asn Thr Thr Ser Ser Ile Ile Leu Thr Thr Cys Ile Pro Ser
        195                 200                 205

Ser Gly His Ser Arg His Arg Tyr Ala Leu Ile Pro Ile Pro Leu Ala
    210                 215                 220

Val Ile Thr Thr Cys Ile Val Leu Tyr Met Asn Gly Ile Leu Lys Cys
225                 230                 235                 240

Asp Arg Lys Pro Asp Arg Thr Asn Ser Asn
                245                 250

<210> SEQ ID NO 13
<211> LENGTH: 6492
<212> TYPE: DNA
<213> ORGANISM: Homo sapiens

<400> SEQUENCE: 13
tttctgtgaa gcagaagtct gggaatcgat ctggaaatcc tcctaatttt tactccctct     60
ccccgcgact cctgattcat tgggaagttt caaatcagct ataactggag agtgctgaag    120
attgatggga tcgttgcctt atgcatttgt tttggtttta caaaaaggaa acttgacaga    180
ggatcatgct gtacttaaaa aatacaacat cacagaggaa gtagactgat attaacaata    240
cttactaata ataacgtgcc tcatgaaata aagatccgaa aggaattgga ataaaaattt    300
cctgcatctc atgccaaggg ggaaacacca gaatcaagtg ttccgcgtga ttgaagacac    360
cccctcgtcc aagaatgcaa agcacatcca ataaaatagc tggattataa ctcctcttct    420
ttctctgggg gccgtggggt gggagctggg gcgagaggtg ccgttggccc ccgttgcttt    480
tcctctggga aggatggcgc acgctggagg aacagggtac gataaccggg agatagtgat    540
gaagtacatc cattataagc tgtcgcagag gggctacgag tgggatgcgg agatgtgggg    600
cgccgcgccc ccgggggccg ccccgcacc gggcatcttc tcctcccagc ccgggcacac    660
gccccatcca gccgcatccc gggacccggt cgccaggacc tcgccgctgc agaccccggc    720 tgccccggc gccgccgcgg ggcctgcgct cagcccggtg ccacctgtgg tccacctgac    780
cctccgccag gccggcgacg acttctcccg ccgctaccgc cgcgacttcg ccgagatgtc    840
cagccagctg cacctgacgc ccttcaccgc gcggggacgc tttgccacgg tggtggagga    900
gctcttcagg gacggggtga actggggag gattgtggcc ttctttgagt cggtgggggt    960
catgtgtgtg gagagcgtca accgggagat gtcgcccctg gtggacaaca tcgccctgtg   1020
gatgactgag tacctgaacc ggcacctgca cacctggatc caggataacg gaggctggga   1080
tgcctttgtg gaactgtacg gccccagcat gcggcctctg tttgatttct cctggctgtc   1140
tctgaagact ctgctcagtt tggccctggt gggagcttgc atcaccctgg gtgcctatct   1200
gggccacaag tgaagtcaac atgcctgccc caaacaaata tgcaaaaggt tcactaaagc   1260
agtagaaata atatgcattg tcagtgatgt accatgaaac aaagctgcag gctgtttaag   1320
```

```
aaaaaataac acacatataa acatcacaca cacagacaga cacacacaca cacaacaatt    1380
aacagtcttc aggcaaaacg tcgaatcagc tatttactgc caaagggaaa tatcatttat    1440 ttttacatt  attaagaaaa aaagatttat ttatttaaga cagtcccatc aaaactcctg    1500
tctttggaaa tccgaccact aattgccaag caccgcttcg tgtggctcca cctggatgtt    1560
ctgtgcctgt aaacatagat tcgctttcca tgttgttggc cggatcacca tctgaagagc    1620
agacggatgg aaaaaggacc tgatcattgg ggaagctggc tttctggctg ctggaggctg    1680
gggagaaggt gttcattcac ttgcatttct ttgccctggg ggctgtgata ttaacagagg    1740
gagggttcct gtgggggaa  gtccatgcct ccctggcctg aagaagagac tctttgcata    1800
tgactcacat gatgcatacc tggtgggagg aaaagagttg gaacttcag  atggacctag    1860 tacccactga gatttccacg ccgaaggaca gcgatgggaa aaatgcccTT aaatcatagg    1920
aaagtatttt tttaagctac caattgtgcc gagaaaagca ttttagcaat ttatacaata    1980
tcatccagta ccttaagccc tgattgtgta tattcatata ttttggatac gcaccccca     2040 actcccaata ctggctctgt ctgagtaaga aacagaatcc tctggaactt gaggaagtga    2100
acatttcggt gacttccgca tcaggaaggc tagagttacc cagagcatca ggccgccaca    2160
agtgcctgct tttaggagac cgaagtccgc agaacctgcc tgtgtcccag cttggaggcc    2220
tggtcctgga actgagccgg ggccctcact ggcctcctcc agggatgatc aacagggcag    2280
tgtggtctcc gaatgtctgg aagctgatgg agctcagaat ccactgtca  agaaagagca    2340 gtagaggggt gtggctgggc ctgtcaccct ggggccctcc aggtaggccc gttttcacgt    2400
ggagcatggg agccacgacc cttcttaaga catgtatcac tgtagaggga aggaacagag    2460
gccctgggcc cttcctatca gaaggacatg gtgaaggctg ggaacgtgag gagaggcaat    2520
ggccacggcc cattttggct gtagcacatg gcacgttggc tgtgtggcct tggcccacct    2580
gtgagtttaa agcaaggctt taaatgactt tggagagggt cacaaatcct aaaagaagca    2640
ttgaagtgag gtgtcatgga ttaattgacc cctgtctatg gaattacatg taaaacatta    2700
tcttgtcact gtagtttggt tttatttgaa aacctgacaa aaaaaaagtt ccaggtgtgg    2760
aatatggggg ttatctgtac atcctggggc attaaaaaaa aaatcaatgg tggggaacta    2820
taaagaagta acaaaagaag tgacatcttc agcaaataaa ctaggaaatt ttttttctt     2880 ccagtttaga atcagccttg aaacattgat ggaataactc tgtggcatta ttgcattata    2940
taccatttat ctgtattaac tttggaatgt actctgttca atgtttaatg ctgtggttga    3000
tatttcgaaa gctgctttaa aaaatacat  gcatctcagc gttttttgt  ttttaattgt    3060 atttagttat ggcctataca ctatttgtga gcaaggtga  tcgttttctg tttgagattt    3120
ttatctcttg attcttcaaa agcattctga gaaggtgaga taagccctga gtctcagcta    3180
cctaagaaaa acctggatgt cactggccac tgaggagctt tgtttcaacc aagtcatgtg    3240
catttccacg tcaacagaat tgtttattgt gacagttata tctgttgtcc ctttgaccTT    3300
gtttcttgaa ggtttcctcg tccctgggca attccgcatt taattcatgg tattcaggat    3360
tacatgcatg tttggttaaa cccatgagat tcattcagtt aaaaatccag atggcaaatg    3420
accagcagat tcaaatctat ggtggtttga cctttagaga gttgctttac gtggcctgtt    3480
tcaacacaga cccacccaga gccctcctgc cctccttccg cgggggcttt ctcatggctg    3540
tccttcaggg tcttcctgaa atgcagtggt gcttacgctc caccaagaaa gcaggaaacc    3600
tgtggtatga agccagacct ccccggcggg cctcaggaa  cagaatgatc agaccttTga    3660
atgattctaa ttttaagca  aaatattatt ttatgaaagg tttacattgt caaagtgatg    3720
```

```
aatatggaat atccaatcct gtgctgctat cctgccaaaa tcattttaat ggagtcagtt   3780
tgcagtatgc tccacgtggt aagatcctcc aagctgcttt agaagtaaca atgaagaacg   3840
tggacgtttt taatataaag cctgttttgt cttttgttgt tgttcaaacg ggattcacag   3900
agtatttgaa aaatgtatat atattaagag gtcacggggg ctaattgctg gctggctgcc   3960
ttttgctgtg gggttttgtt acctggtttt aataacagta aatgtgccca gcctcttggc   4020
cccagaactg tacagtattg tggctgcact tgctctaaga gtagttgatg ttgcattttc   4080
cttattgtta aaacatgtt agaagcaatg aatgtatata aaagcctcaa ctagtcattt   4140
ttttctcctc ttcttttttt tcattatatc taattatttt gcagttgggc aacagagaac   4200
catccctatt ttgtattgaa gagggattca catctgcatc ttaactgctc tttatgaatg   4260
aaaaaacagt cctctgtatg tactcctctt tacactggcc agggtcagag ttaaatagag   4320
tatatgcact ttccaaattg gggacaaggg ctctaaaaaa agccccaaaa ggagaagaac   4380
atctgagaac ctcctcggcc ctcccagtcc ctcgctgcac aaatactccg caagagaggc   4440
cagaatgaca gctgacaggg tctatggcca tcgggtcgtc tccgaagatt tggcaggggc   4500
agaaaactct ggcaggctta agatttggaa taaagtcaca gaattaagga agcacctcaa   4560
tttagttcaa acaagacgcc aacattctct ccacagctca cttacctctc tgtgttcaga   4620
tgtggccttc catttatatg tgatcttgt tttattagta aatgcttatc atctaaagat   4680
gtagctctgg cccagtggga aaaattagga agtgattata aatcgagagg agttataata   4740
atcaagatta aatgtaaata atcagggcaa tcccaacaca tgtctagctt tcacctccag   4800
gatctattga gtgaacagaa ttgcaaatag tctctatttg taattgaact tatcctaaaa   4860
caaatagttt ataaatgtga acttaaactc taattaattc caactgtact tttaaggcag   4920
tggctgtttt tagactttct tatcacttat agttagtaat gtacacctac tctatcagag   4980
aaaaacagga aaggctcgaa atacaagcca ttctaaggaa attagggagt cagttgaaat   5040
tctattctga tcttattctg tggtgtcttt tgcagcccag acaaatgtgg ttacacactt   5100
tttaagaaat acaattctac attgtcaagc ttatgaaggt tccaatcaga tctttattgt   5160
tattcaattt ggatctttca gggatttttt ttttaaatta ttatgggaca aaggacattt   5220
gttggagggg tgggagggag gaagaatttt taaatgtaaa acattcccaa gtttggatca   5280
gggagttgga agttttcaga ataaccagaa ctaagggtat gaaggacctg tattggggtc   5340
gatgtgatgc ctctgcgaag aaccttgtgt gacaaatgag aaacattttg aagtttgtgg   5400
tacgaccttt agattccaga gacatcagca tggctcaaag tgcagctccg tttggcagtg   5460
caatggtata aatttcaagc tggatatgtc taatgggtat ttaaacaata aatgtgcagt   5520
tttaactaac aggatattta atgacaacct tctggttggt agggacatct gtttctaaat   5580
gtttattatg tacaatacag aaaaaaattt tataaaatta agcaatgtga aactgaattg   5640
gagagtgata atacaagtcc tttagtctta cccagtgaat cattctgttc catgtctttg   5700
gacaaccatg accttggaca atcatgaaat atgcatctca ctggatgcaa agaaaatcag   5760
atggagcatg aatggtactg taccggttca tctggactgc cccagaaaaa taacttcaag   5820
caaacatcct atcaacaaca aggttgttct gcataccaag ctgagcacag aagatgggaa   5880
cactggtgga ggatggaaag gctcgctcaa tcaagaaaat tctgagacta ttaataaata   5940
agactgtagt gtagatactg agtaaatcca tgcacctaaa ccttttggaa aatctgccgt   6000
gggccctcca gatagctcat ttcattaagt tttccctcc aaggtagaat ttgcaagagt   6060
```

-continued

```
gacagtggat tgcatttctt ttggggaagc tttcttttgg tggttttgtt tattatacct    6120
tcttaagttt tcaaccaagg tttgcttttg ttttgagtta ctggggttat ttttgtttta    6180
aataaaaata agtgtacaat aagtgttttt gtattgaaag cttttgttat caagattttc    6240
atacttttac cttccatggc tcttttaag attgatactt ttaagaggtg gctgatattc     6300
tgcaacactg tacacataaa aaatacggta aggatacttt acatggttaa ggtaaagtaa    6360
gtctccagtt ggccaccatt agctataatg gcactttgtt tgtgttgttg gaaaaagtca    6420
cattgccatt aaactttcct tgtctgtcta gttaatattg tgaagaaaaa taaagtacag    6480
tgtgagatac tg                                                         6492
```

<210> SEQ ID NO 14
<211> LENGTH: 239
<212> TYPE: PRT
<213> ORGANISM: Homo sapiens

<400> SEQUENCE: 14

```
Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
            20                  25                  30

Gly Asp Val Gly Ala Ala Pro Pro Gly Ala Ala Pro Ala Pro Gly Ile
        35                  40                  45

Phe Ser Ser Gln Pro Gly His Thr Pro His Pro Ala Ala Ser Arg Asp
    50                  55                  60

Pro Val Ala Arg Thr Ser Pro Leu Gln Thr Pro Ala Ala Pro Gly Ala
65                  70                  75                  80

Ala Ala Gly Pro Ala Leu Ser Pro Val Pro Pro Val Val His Leu Thr
                85                  90                  95

Leu Arg Gln Ala Gly Asp Asp Phe Ser Arg Arg Tyr Arg Arg Asp Phe
            100                 105                 110

Ala Glu Met Ser Ser Gln Leu His Leu Thr Pro Phe Thr Ala Arg Gly
        115                 120                 125

Arg Phe Ala Thr Val Val Glu Glu Leu Phe Arg Asp Gly Val Asn Trp
    130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
            180                 185                 190

Gly Gly Trp Asp Ala Phe Val Glu Leu Tyr Gly Pro Ser Met Arg Pro
        195                 200                 205

Leu Phe Asp Phe Ser Trp Leu Ser Leu Lys Thr Leu Leu Ser Leu Ala
    210                 215                 220

Leu Val Gly Ala Cys Ile Thr Leu Gly Ala Tyr Leu Gly His Lys
225                 230                 235
```